United States Patent
Kwon et al.

(10) Patent No.: US 12,144,246 B2
(45) Date of Patent: Nov. 12, 2024

(54) COMPOUNDS, INFRARED ABSORBERS, INFRARED ABSORBING/BLOCKING FILMS, PHOTOELECTRIC DEVICES, SENSORS, AND ELECTRONIC DEVICES

(71) Applicant: Samsung Electronics Co., Ltd., Suwon-si (KR)

(72) Inventors: Ohkyu Kwon, Seoul (KR); Changki Kim, Suwon-si (KR); Hyesung Choi, Seoul (KR); Hwang Suk Kim, Suwon-si (KR); Insun Park, Suwon-si (KR); Dong-Seok Leem, Seongnam-si (KR)

(73) Assignee: Samsung Electronics Co., Ltd., Gyeonggi-do (KR)

(*) Notice: Subject to any disclaimer, the term of this patent is extended or adjusted under 35 U.S.C. 154(b) by 774 days.

(21) Appl. No.: 17/363,543

(22) Filed: Jun. 30, 2021

(65) Prior Publication Data
US 2022/0059772 A1  Feb. 24, 2022

(30) Foreign Application Priority Data
Jun. 30, 2020  (KR) .................. 10-2020-0080484

(51) Int. Cl.
| | | |
|---|---|---|
| H10K 30/30 | (2023.01) | |
| C07D 409/14 | (2006.01) | |
| C07D 495/14 | (2006.01) | |
| C07D 517/04 | (2006.01) | |
| H10K 85/60 | (2023.01) | |
| H10K 39/32 | (2023.01) | |

(52) U.S. Cl.
CPC ......... H10K 85/636 (2023.02); C07D 409/14 (2013.01); C07D 495/14 (2013.01); C07D 517/04 (2013.01); H10K 85/655 (2023.02); H10K 85/657 (2023.02); H10K 85/6572 (2023.02); H10K 30/30 (2023.02); H10K 39/32 (2023.02)

(58) Field of Classification Search
CPC .. H10K 85/636; H10K 85/655; H10K 85/657; H10K 85/6572; H10K 39/82; H10K 30/30; C07D 409/14; C07D 495/14; C07D 517/04

See application file for complete search history.

(56) References Cited

U.S. PATENT DOCUMENTS

| 901,786 A | 10/1908 | Curwen |
|---|---|---|
| 4,830,951 A | 5/1989 | Dust et al. |
| 4,939,012 A | 7/1990 | Dust et al. |
| 5,187,043 A | 2/1993 | Santoh et al. |
| 6,767,677 B2 | 7/2004 | Williams |
| 8,232,471 B2 | 7/2012 | Nomura et al. |
| 8,319,090 B2 | 11/2012 | Kitamura |
| 9,085,537 B2 | 7/2015 | Nomura et al. |
| 10,377,901 B2* | 8/2019 | Henary ............ C09K 11/025 |
| 2008/0230123 A1 | 9/2008 | Mitsui et al. |
| 2014/0054577 A1 | 2/2014 | Mitsui et al. |
| 2018/0259849 A1 | 9/2018 | Hirai et al. |
| 2019/0194385 A1 | 6/2019 | Azoulay et al. |
| 2019/0214578 A1 | 7/2019 | Sugawara et al. |
| 2020/0136063 A1 | 4/2020 | Kwon et al. |
| 2020/0176690 A1 | 6/2020 | Kuzumoto et al. |
| 2021/0173304 A1 | 6/2021 | Arayama et al. |

FOREIGN PATENT DOCUMENTS

| EP | 1108757 A2 | 6/2001 |
|---|---|---|
| JP | 2008-057569 A | 3/2008 |
| JP | 2017-025039 A | 2/2017 |
| JP | 2020-083866 A | 6/2020 |
| KR | 10-2020-0047344 A | 5/2020 |
| KR | 10-2020-0067039 A | 6/2020 |
| WO | WO-2016/025620 A1 | 2/2016 |
| WO | WO-2017/146187 A1 | 8/2017 |
| WO | WO-2018/008721 A1 | 1/2018 |
| WO | WO-18039347 A2 | 3/2018 |

(Continued)

OTHER PUBLICATIONS

Extended European Search Report dated Nov. 11, 2021 for corresponding European Application No. 21182685.4.
L.A. Padilha et al. 'Excited state absorption and decay kinetics of near IR polymethine dyes' Chemical Physics, 2008, vol. 352, pp. 97-105.
Karen Strassel et al., "Squaraine Dye for a Visibly Transparent All-Organic Optical Upconversion Device with Sensitivity at 1000 nm" ACS Publications, 2018, 10, 11063-11069.

(Continued)

*Primary Examiner* — Timothy R Rozof
(74) *Attorney, Agent, or Firm* — Harness, Dickey & Pierce, P.L.C.

(57) ABSTRACT

A compound is represented by Chemical Formula 1.

[Chemical Formula 1]

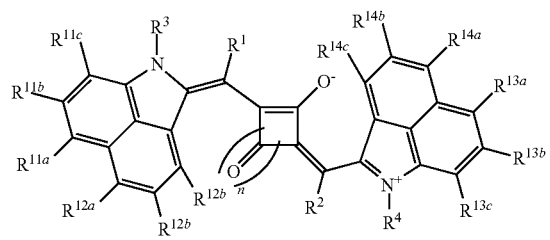

In Chemical Formula 1, $R^1$ to $R^4$, $R^{11a}$ to $R^{14c}$, and n are the same as defined in the detailed description.

42 Claims, 13 Drawing Sheets

(56) References Cited

FOREIGN PATENT DOCUMENTS

WO    WO-2020/054719 A1    3/2020

OTHER PUBLICATIONS

Sushil Khopkar et al., "Synthesis, Photophysical Properties and Applications of NIR Absorbing Unsymmetrical Squarines: A Review" *Dyes and Pigments*, Elsevier, Jun. 2019.

Gang Qian et al., "Simple and Efficient Near-Infrared Organic Chromophores for Light-Emitting Diodes with a Single Electroluminescent Emission Above 1000 nm" Wiley Interscience, 2009, 21, 111-116.

Weichuan Yao et al., "Organic Bulk Heterojunction Infrared Photodiodes for Imaging out to 1300 nm" ACS Publications, 2019, 1, 660-666.

Yuki Haishima et al., "Wide-Range Near-Infrared Sensitizing 1 H-Benzo[c,d]indol-2-ylidene-Based Squaraine Dyes for Dye-Sensitized Solar Cells" *The Journal of Organic Chemisty*, ACS Publications, 2018, 83, 4389-4401.

\* cited by examiner

COMPOUNDS, INFRARED ABSORBERS, INFRARED ABSORBING/BLOCKING FILMS, PHOTOELECTRIC DEVICES, SENSORS, AND ELECTRONIC DEVICES

CROSS-REFERENCE TO RELATED APPLICATION

This application claims priority to and the benefit under 35 U.S.C. § 119 of Korean Patent Application No. 10-2020-0080484 filed in the Korean Intellectual Property Office on Jun. 30, 2020, the entire contents of which are incorporated herein by reference.

BACKGROUND

1. Field

Compounds, infrared absorbers, infrared (IR) absorbing/blocking films, photoelectric devices, organic sensors, and electronic devices are disclosed.

2. Description of the Related Art

An imaging device is used in a digital camera and a camcorder, etc., to capture an image and to store it as an electrical signal, and the imaging device includes a sensor separating incident light according to a wavelength and converting each component to an electrical signal.

SUMMARY

Some example embodiments provide a compound having improved infrared absorption properties.

Some example embodiments provide an infrared absorber and an infrared absorbing/blocking film including the compound.

Some example embodiments provide a photoelectric device including the compound. Such photoelectric device may provide improved sensitivity of a sensor in a low-illumination environment and/or may be used as a biometric device.

Some example embodiments provide a composition including the compound.

Some example embodiments provide an organic sensor including the compound or the photoelectric device.

Some example embodiments provide an electronic device including the photoelectric device or the organic sensor.

According to some example embodiments, a compound represented by Chemical Formula 1 is provided.

[Chemical Formula 1]

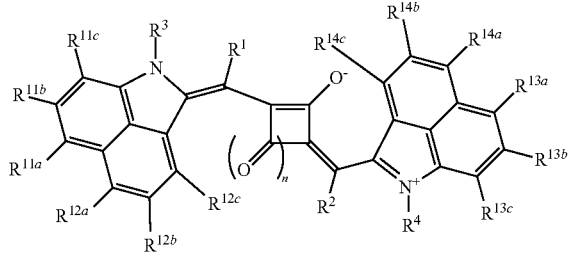

In Chemical Formula 1,
$R^1$ to $R^4$ may each independently be hydrogen, deuterium, a C1 to C10 alkyl group, a C1 to C10 alkoxy group, a C1 to C10 haloalkyl group, a C6 to C14 aryl group, or a C3 to C12 heteroaryl group,
$R^{11a}$ to $R^{14c}$ may each independently be hydrogen, deuterium, a halogen, a cyano group, a C1 to C10 alkyl group, a C1 to C10 alkoxy group, a C1 to C10 haloalkyl group, a C6 to C14 aryl group, a C6 to C14 aryloxy group, a C3 to C12 heteroaryl group, or a functional group represented by Chemical Formula 1A, wherein at least one of $R^{11a}$ to $R^{14c}$ is a functional group represented by Chemical Formula 1A, wherein $R^{11a}$ to $R^{14c}$ are present independently of each other or an adjacent two of $R^{11a}$ to $R^{14c}$ are linked to each other to form a fused ring with benzoindole, and
n may be an integer of 1 or 2, $$*\text{-}L_1\text{-}(L_2)_m\text{-}Ar \qquad \text{[Chemical Formula 1A]}$$

wherein, in Chemical Formula 1A,
$L_1$ may be a substituted or unsubstituted C2 to C15 heteroaromatic ring group,
$L_2$ may be a substituted or unsubstituted C2 to C15 heteroaromatic ring group, a substituted or unsubstituted C6 to C30 aromatic ring group, a substituted or unsubstituted C1 to C10 alkylene group, or a substituted or unsubstituted C3 to C20 cycloalkylene group,
Ar may be a substituted or unsubstituted C6 to C30 aromatic ring group, a substituted or unsubstituted C2 to C30 heteroaromatic ring group, a fused ring thereof, a substituted or unsubstituted C6 to C30 arylamine group, or a substituted or unsubstituted C2 to C30 heteroarylamine group, and
m may be 0, 1, or 2.

In Chemical Formula 1A, $L_1$ and $L_2$ may each independently be a heteroaromatic ring group represented by one of Chemical Formulas 1A-11 to 1A-15, or a combination thereof.

[Chemical Formulas 1A-11 to 1A-15]

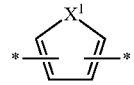
(1A-11)

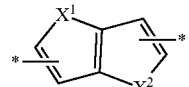
(1A-12)

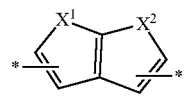
(1A-13)

(1A-14)

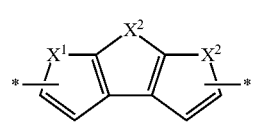
(1A-15)

In Chemical Formulas 1A-11 to 1A-15, $X^1$, $X^2$, and $X^3$ may each independently be O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a C6 to C14 aryl group, a C3 to C12 heteroaryl group, a halogen, a cyano group, or a combination thereof, and hydrogen of each heteroaromatic ring may be replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group.

In Chemical Formula 1A, $L_1$ and $L_2$ may each independently be a heteroaromatic ring group represented by one of Chemical Formulas 1A-16 to 1A-20, or a combination thereof.

[Chemical Formulas 1A-16 to 1A-20]

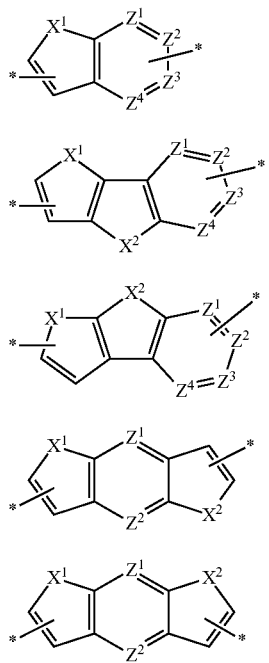

(1A-16)

(1A-17)

(1A-18)

(1A-19)

(1A-20)

In Chemical Formulas 1A-16 to 1A-20, $X^1$ and $X^2$ may each independently be O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, $Z^1$ to $Z^4$ may each independently be CR$^x$ or N, wherein R$^x$ may be hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, or a single bond, wherein in Chemical Formulas 1A-16 to 1A-18, one of $Z^1$ to $Z^4$ may be CR$^x$ wherein R$^x$ may be a single bond, and hydrogen of each aromatic ring and heteroaromatic ring may be replaced by deuterium, a halogen, a cyano group, a C1 to C10 alkyl group, a C1 to C10 alkoxy group, a C1 to C10 haloalkyl group, a —SiH$_3$ group, or a C1 to C10 alkylsilyl group.

$L_1$ and $L_2$ may each independently be a combination of a heteroaromatic ring group represented by one of Chemical Formulas 1A-11 to 1A-15 and a heteroaromatic ring group represented by one of Chemical Formulas 1A-16 to 1A-20.

In Chemical Formula 1A, Ar may be a heteroaromatic ring group represented by one of Chemical Formulas 1B-11 to 1B-15.

[Chemical Formulas 1B-11 to 1B-15]

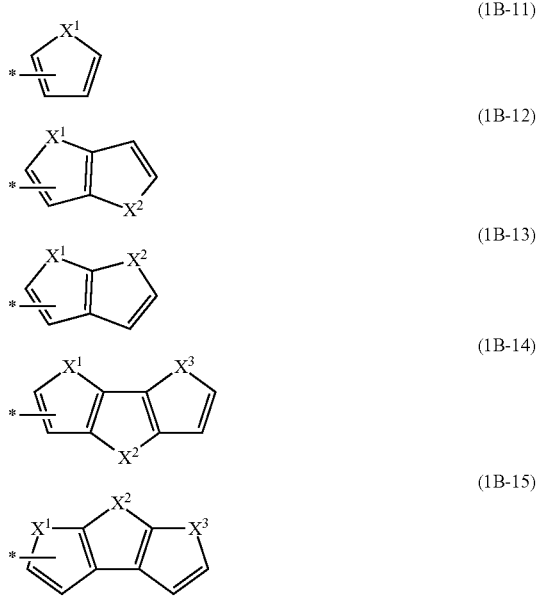

(1B-11)

(1B-12)

(1B-13)

(1B-14)

(1B-15)

In Chemical Formulas 1B-11 to 1B-15, $X^1$, $X^2$, and $X^3$ may each independently be O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a C6 to C14 aryl group, a C3 to C12 heteroaryl group, a halogen, a cyano group, or a combination thereof, and hydrogen of each heteroaromatic ring may be replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group.

In Chemical Formula 1A, Ar may be a substituted or unsubstituted C6 to C30 aryl group, a substituted or unsubstituted C2 to C30 heteroaryl group, or a fused ring thereof.

In Chemical Formula 1A, Ar may be a substituted or unsubstituted phenyl group, a substituted or unsubstituted naphthyl group, a substituted or unsubstituted acenaphthenyl group, a substituted or unsubstituted anthracenyl group, a substituted or unsubstituted phenanthrenyl group, a substituted or unsubstituted tetracenyl group, a substituted or unsubstituted pyrenyl group, a substituted or unsubstituted quinolyl group, a substituted or unsubstituted isoquinolyl group, a substituted or unsubstituted quinoxalyl group, a substituted or unsubstituted quinazolyl group, or a substituted or unsubstituted phenanthrolyl group.

In Chemical Formula 1A, Ar may be a substituted or unsubstituted C6 to C30 arylamine group, or a substituted or unsubstituted C2 to C30 heteroarylamine group, and the arylamine group or heteroarylamine group may be represented by Chemical Formula 1C-1.

[Chemical Formula 1C-1]

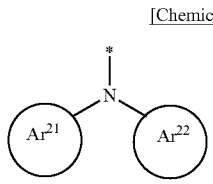

In Chemical Formula 1C-1,
$Ar^{21}$ and $Ar^{22}$ may each independently be a substituted or unsubstituted C6 to C30 aryl group or a substituted or unsubstituted C3 to C30 heteroaryl group.

Chemical Formula 1C-1 may be represented by Chemical Formula 1C-1a or Chemical Formula 1C-1 b.

[Chemical Formula 1C-1a]

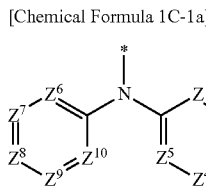

In Chemical Formula 1C-1a,
$Z^1$ to $Z^{10}$ may each independently be N or $CR^x$, wherein $R^x$ may be hydrogen, deuterium, a C1 to C10 alkyl group, a C1 to C10 haloalkyl group, a C1 to C10 alkoxy group, a $—SiH_3$ group, a C1 to C10 alkylsilyl group, a $—NH_2$ group, a C1 to C10 alkylamine group, a C6 to C12 aryl group, a C3 to C12 heteroaryl group, a halogen, a cyano group, or a combination thereof, and
when $Z^1$ to $Z^{10}$ are $CR^x$, $R^x$ of each of $Z^1$ to $Z^{10}$ is independently present or at least an adjacent two of $Z^1$ to $Z^{10}$ are linked to each other to form a 5-membered aromatic ring or a 6-membered aromatic ring,

[Chemical Formula 1C-1b]

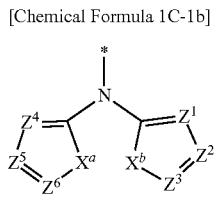

wherein, in Chemical Formula 1C-1b,
$X^a$ and $X^b$ may each independently be $—O—$, $—S—$, $—Se—$, $—Te—$, $—NR^a—$, $—SiR^bR^c—$, or $—GeR^dR^e—$, wherein $R^a$, $R^b$, $R^c$, $R^d$, and $R^e$ may each independently be hydrogen, a halogen, a substituted or unsubstituted C1 to C10 alkyl group, or a substituted or unsubstituted C6 to C10 aryl group,
$Z^1$ to $Z^6$ may each independently be N or $CR^x$, wherein $R^x$ may be hydrogen, deuterium, a C1 to C10 alkyl group, a C1 to C10 haloalkyl group, a C1 to C10 alkoxy group, a $—SiH_3$ group, a C1 to C10 alkylsilyl group, a $—NH_2$ group, a C1 to C10 alkylamine group, a C6 to C12 aryl group, a C3 to C12 heteroaryl group, a halogen, a cyano group, or a combination thereof, and
when $Z^1$ to $Z^6$ are $CR^x$, $R^x$ is independently present in each of $Z^1$ to $Z^6$ or at least an adjacent two of $Z^1$ to $Z^6$ are linked to each other to form a 5-membered aromatic ring or a 6-membered aromatic ring.

In Chemical Formula 1A, Ar may be a heteroaromatic ring group and the heteroaromatic ring group may be an N-containing heterocyclic group represented by Chemical Formula 1C-2.

[Chemical Formula 1C-2]

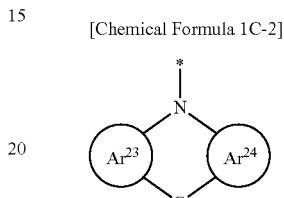

In Chemical Formula 1C-2,
$Ar^{23}$ and $Ar^{24}$ may each independently be a substituted or unsubstituted C6 to C30 arene group or a substituted or unsubstituted C3 to C15 heteroarene group,
G may be a single bond, $—O—$, $—S—$, $—Se—$, $—Te—$, $—N—$, $—NR^a—$, $—SiR^bR^c—$, $—GeR^dR^e—$, $—(CR^fR^g)_n—$, or $—(C(R^h)=C(R^i))—$, wherein $R^a$, $R^b$, $R^c$, $R^d$, $R^e$, $R^f$, $R^g$, $R^h$, and $R^i$ may each independently be hydrogen, a halogen, a substituted or unsubstituted C1 to C10 alkyl group, or a substituted or unsubstituted C6 to C10 aryl group, wherein $R^b$, $R^c$, $R^d$, $R^e$, $R^f$, $R^g$, $R^h$, and $R^i$ may each independently be present or $R^b$ and $R^c$, $R^d$ and $R^e$, $R^f$ and $R^g$, or $R^h$ and $R^i$ may be linked to each other to provide a ring, and n of $—(CR^fR^g)_n—$ may be 1 or 2.

Chemical Formula 1C-2 may be represented by Chemical Formula 1C-2a, Chemical Formula 1C-2b or Chemical Formula 1C-2c:

[Chemical Formula 1C-2a]

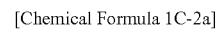

In Chemical Formula 1C-2a,
G may be a single bond, $—O—$, $—S—$, $—Se—$, $—Te—$, $—N—$, $—NR^a—$, $—SiR^bR^c—$, $—GeR^dR^e—$, $—(CR^fR^g)_n—$, or $—(C(R^h)=C(R^i))—$, wherein $R^a$, $R^b$, $R^c$, $R^d$, $R^e$, $R^f$, $R^g$, $R^h$, and $R^i$ may each independently be hydrogen, a halogen, a substituted or unsubstituted C1 to C10 alkyl group, or a substituted or unsubstituted C6 to C10 aryl group, wherein $R^b$, $R^c$, $R^d$, $R^e$, $R^f$, $R^g$, $R^h$, and $R^i$ may each independently be present or $R^b$ and $R^c$, $R^d$ and $R^e$, $R^f$ and $R^g$, or $R^h$ and $R^i$ may be linked to each other to provide a ring, and n of $—(CR^fR^g)_n—$ may be 1 or 2,
$Z^1$ to $Z^8$ may each independently be N or $CR^x$, wherein $R^x$ may be hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when $Z^1$ to $Z^8$ are CR$^x$, R$^x$ of each of $Z^1$ to $Z^8$ is independently present or at least adjacent two of $Z^1$ to $Z^8$ are linked to each other to form a 5-membered aromatic ring or a 6-membered aromatic ring,

[Chemical Formula 1C-2b]

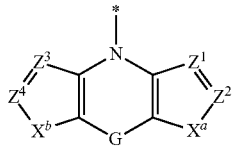

[Chemical Formula 1C-2c]

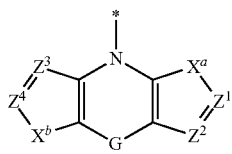

In Chemical Formulas 1C-2b and 1C-2c,

G may be a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ may each independently be present or R$^b$ and R$^c$, R$^d$ and R$^e$, R$^f$ and R$^g$, or R$^h$ and R$^i$ may be linked to each other to provide a ring, and n of —(CR$^f$R$^g$)$_n$— may be 1 or 2, X$^a$ and X$^b$ may each independently be —O—, —S—, —Se—, —Te—, —NR$^p$—, —SiR$^p$R$^r$—, or —GeR$^s$R$^t$—, wherein R$^p$, R$^q$, R$^r$, R$^s$, and R$^t$ may each independently be hydrogen, a halogen, a substituted or unsubstituted C1 to C10 alkyl group, or a substituted or unsubstituted C6 to C10 aryl group, $Z^1$ to $Z^4$ may each independently be N or CR$^x$, wherein R$^x$ may be hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when $Z^1$ to $Z^4$ are CR$^x$, R$^x$ of each of $Z^1$ to $Z^4$ is independently present or at least an adjacent two of $Z^1$ to $Z^4$ are linked to each other to form a 5-membered aromatic ring or a 6-membered aromatic ring.

In Chemical Formula 1A, Ar may be an aromatic ring or heteroaromatic ring group represented by one of Chemical Formulas 1B-16 to 1B-25.

[Chemical Formulas 1B-16 to 1B-25]

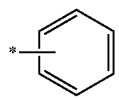
(1B-16)

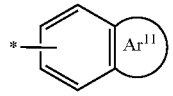
(1B-17)

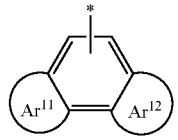
(1B-18)

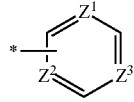
(1B-19)

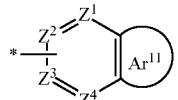
(1B-20)

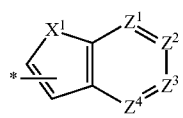
(1B-21)

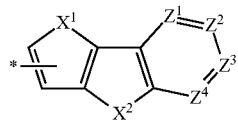
(1B-22)

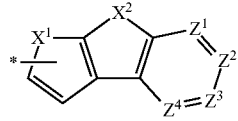
(1B-23)

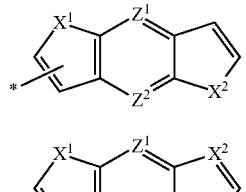
(1B-24)

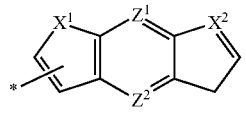
(1B-25)

In Chemical Formulas 1B-16 to 1B-25,

X$^1$ and X$^2$ may each independently be O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, $Z^1$ to $Z^4$ may each independently be CR$^x$ or N, wherein R$^x$ may be hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, or a single bond, wherein in Chemical Formula 1B-20, one of $Z^1$ to $Z^4$ may be $CR^x$ wherein $R^x$ may be a single bond, $Ar^{11}$ and $Ar^{12}$ may each independently be a substituted or unsubstituted C6 to C30 arene group or a substituted or unsubstituted C3 to C30 heteroarene group, and hydrogen of each aromatic ring and heteroaromatic ring may be replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group.

The aromatic ring or heteroaromatic ring group represented by Chemical Formulas 1B-16 to 1B-25 may be substituted with an arylamine group, and the arylamine group may be represented by Chemical Formula 1C-1. Chemical Formula 1C-1 may be represented by Chemical Formula 1C-1a or Chemical Formula 1C-1b.

The aromatic ring or heteroaromatic ring group represented by one of Chemical Formulas 1B-16 to 1B-25 may be substituted with an N-containing heterocyclic group, and the N-containing heterocyclic group may be represented by Chemical Formula 1C-2. Chemical Formula 1C-2 may be represented by Chemical Formula 1C-2a, Chemical Formula 1C-2b, or Chemical Formula 1C-2c.

In Chemical Formula 1, at least one of $R^{11a}$, $R^{11b}$, $R^{11c}$, $R^{12a}$, $R^{12b}$, or $R^{12c}$ may be the functional group represented by Chemical Formula 1A, and at least one of $R^{13a}$, $R^{13b}$, $R^{13c}$, $R^{14a}$, $R^{14b}$, or $R^{14c}$ may be the functional group represented by Chemical Formula 1A.

In some example embodiments, at least one of $R^{11a}$, $R^{11b}$, or $R^{11c}$ may be the functional group represented by Chemical Formula 1A, and at least one of $R^{13a}$, $R^{13b}$, or $R^{13c}$ may be the functional group represented by Chemical Formula 1A.

In some example embodiments, at least one of $R^{12a}$, $R^{12b}$, or $R^{12c}$ may be the functional group represented by Chemical Formula 1A, and at least one of $R^{14a}$, $R^{14b}$, or $R^{14c}$ may be the functional group represented by Chemical Formula 1A.

In some example embodiments, $R^{11a}$ and $R^{13a}$ may be the functional group represented by Chemical Formula 1A.

In some example embodiments, $R^{12a}$ and $R^{14a}$ may be the functional group represented by Chemical Formula 1A.

According to some example embodiments, an infrared absorber including the compound is provided.

According to some example embodiments, a composition including the compound is provided.

The infrared absorber may exhibit a peak absorption wavelength in a wavelength range of about 750 nm to about 3000 nm.

According to some example embodiments, an infrared absorbing/blocking film including the compound is provided.

According to some example embodiments, a photoelectric device includes a first electrode and a second electrode facing each other, and a photoactive layer between the first electrode and the second electrode, wherein the photoactive layer includes the aforementioned compound represented by Chemical Formula 1.

According to some example embodiments, a sensor including the photoelectric device is provided.

According to some example embodiments, an electronic device including the photoelectric device or the sensor is provided.

According to some example embodiments, the photoactive layer further includes fullerene or a fullerene derivative.

According to some example embodiments, the photoactive layer has a peak absorption wavelength in a wavelength region of about 750 nm to about 3000 nm. The peak absorption wavelength may be in a wavelength region of about 1000 nm to about 3000 nm. The peak absorption wavelength may be in a wavelength region of about 1060 nm to about 1350 nm.

According to some example embodiments, the photoactive layer has an energy bandgap between about 0.99 eV and about 1.40 eV. The energy bandgap may be between about 0.99 eV and about 1.18 eV.

According to some example embodiments, a photoelectric device may include a first electrode and a second electrode facing each other, a photoactive layer between the first electrode and the second electrode, and a charge auxiliary layer between the photoactive layer and the first electrode, or the photoactive layer and the second electrode. At least one of the first electrode, the second electrode, the photoactive layer, or the charge auxiliary layer may include the aforementioned compound represented by Chemical Formula 1.

The charge auxiliary layer may include the compound and the photoactive layer, the first electrode, and the second electrode may not include the compound.

The photoactive layer may include the compound and the charge auxiliary layer, the first electrode, and the second electrode may not include the compound.

The photoelectric device may further include a plurality of charge auxiliary layers, the plurality of charge auxiliary layers including the charge auxiliary layer, the plurality of charge auxiliary layers including a first charge auxiliary layer between the photoactive layer and the first electrode, and a second charge auxiliary layer between the photoactive layer and the second electrode. At least one of the first electrode, the second electrode, the photoactive layer, the first charge auxiliary layer, or the second charge auxiliary layer may include the compound.

A sensor may include the photoelectric device. An electronic device may include the sensor.

According to some example embodiments, an image sensor may include a semiconductor substrate, a first photoelectric device on the semiconductor substrate, the first photoelectric device configured to selectively absorb light in a first infrared wavelength region, and an additional sensor configured to selectively absorb light in a separate wavelength region that is different from the first infrared wavelength region. The first photoelectric device may include the aforementioned compound represented by Chemical Formula 1.

The additional sensor may be an infrared light sensor at least partially embedded within the semiconductor substrate, and the separate wavelength region may be a separate infrared wavelength region that is different from the first infrared wavelength region. The first photoelectric device and the infrared light sensor may overlap in a vertical direction that is perpendicular to an upper surface of the semiconductor substrate.

The additional sensor may include a plurality of photodiodes at least partially embedded within the semiconductor substrate, the plurality of photodiodes configured to selectively absorb light in separate visible wavelength regions, and the first photoelectric device and the plurality of photodiodes may overlap in the vertical direction that is perpendicular to the upper surface of the semiconductor substrate.

The additional sensor may include at least one additional photoelectric device vertically stacked between the first photoelectric device and the semiconductor substrate. Each separate photoelectric device of the at least one additional photoelectric device may include a separate photoelectric conversion layer and may be configured to selectively absorb light in a separate, respective wavelength region that is different from the first infrared wavelength region.

The first photoelectric device may include a first electrode and a second electrode facing each other, and a photoactive layer between the first electrode and the second electrode, wherein the photoactive layer includes the compound.

The first photoelectric device may include a first electrode and a second electrode facing each other, a photoactive layer between the first electrode and the second electrode, and a charge auxiliary layer between the photoactive layer and the first electrode or the photoactive layer and the second electrode. At least one of the first electrode, the second electrode, the photoactive layer, or the charge auxiliary layer may include the compound.

An electronic device may include the image sensor.

The compound exhibits good light absorption characteristics in the infrared region, and thus may be effectively used for photoelectric devices and/or organic sensors.

DETAILED DESCRIPTION

Figure 1:
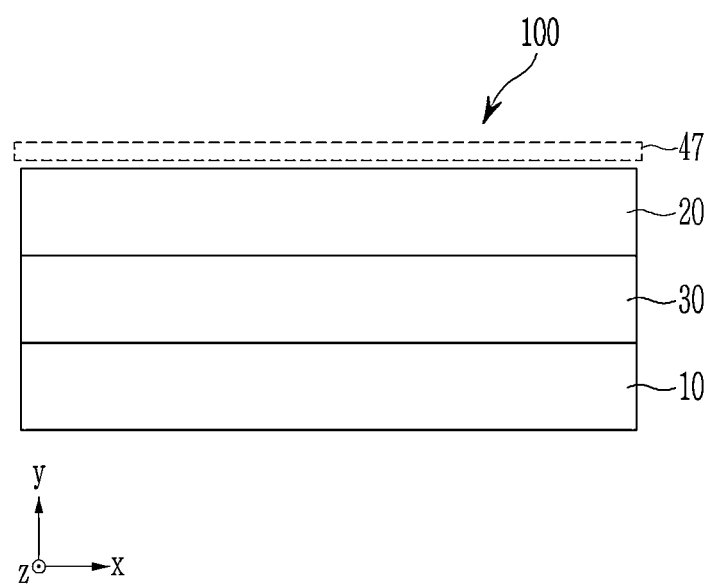
FIG. 1 is a cross-sectional view showing a photoelectric device according to some example embodiments.

Hereinafter, example embodiments will hereinafter be described in detail, and may be easily performed by a person having an ordinary skill in the related art.

However, this disclosure may be embodied in many different forms and is not to be construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present. It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

When the terms "about" or "substantially" are used in this specification in connection with a numerical value, it is intended that the associated numerical value include a tolerance of ±10% around the stated numerical value. When ranges are specified, the range includes all values therebetween such as increments of 0.1%.

In the drawings, parts having no relationship with the description are omitted for clarity of some example embodiments, and the same or similar constituent elements are indicated by the same reference numeral throughout the specification.

Hereinafter, "combination" includes a mixture of two or more, inter-substitution, and a laminate structure of two or more.

As used herein, when specific definition is not otherwise provided, "substituted" refers to replacement of a hydrogen of a compound or a functional group by a substituent selected from a halogen, a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid group or a salt thereof, a silyl group, a C1 to C20 alkyl group, a C2 to C20 alkenyl group, a C2 to C20 alkynyl group, a C6 to C30 aryl group, a C7 to C30 arylalkyl group, a C1 to C30 alkoxy group, a C1 to C20 heteroalkyl group, a C3 to C20 heteroaryl group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, and a combination thereof.

As used herein, when specific definition is not otherwise provided, "hetero" refers to one including 1 to 4 heteroatoms selected from N, O, S, Se, Te, Si, and P.

As used herein, when a definition is not otherwise provided, "aromatic ring" refers to a functional group in which all atoms in the cyclic functional group have a p-orbital, and wherein these p-orbitals are conjugated and "heteroaromatic ring" refers to the aromatic ring including a heteroatom. The "aromatic ring" refers to a C6 to C30 arene group, for example a C6 to C20 arene group or a C6 to C30 aryl group, for example a C6 to C20 aryl group. The "heteroaromatic ring" refers to a C3 to C30 heteroarene group, for example a C3 to C20 heteroarene group or a C3 to C30 heteroaryl group, for example a C3 to C20 heteroaryl group.

As used herein, "arene group" refers to a hydrocarbon group having an aromatic ring, and includes monocyclic and polycyclic hydrocarbon groups, and the additional ring of the polycyclic hydrocarbon group may be an aromatic ring or a nonaromatic ring. The heteroarene group means an arene group including 1 to 3 heteroatoms selected from N, O, S, Se, Te, P, and Si in the ring.

As used herein, when a definition is not otherwise provided, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like; a group in which two or more hydrocarbon aromatic moieties may be linked by a sigma bond, for example a biphenyl group, a terphenyl group, a quarterphenyl group, and the like; and a group in which two or more hydrocarbon aromatic moieties are fused directly or indirectly to provide a non-aromatic fused ring, for example a fluorenyl group. The aryl group may include a monocyclic, polycyclic or fused polycyclic (i.e., rings sharing adjacent pairs of carbon atoms) functional group.

As used herein, when a definition is not otherwise provided, "heteroaryl group" refers to an aryl group including at least one heteroatom selected from N, O, S, Se, Te, P, and Si instead of carbon (C) in the ring. When the heteroaryl group is a fused ring, at least one of the rings of the heteroaryl group may have a heteroatom or each ring may have a heteroatom.

As used herein, when a definition is not otherwise provided, "ring" refers to an aromatic ring, a non-aromatic ring, a heteroaromatic ring, a hetero non-aromatic ring, a fused ring thereof, and/or a combination thereof. The aromatic ring are the same as described above and the non-aromatic ring may be a C3 to C30 cycloalkyl group, a C3 to C30 cycloalkenyl group, or a C3 to C30 cycloalkynyl group.

As used herein, when a definition is not otherwise provided, "halogen" may be one of F, Cl, Br, or I and the haloalkyl group may be an alkyl group in which at least one hydrogen is replaced by a halogen and may be, for example, a perfluoroalkyl group such as —CF$_3$.

As used herein, when a definition is not otherwise provided, in the substituted or unsubstituted alkylene group, "substituted alkylene group" may include an alkylene group in which at least one hydrogen is replaced by the substituent or at least one methylene group is replaced by —O—, —C(=O)—, —OC(=O)—, or —C(=O)O—.

As used herein, when a definition is not otherwise provided, "cyano-containing group" refers to a monovalent group such as a C1 to C30 alkyl group, a C2 to C30 alkenyl group, or a C2 to C30 alkynyl group where at least one hydrogen is replaced by a cyano group. The cyano-containing group also refers to a divalent group such as =CR$^{x'}$—(CR$^x$R$^y$)$_p$—CR$^{y'}$(CN)$_2$ wherein R$^x$, R$^y$, R$^{x'}$, and R$^{y'}$ are independently hydrogen or a C1 to C10 alkyl group and p may be an integer of 0 to 10 (or 1 to 10). Specific examples of the cyano-containing group may be a dicyanomethyl group, a dicyanovinyl group, a cyanoethynyl group, and the like.

As used herein, when a definition is not otherwise provided, the "infrared wavelength region" includes a near-infrared/infrared wavelength region with a wavelength region of about 750 nm to about 3000 nm.

Hereinafter, a compound according to some example embodiments is described. In some example embodiments, a composition may include the compound. The compound is represented by Chemical Formula 1.

[Chemical Formula 1]

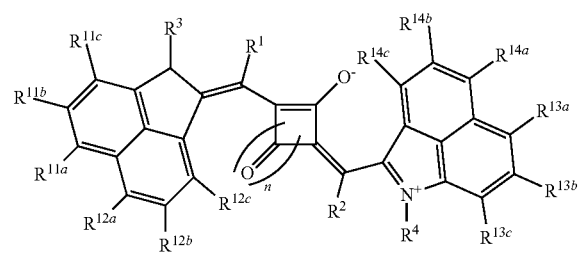

In Chemical Formula 1, $R^1$ to $R^4$ may each independently be hydrogen, deuterium, a C1 to C10 alkyl group, a C1 to C10 alkoxy group, a C1 to C10 haloalkyl group, a C6 to C14 aryl group, or a C3 to C12 heteroaryl group, $R^{11a}$ to $R^{14c}$ may each independently be hydrogen, deuterium, a halogen, a cyano group, a C1 to C10 alkyl group, a C1 to C10 alkoxy group, a C1 to C10 haloalkyl group, a C6 to C14 aryl group, a C6 to C14 aryloxy group, a C3 to C12 heteroaryl group, or a functional group represented by Chemical Formula 1A, provided that (e.g., wherein) at least one of $R^{11a}$ to $R^{14c}$ is a functional group represented by Chemical Formula 1A, wherein $R^{11a}$ to $R^{14c}$ may be present independently of each other or two adjacent functional groups (e.g., an adjacent two of $R^{11a}$ to $R^{14c}$, an adjacent two functional groups of $R^{11a}$ to $R^{14c}$, etc.) may be linked to each other to form a fused ring with benzoindole, and n may be an integer of 1 or 2, $$*\text{-}L_1\text{-}(L_2)_m\text{-}Ar \qquad [\text{Chemical Formula 1A}]$$

wherein, in Chemical Formula 1A, $L_1$ may be a substituted or unsubstituted C2 to C15 heteroaromatic ring group, $L_2$ may be a substituted or unsubstituted C2 to C15 heteroaromatic ring group, a substituted or unsubstituted C6 to C30 aromatic ring group, a substituted or unsubstituted C1 to C10 alkylene group, or a substituted or unsubstituted C3 to C20 cycloalkylene group, Ar may be a substituted or unsubstituted C6 to C30 aromatic ring group, a substituted or unsubstituted C2 to C30 heteroaromatic ring group, a fused ring thereof (e.g., a fused ring of a substituted or unsubstituted C6 to C30 aromatic ring group, and/or a substituted or unsubstituted C2 to C30 heteroaromatic ring group), a substituted or unsubstituted C6 to C30 arylamine group, or a substituted or unsubstituted C2 to C30 heteroarylamine group, and m may be 0, 1, or 2.

A material absorbing long-wavelength light such as infrared light is required to have a small HOMO-LUMO bandgap energy. The small bandgap energy may be secured by lengthening a conjugation length, but when the conjugation length is increased, a film forming process may be difficult to apply. The compound represented by Chemical Formula 1 includes electron-donating benzoindol (benzo[cd]indole) moieties that are linked to a core (squaraine (SQ) or croconaine (CR) in Chemical Formula 1) of a conjugated structure having electron-accepting characteristics and the moiety includes a functional group represented by Chemical Formula 1A. The compound has a donor-acceptor-donor (D-A-D) structure and thus excellent photoelectric conversion efficiency and charge transfer characteristics and small bandgap energy and accordingly, may effectively absorb light in a near infrared/infrared wavelength region (e.g., a long wavelength region of about 750 nm to about 3000 nm and particularly, greater than or equal to about 1000 nm and less than or equal to about 3000 nm). The functional group represented by Chemical Formula 1A may shift an absorption wavelength of the compound represented by Chemical Formula 1 toward the long wavelength and increase an extinction coefficient. The functional group represented by Chemical Formula 1A may easily tune a bandgap of the compound represented by Chemical Formula 1 through various combinations of $L_1$, $L_2$, and Ar.

Hereinafter, a bandgap energy (also referred to interchangeably as an energy bandgap) of a compound, film, layer or the like refers to an absolute value of a difference between the HOMO energy level and LUMO energy level of the compound, film, layer or the like.

As shown in Table 2 below, in some example embodiments, the bandgap energy of the compound represented by Chemical Formula 1, or a layer, film, or the like including the compound, may be between about 0.99 eV and about 1.40 eV.

As shown in Table 2 below, in some example embodiments, the bandgap energy of the compound represented by Chemical Formula 1, or a layer, film, or the like including the compound, may be between about 0.99 eV and about 1.18 eV.

The functional group represented by Chemical Formula 1A includes a heteroaromatic ring group ($L_1$ and optionally, $L_2$) and a (hetero)aromatic ring group (Ar) and thus may shift the absorption wavelength of the compound represented by Chemical Formula 1 toward the long wavelength and increase the extinction coefficient.

In Chemical Formula 1A, $L_1$ and $L_2$ may be the same or different, and may each independently be a heteroaromatic ring group, and Ar may be a substituted or unsubstituted C6 to C30 aromatic ring group, a substituted or unsubstituted C2 to C30 heteroaromatic ring group, a fused ring thereof, a substituted or unsubstituted C6 to C30 arylamine group, or a substituted or unsubstituted C2 to C30 heteroarylamine group.

In Chemical Formula 1A, $L_1$ and $L_2$ may each independently be a heteroaromatic ring group represented by one of Chemical Formulas 1A-11 to 1A-15, or a combination thereof. Herein, "the combination thereof" means that two or more heteroaromatic ring groups selected from Chemical Formulas 1A-11 to 1A-15 are linked by a single bond or a substituted or unsubstituted C1 to C6 alkylene group (e.g., a methylene group).

[Chemical Formulas 1A-11 to 1A-15]

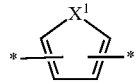

(1A-11)

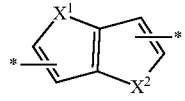

(1A-12)

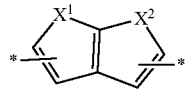

(1A-13)

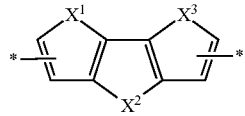

(1A-14)

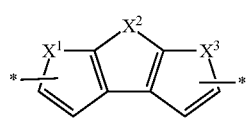

(1A-15)

In Chemical Formulas 1A-11 to 1A-15, $X^1$, $X^2$, and $X^3$ may each independently be O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a C6 to C14 aryl group, a C3 to C12 heteroaryl group, a halogen, a cyano group, or a combination thereof, and hydrogen of each heteroaromatic ring may be replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH₃ group, or a C1 to C10 alkylsilyl group.

In Chemical Formula 1A, $L_1$ and $L_2$ may each independently be a heteroaromatic ring group represented by one of Chemical Formulas 1A-16 to 1A-20, or a combination thereof. Herein, "the combination thereof" means that two or more heteroaromatic ring groups selected from Chemical Formulas 1A-16 to 1A-20 are linked by a single bond or a substituted or unsubstituted C1 to C6 alkylene group (e.g., a methylene group).

[Chemical Formulas 1A-16 to 1A-20]

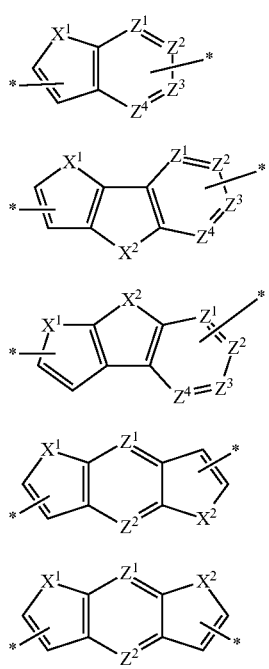

In Chemical Formulas 1A-16 to 1A-20

$X^1$ and $X^2$ may each independently be O, S, Se, Te, S(=O), S(=O)₂, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a —SiH₃ group, a C1 to C10 alkylsilyl group, a —NH₂ group, a C1 to C10 alkylamine group, a C6 to C10 arylamine group, a C6 to C14 aryl group, a C3 to C12 heteroaryl group, a halogen, a cyano group, or a combination thereof, $Z^1$ to $Z^4$ may each independently be CR$^x$ or N, wherein R$^x$ may be hydrogen, deuterium, a C1 to C10 alkyl group, a C1 to C10 haloalkyl group, a —SiH₃ group, a C1 to C10 alkylsilyl group, a —NH₂ group, a C1 to C10 alkylamine group, a C6 to C14 aryl group, a C3 to C12 heteroaryl group, a halogen, a cyano group, or a combination thereof, or a single bond, provided that (e.g., wherein) in Chemical Formulas 1A-16 to 1A-18, one of $Z^1$ to $Z^4$ may be CR$^x$ wherein R$^x$ may be a single bond, and hydrogen of each aromatic ring and heteroaromatic ring may be replaced by deuterium, a halogen, a cyano group, a C1 to C10 alkyl group, a C1 to C10 alkoxy group, a C1 to C10 haloalkyl group, a —SiH₃ group, or a C1 to C10 alkylsilyl group.

Each of $L_1$ and $L_2$ may be independently a combination of the heteroaromatic ring group represented by one of Chemical Formulas 1A-11 to 1A-15 and the heteroaromatic ring group represented by one of Chemical Formulas 1A-16 to 1A-20. Herein, "the combination thereof" means that the heteroaromatic ring group represented by one of Chemical Formulas 1A-11 to 1A-15 and the heteroaromatic ring group represented by one of Chemical Formulas 1A-16 to 1A-20 are linked by a single bond or a substituted or unsubstituted C1 to C6 alkylene group (e.g., a methylene group).

In Chemical Formula 1A, Ar may be a heteroaromatic ring group represented by one of Chemical Formulas 1B-11 to 1B-15.

[Chemical Formulas 1B-11 to 1B-15]

 (1B-11)

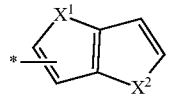 (1B-12)

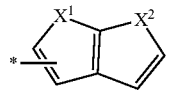 (1B-13)

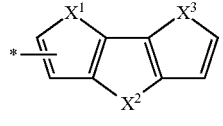 (1B-14)

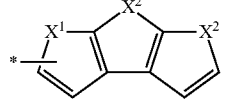 (1B-15)

In Chemical Formulas 1B-11 to 1B-15, $X^1$, $X^2$, and $X^3$ may each independently be O, S, Se, Te, S(=O), S(=O)₂, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a C6 to C14 aryl group, a C3 to C12 heteroaryl group, a halogen, a cyano group, or a combination thereof, and hydrogen of each heteroaromatic ring may be replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH₃ group, or a C1 to C10 alkylsilyl group.

In Chemical Formula 1A, Ar may be a substituted or unsubstituted C6 to C30 aryl group, a substituted or unsubstituted C2 to C15 heteroaryl group, or a fused ring thereof.

In Chemical Formula 1A, Ar may be a substituted or unsubstituted phenyl group, a substituted or unsubstituted naphthyl group, a substituted or unsubstituted acenaphthenyl group, a substituted or unsubstituted anthracenyl group, a substituted or unsubstituted phenanthrenyl group, a substituted or unsubstituted tetracenyl group, a substituted or unsubstituted pyrenyl group, a substituted or unsubstituted quinolyl group, a substituted or unsubstituted isoquinolyl group, a substituted or unsubstituted quinoxalyl group, a substituted or unsubstituted quinazolyl group, or a substituted or unsubstituted phenanthrolyl group. In some example embodiments, the substituent of Ar may be a halogen or a C1 to C30 alkoxy group.

In Chemical Formula 1A, Ar may be a C6 to C30 aryl group substituted with an arylamine group, a C2 to C15 heteroaryl group substituted with an arylamine group, or a fused ring thereof, and the arylamine group may be represented by Chemical Formula 1C-1.

[Chemical Formula 1C-1]

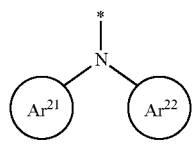

In Chemical Formula 1C-1, $Ar^{21}$ and $Ar^{22}$ may each independently be a substituted or unsubstituted C6 to C30 aryl group or a substituted or unsubstituted C3 to C30 heteroaryl group.

Chemical Formula 1C-1 may be represented by Chemical Formula 1C-1a.

[Chemical Formula 1C-1a]

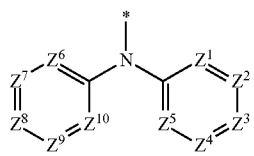

In Chemical Formula 1C-1a, $Z^1$ to $Z^{10}$ may each independently be N or $CR^x$, wherein $R^x$ may be hydrogen, deuterium, a C1 to C10 alkyl group, a C1 to C10 haloalkyl group, a C1 to C10 alkoxy group, a —$SiH_3$ group, a C1 to C10 alkylsilyl group, a —$NH_2$ group, a C1 to C10 alkylamine group, a C6 to C12 aryl group, a C3 to C12 heteroaryl group, a halogen, a cyano group, or a combination thereof, and when $Z^1$ to $Z^{10}$ are $CR^x$, $R^x$ of each of $Z^1$ to $Z^{10}$ may independently be present or at least an adjacent two of $Z^1$ to $Z^{10}$ (e.g., some or all adjacent pairs of $Z^1$ to $Z^{10}$) may be linked to each other to form a 5-membered aromatic ring or a 6-membered aromatic ring.

In some example embodiments, at least one of $Z^2$ to $Z^4$ and at least one of $Z^7$ to $Z^9$ in Chemical Formula 1C-1a may be $CR^x$ wherein $R^x$ may be a C1 to C10 haloalkyl group or a C1 to C10 alkoxy group.

In some example embodiments, $Z^3$ and $Z^8$ in Chemical Formula 1C-1a may be $CR^x$ and $R^x$ may be a C1 to C10 haloalkyl group or a C1 to C10 alkoxy group.

Chemical Formula 1C-1a may be represented by Chemical Formulas 1C-1a-1 to 1C-1a-12.

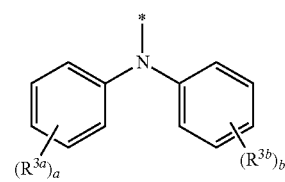
(1C-1a-1)

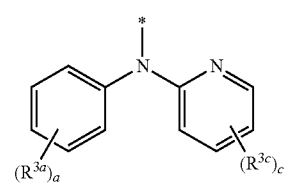
(1C-1a-2)

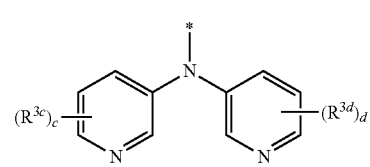
(1C-1a-3)

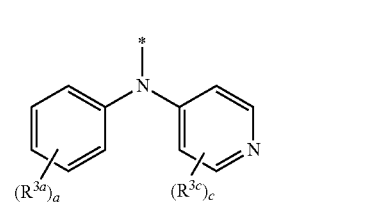
(1C-1a-4)

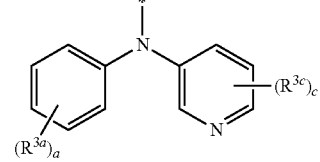
(1C-1a-5)

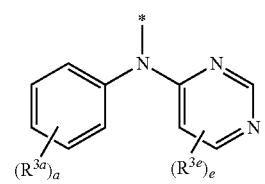
(1C-1a-6)

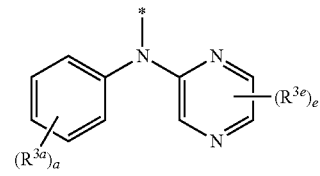
(1C-1a-7)

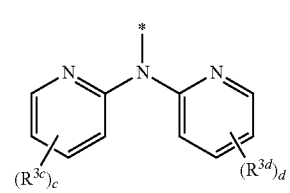
(1C-1a-8)

-continued (1C-1a-9)
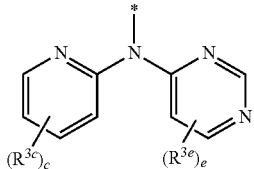

(1C-1a-10)
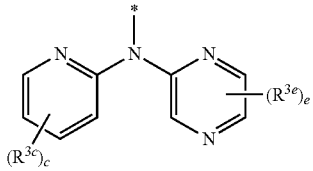

(1C-1a-11)
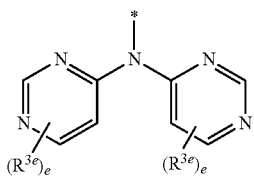

(1C-1a-12)
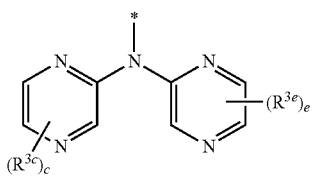

In Chemical Formulas 1C-1a-1 to 1C-1a-12,
a and b may each independently be an integer of 1 to 5,
c and d may each independently be an integer of 1 to 4
e may be an integer of 1 to 3,
$R^{3a}$ to $R^e$ may independently be hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, when a, b, c, d, and e are 2 or more, two adjacent to each other of a plurality of $R^{3a}$'s, two adjacent to each other of a plurality of $R^{3b}$'s, two adjacent to each other of a plurality of $R^{3c}$'s, two adjacent to each other of a plurality of $R^{3d}$'s, or two adjacent to each other of a plurality of $R^{3e}$'s may be linked to each other to provide a 5-membered aromatic ring or a 6-membered aromatic ring.

In some example embodiments, Chemical Formula 1C-1 may be represented by Chemical Formula 1C-1 b.

[Chemical Formula 1C-1b]
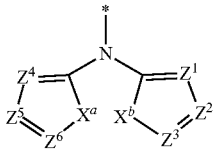

In Chemical Formula 1C-1b,
$X^a$ and $X^b$ may each independently be —O—, —S—, —Se—, —Te—, —$NR^a$—, —$SiR^bR^c$—, or —$GeR^d$ $R^e$—, wherein $R^a$, $R^b$, $R^c$, $R^d$, and $R^e$ may each independently be hydrogen, a halogen, a substituted or unsubstituted C1 to C10 alkyl group, or a substituted or unsubstituted C6 to C10 aryl group, $Z^1$ to $Z^6$ may each independently be N or $CR^x$, wherein $R^x$ may be hydrogen, deuterium, a C1 to C10 alkyl group, a C1 to C10 haloalkyl group, a C1 to C10 alkoxy group, a —$SiH_3$ group, a C1 to C10 alkylsilyl group, a —$NH_2$ group, a C1 to C10 alkylamine group, a C6 to C12 aryl group, a C3 to C12 heteroaryl group, a halogen, a cyano group, or a combination thereof, and when $Z^1$ to $Z^6$ are $CR^x$, $R^x$ of each of $Z^1$ to $Z^6$ may independently be present (e.g., $Z^1$ to $Z^6$ may not be linked to each other) or at least an adjacent two of $Z^1$ to $Z^6$ (e.g., some or all adjacent pairs of $Z^1$ to $Z^6$) may be linked to each other to form a 5-membered aromatic ring or a 6-membered aromatic ring.

In some example embodiments, at least one of $Z^1$ to $Z^3$ and at least one of $Z^4$ to $Z^6$ in Chemical Formula 1C-1 b may be $CR^x$ and $R^x$ may be a C1 to C10 haloalkyl group or a C1 to C10 alkoxy group.

In some example embodiments, $Z^2$ and $Z^5$ in Chemical Formula 1C-1b may be $CR^x$ wherein $R^x$ may be a C1 to C10 haloalkyl group or a C1 to C10 alkoxy group.

In Chemical Formula 1A, Ar may be a C6 to C30 aryl group substituted with an N-containing heterocyclic group, a C2 to C15 heteroaryl group substituted with an N-containing heterocyclic group, or a fused ring thereof, and the N-containing heterocyclic group may be represented by Chemical Formula 1C-2.

[Chemical Formula 1C-2]
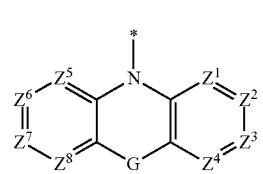

In Chemical Formula 1C-2,
$Ar^{23}$ and $Ar^{24}$ may each independently be a substituted or unsubstituted C6 to C30 arene group or a substituted or unsubstituted C3 to C15 heteroarene group, G may be a single bond, —O—, —S—, —Se—, —Te—, —N—, —$NR^a$—, —$SiR^bR^c$—, —$GeR^dR^e$—, —$(CR^f R^g)_n$—, or —$(C(R^h)=C(R^i))$—, wherein $R^a$, $R^b$, $R^c$, $R^d$, $R^e$, $R^f$, $R^g$, $R^h$, and $R^i$ may each independently be hydrogen, a halogen, a substituted or unsubstituted C1 to C10 alkyl group, or a substituted or unsubstituted C6 to C10 aryl group, wherein $R^b$, $R^c$, $R^d$, $R^e$, $R^f$, $R^g$, $R^h$, and $R^i$ may each independently be present (e.g., may be not linked to each other to provide a ring) or $R^b$ and $R^c$, $R^d$ and $R^e$, $R^f$ and $R^g$, or $R^h$ and $R^i$ may be linked to each other to provide a ring, and n of —$(CR^fR^g)_n$— may be 1 or 2.

Chemical Formula 1C-2 may be represented by Chemical Formula 1C-2a:

[Chemical Formula 1C-2a]

In Chemical Formula 1C-2a,

G may be a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ may each independently be present (e.g., may be not linked to each other to provide a ring) or R$^b$ and R$^c$, R$^d$ and R$^e$, R$^f$ and R$^g$, or R$^h$ and R$^i$ may be linked to each other to provide a ring, and n of —(CR$^f$R$^g$)$_n$— may be 1 or 2, Z$^1$ to Z$^8$ may each independently be N or CR$^x$, wherein R$^x$ may be hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when Z$^1$ to Z$^8$ are CR$^x$, R$^x$ of each of Z$^1$ to Z$^8$ may independently be present (e.g., Z$^1$ to Z$^8$ may not be linked to each other to form a ring) or at least adjacent two of Z$^1$ to Z$^8$ may be linked to each other to form a 5-membered aromatic ring or a 6-membered aromatic ring.

In some example embodiments, at least one of Z$^2$ to Z$^4$ and at least one of Z$^6$ to Z$^8$ in Chemical Formula 1C-2a may be CR$^x$ wherein R$^x$ may be a C1 to C10 haloalkyl group or a C1 to C10 alkoxy group.

In some example embodiments, in Chemical Formula 1C-2a, Z$^3$ and Z$^7$ may be CR$^x$ wherein R$^x$ may be a C1 to C10 haloalkyl group or a C1 to C10 alkoxy group.

According to some example embodiments, in Chemical Formula 1C-2a, at least one of Z$^1$ to Z$^4$ and/or at least one of Z$^5$ to Z$^8$ may be N. According to some example embodiments, in Chemical Formula 1C-2a, at least two of Z$^1$ to Z$^4$ and/or at least two of Z$^5$ to Z$^8$ may be N.

Chemical Formula 1C-2a may be represented by any one of Chemical Formulas 1C-2a-1 to 1C-2a-12.

(1C-2a-1)

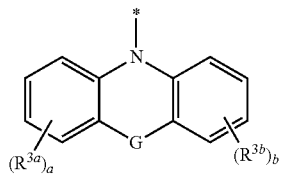

(1C-2a-2)

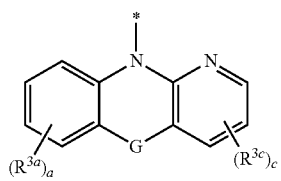

(1C-2a-3)

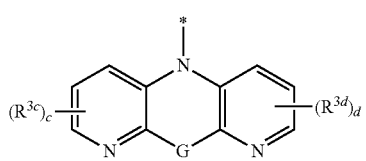

(1C-2a-4)

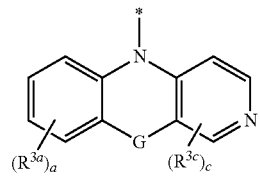

(1C-2a-5)

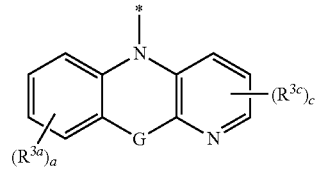

(1C-2a-6)

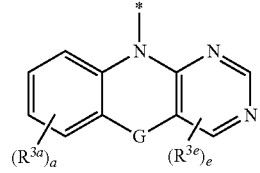

(1C-2a-7)

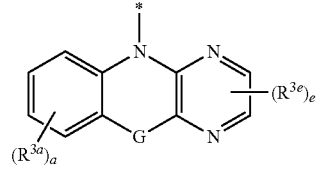

(1C-2a-8)

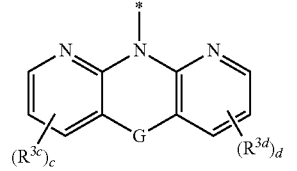

(1C-2a-9)

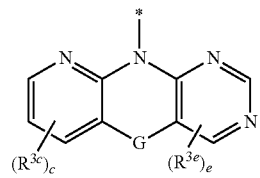

(1C-2a-10)

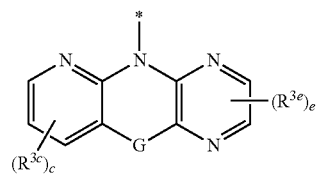

(1C-2a-11)

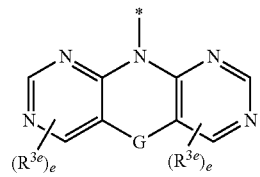

-continued

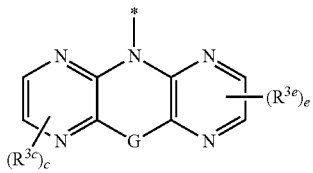

[Chemical Formula 1C-2a-12]

In Chemical Formulas 1C-2a-1 to 1C-2a-12, a and b may each independently be an integer of 1 to 4, c and d may each independently be an integer of 1 to 3, e is an integer of 1 or 2, G may be a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ may each independently be present (e.g., may not be linked to each other to provide a ring) or R$^b$ and R$^c$, R$^d$ and R$^e$, R$^f$ and R$^g$, or R$^h$ and R$^i$ may be linked to each other to provide a ring, and n of —(CR$^f$R$^g$)$_n$— may be 1 or 2, and R$^{3a}$ to R$^{3e}$ may independently be hydrogen, a substituted or unsubstituted C1 to C30 alkyl group, a substituted or unsubstituted C6 to C30 aryl group, a substituted or unsubstituted C3 to C30 heteroaryl group, a halogen, a cyano group (—CN), a cyano-containing group, or a combination thereof or optionally, when a, b, c, d, and e are 2 or more, two adjacent to each other of a plurality of R$^{3a}$'s, two adjacent to each other of a plurality of R$^{3b}$'s, two adjacent to each other of a plurality of R$^{3c}$'s, two adjacent to each other of a plurality of R$^{3d}$'s, or two adjacent to each other of a plurality of R$^{3e}$'s may be linked to each other to provide a 5-membered aromatic ring or a 6-membered aromatic ring.

Chemical Formula 1C-2 may be represented by Chemical Formula 1C-2b:

[Chemical Formula 1C-2b]

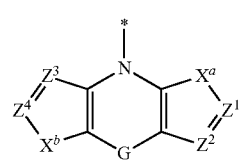

In Chemical Formula 1C-2b,

G may be a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ may each independently be present (e.g., may not be linked to each other to provide a ring) or R$^b$ and R$^c$, R$^d$ and R$^e$, R$^f$ and R$^g$, or R$^h$ and R$^i$ may be linked to each other to provide a ring, and n of —(CR$^f$R$^g$)$_n$— may be 1 or 2, X$^a$ and X$^b$ may each independently be —O—, —S—, —Se—, —Te—, —NR$^p$—, —SiR$^p$R$^r$—, or —GeR$^s$R$^t$—, wherein R$^p$, R$^q$, R$^r$, R$^s$, and R$^t$ may each independently be hydrogen, a halogen, a substituted or unsubstituted C1 to C10 alkyl group, or a substituted or unsubstituted C6 to C10 aryl group, Z$^1$ to Z$^4$ may each independently be N or CR$^x$, wherein R$^x$ may be hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when Z$^1$ to Z$^4$ are CR$^x$, R$^x$ of each of Z$^1$ to Z$^4$ may independently be present (e.g., Z$^1$ to Z$^4$ may not be linked to each other to form a ring) or at least an adjacent two Z$^1$ to Z$^4$ (e.g., some or all adjacent pairs of Z$^1$ to Z$^4$) may be linked to each other to form a 5-membered aromatic ring or a 6-membered aromatic ring.

In some example embodiments, in Chemical Formula 1C-2b, at least one of Z$^1$ and Z$^2$ and at least one of Z$^3$ and Z$^4$ may be CR$^x$, wherein R$^x$ may be a C1 to C10 haloalkyl group or a C1 to C10 alkoxy group.

In some example embodiments, in Chemical Formula 1C-2b, Z$^2$ and Z$^4$ may be CR$^x$ wherein R$^x$ may be a C1 to C10 haloalkyl group or a C1 to C10 alkoxy group.

According to some example embodiments, in Chemical Formula 1C-2b, at least one of Z$^1$ and Z$^2$ and/or at least one of Z$^3$ and Z$^4$ may be N. According to some example embodiments, in Chemical Formula 1C-2b, Z$^1$ and Z$^2$ and/or Z$^3$ and Z$^4$ may be N.

Chemical Formula 1C-2 may be represented by Chemical Formula 1C-2c:

[Chemical Formula 1C-2c]

In Chemical Formula 1C-2c,

G may be a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ may each independently be hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ may each independently be present or R$^b$ and R$^c$, R$^d$ and R$^e$, R$^f$ and R$^g$, or R$^h$ and R$^i$ may be linked to each other to provide a ring, and n of —(CR$^f$R$^g$)$_n$— may be 1 or 2, X$^a$ and X$^b$ may each independently be —O—, —S—, —Se—, —Te—, —NR$^p$—, —SiR$^p$R$^r$—, or —GeR$^s$R$^t$—, wherein R$^p$, R$^q$, R$^r$, R$^s$, and R$^t$ may each independently be hydrogen, a halogen, a substituted or unsubstituted C1 to C10 alkyl group, or a substituted or unsubstituted C6 to C10 aryl group, Z$^1$ to Z$^4$ may each independently be N or CR$^x$, wherein R$^x$ may be hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when $Z^1$ to $Z^4$ are $CR^x$, $R^x$ may each independently be present (e.g., may not be linked to each other to provide a ring) or at least an adjacent two $Z^1$ to $Z^4$ (e.g., some or all adjacent pairs of $Z^1$ to $Z^4$) may be linked to each other to form a 5-membered aromatic ring or a 6-membered aromatic ring.

In some example embodiments, in Chemical Formula 1C-2c, at least one of $Z^1$ and $Z^2$ and at least one of $Z^3$ and $Z^4$ may be $CR^x$ wherein $R^x$ may be a C1 to C10 haloalkyl group or a C1 to C10 alkoxy group.

In some example embodiments, in Chemical Formula 1C-2c, $Z^2$ and $Z^4$ may be $CR^x$, wherein $R^x$ may be a C1 to C10 haloalkyl group or a C1 to C10 alkoxy group.

According to some example embodiments, in Chemical Formula 1C-2c, at least one of $Z^1$ and $Z^2$ and/or at least one of $Z^3$ and $Z^4$ may be N. According to some example embodiments, in Chemical Formula 1C-2c, $Z^1$ and $Z^2$ and/or $Z^3$ and $Z^4$ may be N.

In Chemical Formula 1A, Ar may be an aromatic ring or heteroaromatic ring group represented by one of Chemical Formulas 1B-16 to 1B-25.

[Chemical Formulas 1B-16 to 1B-25]

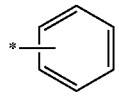

(1B-16)

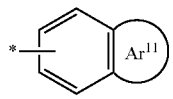

(1B-17)

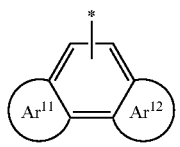

(1B-18)

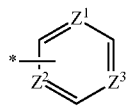

(1B-19)

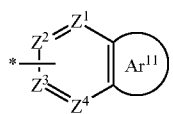

(1B-20)

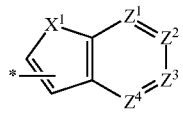

(1B-21)

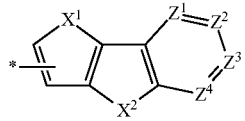

(1B-22)

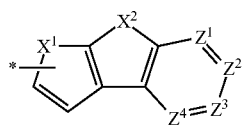

(1B-23)

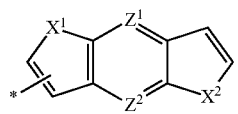

(1B-24)

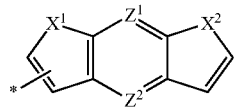

(1B-25)

In Chemical Formulas 1B-16 to 1B-25, $X^1$ and $X^2$ may each independently be O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ may each independently be hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, $Z^1$ to $Z^4$ may each independently be $CR^x$ or N, wherein $R^x$ may be hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, or a single bond, provided that (e.g., wherein) in Chemical Formula 1B-20, one of $Z^1$ to $Z^4$ may be $CR^x$ wherein $R^x$ may be a single bond, Ar$^{11}$ and Ar$^{12}$ may each independently be a substituted or unsubstituted C6 to C30 arene group or a substituted or unsubstituted C3 to C30 heteroarene group, and hydrogen of each aromatic ring and heteroaromatic ring may be replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group.

Chemical Formula 1B-17 may be represented by Chemical Formula 1B-17-1 or 1B-17-2.

[Chemical Formula 1B-17-1]

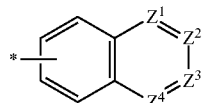

(1B-17-1)

[Chemical Formula 1B-17-2]

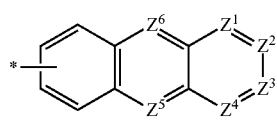

(1B-17-2)

In Chemical Formulas 1B-17-1 and 1B-17-2, $Z^1$ to $Z^6$ may each independently be N or $CR^x$, wherein $R^x$ may be hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when $Z^1$ to $Z^4$ are $CR^x$, $R^x$ may each independently be present (e.g., $R^x$ of each of $Z^1$ to $Z^4$ may be independently present) or at least an adjacent two $Z^1$ to $Z^4$ (e.g., some or all adjacent pairs of $Z^1$ to $Z^4$) may be linked to each other to form a 5-membered aromatic ring or a 6-membered aromatic ring.

Chemical Formula 1B-18 may be Chemical Formula 1B-18-1 or 1B-18-2.

[Chemical Formula 1B-18-1]

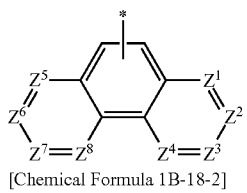

(1B-18-1)

[Chemical Formula 1B-18-2]

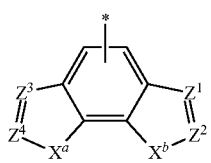

(1B-18-2)

In Chemical Formulas 1B-18-1 and 1B-18-2, $Z^1$ to $Z^8$ may each independently be N or $CR^x$, wherein $R^x$ may be hydrogen, deuterium, a C1 to C10 alkyl group, a C1 to C10 haloalkyl group, a C1 to C10 alkoxy group, a —$SiH_3$ group, a C1 to C10 alkylsilyl group, a —$NH_2$ group, a C1 to C10 alkylamine group, a C6 to C12 aryl group, a C3 to C12 heteroaryl group, a halogen, a cyano group, or a combination thereof, $X^a$ and $X^b$ may each independently be —O—, —S—, —Se—, —Te—, —$NR^p$—, —$SiR^pR^r$—, or —$GeR^sR^t$—, wherein $R^p$, $R^q$, $R^r$, $R^s$, and $R^t$ may each independently be hydrogen, a halogen, a substituted or unsubstituted C1 to C10 alkyl group, or a substituted or unsubstituted C6 to C10 aryl group, In Chemical Formula 1B-18-1, when $Z^1$ to $Z^8$ is $CR^x$, $R^x$ may each independently be present (e.g., $R^x$ of each of $Z^1$ to $Z^8$ may be independently present) or two adjacent ones of $Z^1$ to $Z^4$ (e.g., some or all adjacent pairs of $Z^1$ to $Z^4$) and/or at least two adjacent ones of $Z^5$ to $Z^8$ (e.g., some or all adjacent pairs of $Z^5$ to $Z^8$) may be linked to each other to form a 5-membered aromatic ring or a 6-membered aromatic ring, and in Chemical Formula 1B-18-2, when $Z^1$ and $Z^2$ and/or $Z^3$ and $Z^4$ may be $CR^x$, $R^x$ may each independently be present or $Z^1$ and $Z^2$ and/or $Z^3$ and $Z^4$ may be linked to each other to form a 5-membered aromatic ring or a 6-membered aromatic ring.

Chemical Formula 1B-20 may be Chemical Formula 1B-20-1 or 1B-20-2.

[Chemical Formula 1B-20-1]

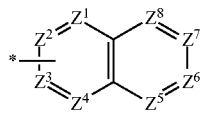

(1B-20-1)

-continued

[Chemical Formula 1B-20-2]

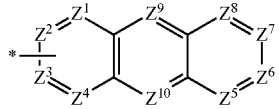

(1B-20-2)

In Chemical Formulas 1B-20-1 and 1B-20-2, $Z^1$ to $Z^{10}$ may each independently be N or $CR^x$, wherein $R^x$ may be hydrogen, deuterium, a C1 to C10 alkyl group, a C1 to C10 haloalkyl group, a C1 to C10 alkoxy group, a —$SiH_3$ group, a C1 to C10 alkylsilyl group, a —$NH_2$ group, a C1 to C10 alkylamine group, a C6 to C12 aryl group, a C3 to C12 heteroaryl group, a halogen, a cyano group, or a combination thereof, and when $Z^5$ to $Z^8$ are $CR^x$, $R^x$ may each independently be present (e.g., $R^x$ of each of $Z^5$ to $Z^8$ may be independently present) or at least adjacent two of $Z^5$ to $Z^8$ may be linked to each other to form a 5-membered aromatic ring or a 6-membered aromatic ring.

The aromatic ring or heteroaromatic ring group represented by one of Chemical Formulas 1B-16 to 1B-25 (e.g., Chemical Formula 1B-17-1, 1B-17-2, 1B-18-1, 1B-18-2, 1B-20-1, and 1B-20-2) may be substituted with an arylamine group, and the arylamine group may be represented by Chemical Formula 1C-1 described above. Chemical Formula 1C-1 may be represented by at least Chemical Formula 1C-1a or 1C-1b.

The aromatic ring or heteroaromatic ring group represented by one of Chemical Formulas 1B-16 to 1B-25 (e.g., Chemical Formula 1B-17-1, 1B-17-2, 1B-18-1, 11B-18-2, 11B-20-1, and 11B-20-2) may be substituted with an N-containing heterocyclic group, and the N-containing heterocyclic group may be represented by Chemical Formula 1C-2 described above. Chemical Formula 1C-2 may be represented by Chemical Formula 1C-2a, 1C-2b, or 1C-2c.

In Chemical Formula 1, by including the functional group represented by Chemical Formula 1A, charge transfer characteristics may be enhanced and bandgap energy may be reduced.

When two or more functional groups represented by Chemical Formula 1A are present, they may be linked at a symmetrical position or at an asymmetric position with respect to the core of the conjugated structure (squaraine (SQ) or croconaine (CR) in Chemical Formula 1).

In Chemical Formula 1, at least one of $R^{11a}$, $R^{11b}$, $R^{11c}$, $R^{12a}$, $R^{12b}$, or $R^{12c}$ may be a functional group represented by Chemical Formula 1A, and at least one of $R^{13a}$, $R^{13b}$, $R^{13c}$, $R^{14a}$, $R^{14b}$, or $R^{14c}$ may be the functional group represented by Chemical Formula 1A.

In some example embodiments, at least one of $R^{11a}$ to $R^{11c}$ (e.g., at least one of $R^{11a}$, $R^{11b}$, or $R^{11c}$) may be the functional group represented by Chemical Formula 1A, and at least one of $R^{13a}$ to $R^{13c}$ (e.g., at least one of $R^{13a}$, $R^{13b}$, or $R^{13c}$) may be the functional group represented by Chemical Formula 1A.

In some example embodiments, at least one of $R^{12a}$ to $R^{12c}$ (e.g., at least one of $R^{12a}$, $R^{12b}$, or $R^{12c}$) may be the functional group represented by Chemical Formula 1A, and at least one of $R^{14a}$ to $R^{14c}$ (e.g., at least one of $R^{14a}$, $R^{14b}$, or $R^{14}$) may be the functional group represented by Chemical Formula 1A.

In some example embodiments, $R^{11a}$ and $R^{13a}$ may be a functional group represented by Chemical Formula 1A.

In some example embodiments, $R^{12a}$ and $R^{14a}$ may be the functional group represented by Chemical Formula 1A.

In some example embodiments, $R^{11a}$ to $R^{14c}$ may be present independently of each other, or two adjacent functional groups may be linked to each other to form a fused ring with benzoindole.

In some example embodiments, two adjacent functional groups among $R^{11a}$, $R^{11b}$, $R^{11c}$, $R^{12a}$, $R^{12b}$, $R^{12c}$, $R^{13a}$, $R^{13b}$, $R^{13c}$, $R^{14a}$, $R^{14b}$, and $R^{14c}$ may be linked to each other to provide a C6 to C10 arene groups (e.g., benzene, naphthalene, etc.) or alternatively, a C3 to C10 heteroarene group (e.g., thiophene, pyrrole, pyridine, pyrimidine, etc.), and the arene or heteroarene groups may form a fused ring with benzoindole.

The compound may include a compound of Group 1.

[Group 1]

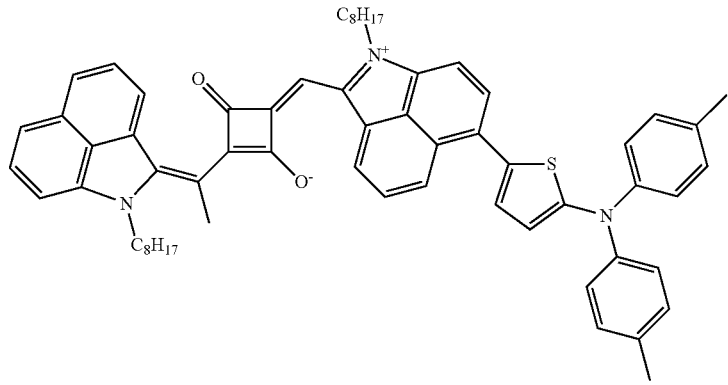

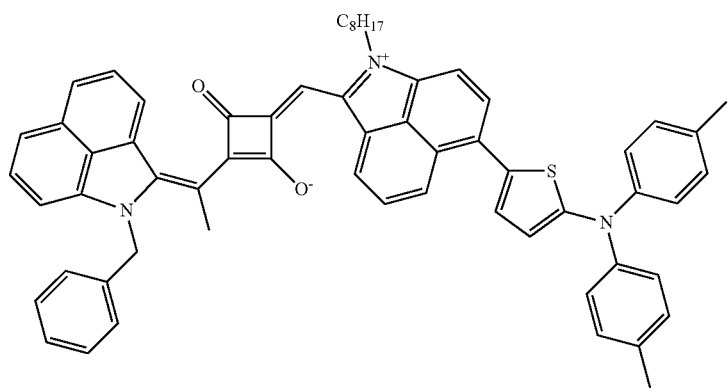

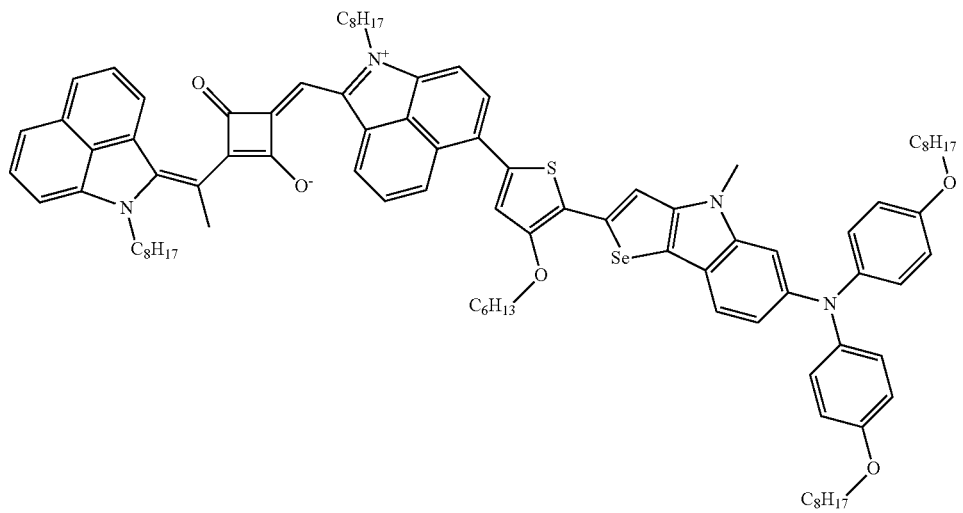

-continued
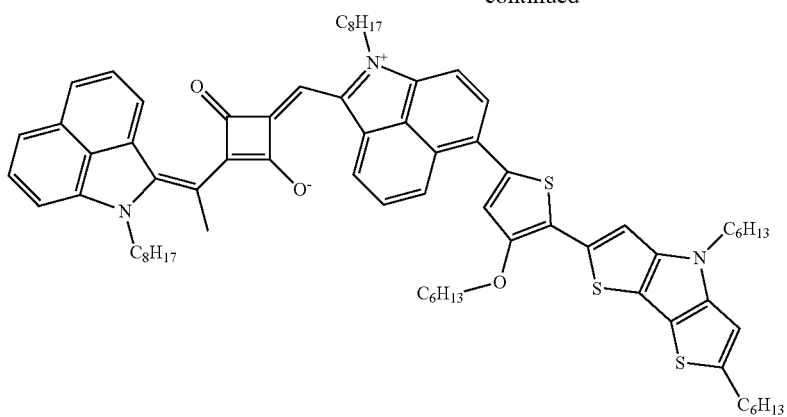
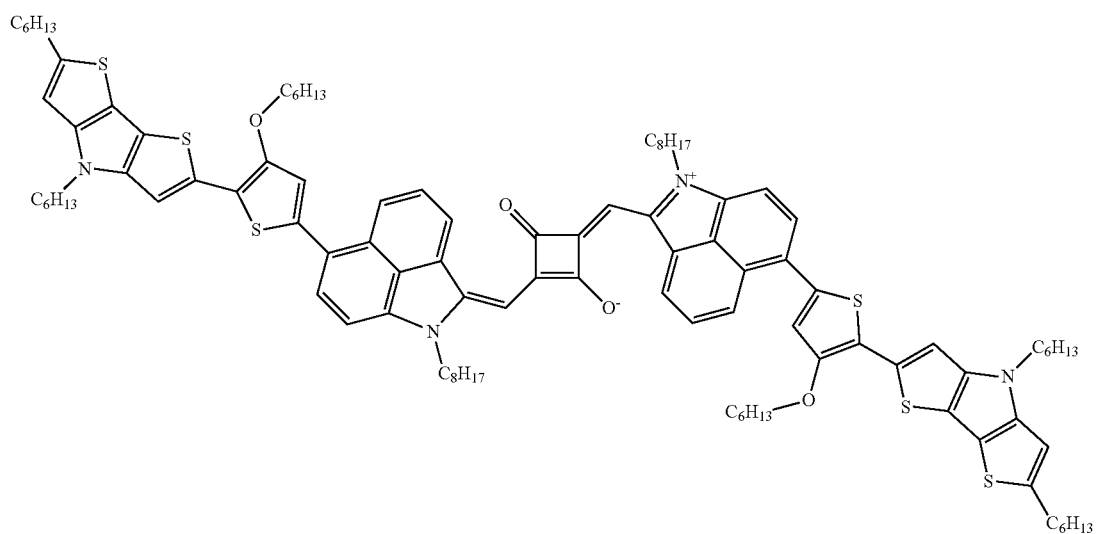
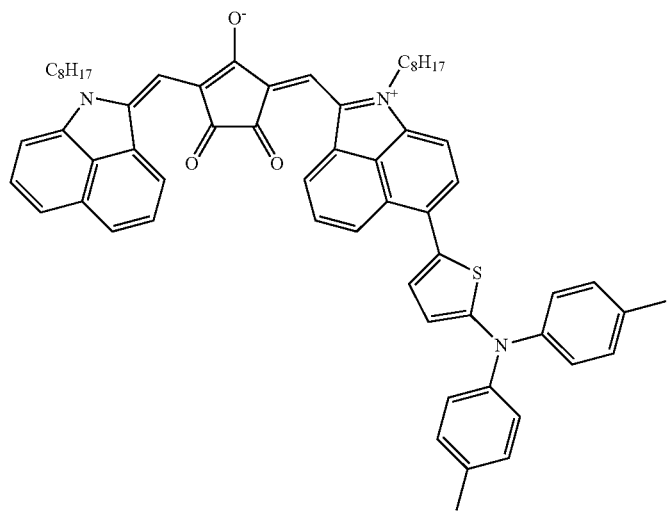

-continued

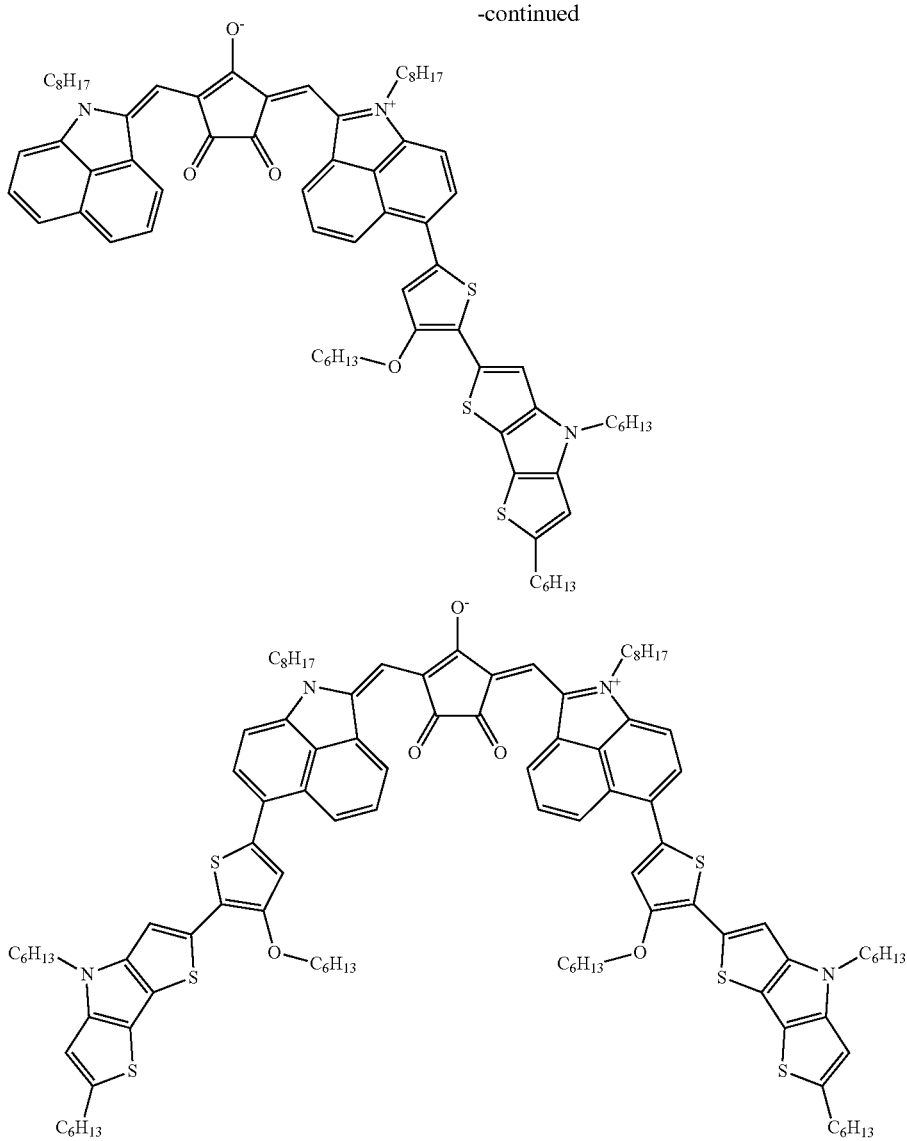

The compound may absorb light in an infrared wavelength region and the compound may have a peak absorption wavelength ($\lambda_{max}$) of, for example, greater than or equal to about 750 nm, for example greater than or equal to about 780 nm, greater than or equal to about 790 nm, greater than or equal to about 800 nm, greater than or equal to about 810 nm, greater than or equal to about 820 nm, or greater than or equal to about 830 nm. For example, the compound may have a peak absorption wavelength ($\lambda_{max}$) of, for example, about 750 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, or about 830 nm to about 2000 nm. In some example embodiments, the compound, or a layer, film or the like including the compound, may have a peak absorption wavelength ($\lambda_{max}$) of, for example, about 1000 nm to about 3000 nm. In some example embodiments, the compound, or a layer, film or the like including the compound, may have a peak absorption wavelength ($\lambda_{max}$) of, for example, about 1060 nm to about 1350 nm.

The compound may exhibit good charge transfer characteristics, and thus, it has good photoelectric conversion characteristics that absorb (e.g., selectively absorb) light and/or convert it (e.g., photoelectrically convert it) into an electrical signal, and thus may be effectively used as a photoelectric conversion material for photoelectric devices.

Some example embodiments provide an infrared absorber or an infrared absorbing/blocking film (absorbing and/or blocking film) including the compound. Restated, in some example embodiments, an infrared absorber (also referred to herein as an infrared absorber composition) may include the compound as described above, and in some example embodiments, an infrared absorbing/blocking film may include the compound as described above.

The compound, infrared absorber, and infrared absorbing/blocking film may be applied to various fields requiring light absorption characteristics in an infrared wavelength region.

The compound, composition, and/or infrared absorber has both light absorption characteristics and photoelectric characteristics in a near-infrared wavelength region/infrared wavelength region, and thus it may be effectively used as a photoelectric conversion material.

FIG. 1 is a cross-sectional view of a photoelectric device according to some example embodiments.

Referring to FIG. 1, a photoelectric device 100 according to some example embodiments includes a first electrode 10 and a second electrode 20 facing each other and a photoactive layer 30 between the first electrode 10 and the second electrode 20. In some example embodiments, the photoactive layer 30 may be an organic layer.

A substrate (not shown) may be disposed at the side of the first electrode 10 or the second electrode 20. The substrate may be for example made of (e.g., may at least partially comprise) an inorganic material such as glass; an organic material such as polycarbonate, polymethylmethacrylate, polyethyleneterephthalate, polyethylenenaphthalate, polyamide, polyethersulfone, or a combination thereof; or a silicon wafer. The substrate may be omitted.

One of the first electrode 10 or the second electrode 20 is an anode and the other is a cathode. For example, the first electrode 10 may be a cathode and the second electrode 20 may be an anode.

At least one of the first electrode 10 or the second electrode 20 may be a light-transmitting electrode and the light-transmitting electrode may be for example made of a conductive oxide such as an indium tin oxide (ITO), indium zinc oxide (IZO), zinc oxide (ZnO), tin oxide (SnO), aluminum tin oxide (AlTO), and/or fluorine doped tin oxide (FTO), or a metal thin layer of a single layer or a multilayer. When one of the first electrode 10 or the second electrode 20 is a non-light-transmitting electrode, it may be made of, for example, an opaque conductor such as aluminum (Al), silver (Ag), or gold (Au). For example, the first electrode 10 and the second electrode 20 may be all light-transmitting electrodes. For example, the second electrode 20 may be a light receiving electrode disposed at a light receiving side.

The photoactive layer 30 is a layer including a p-type semiconductor and an n-type semiconductor configured to provide a pn junction, which is a layer that may produce excitons by receiving light from outside (e.g., an exterior of the photoactive layer 30) and then separating holes and electrons from the produced excitons.

The p-type semiconductor and the n-type semiconductor may independently be a light absorbing material that is configured to absorb (e.g., selectively absorb) light in at least one portion of a wavelength region and the aforementioned infrared absorber may be a p-type semiconductor or an n-type semiconductor. For example, the aforementioned infrared absorber and/or compound represented by Chemical Formula 1 may be used for a p-type semiconductor and fullerene or a fullerene derivative may be included as an n-type semiconductor. Accordingly, it will be understood that the photoactive layer 30 may at least partially comprise the aforementioned compound, composition, and/or infrared absorber (e.g., may include the compound and either fullerene or a fullerene derivative). Additionally, it will be understood that the photoactive layer 30 may have a peak absorption wavelength ($\lambda_{max}$) of, for example, greater than or equal to about 750 nm, greater than or equal to about 770 nm, greater than or equal to about 780 nm, greater than or equal to about 790 nm, greater than or equal to about 800 nm, greater than or equal to about 810 nm, greater than or equal to about 820 nm, or greater than or equal to about 830 nm, and/or a peak absorption wavelength ($\lambda_{max}$) of about 750 nm to about 3000 nm, about 750 nm to about 2500 nm, about 780 nm to about 2200 nm, about 790 nm to about 2100 nm, about 800 nm to about 2000 nm, about 810 nm to about 2000 nm, about 820 nm to about 2000 nm, or about 830 nm to about 2000 nm. The photoactive layer 30, and thus the photoelectric device 100 may have improved infrared light absorption characteristics (e.g., may have improved sensitivity to light in an infrared wavelength region, improved absorbance of light in the infrared wavelength region, etc.) and thus improved photoelectric conversion performance and/or efficiency and/or improved thermal stability based on the photoactive layer including the aforementioned infrared absorber. In some example embodiments, the photoactive layer 30 may be an infrared absorbing/blocking film that includes the infrared absorber.

The photoactive layer 30 may include an intrinsic layer (I layer) in which the aforementioned infrared absorber (e.g., p-type semiconductor) and fullerene or a fullerene derivative (e.g., n-type semiconductor) may be co-deposited. Herein, the p-type semiconductor and the n-type semiconductor may be included in a volume ratio of about 1:9 to about 9:1, for example about 2:8 to about 8:2, about 3:7 to about 7:3, about 4:6 to about 6:4, or about 5:5.

The photoactive layer 30 may further include a p-type layer and/or an n-type layer in addition to the intrinsic layer. The p-type layer may include the aforementioned infrared absorber (e.g., p-type semiconductor) and the n-type layer may include the aforementioned n-type semiconductor. For example, they may be included in various combinations of p-type layer/I layer, I layer/n-type layer, p-type layer/I layer/n-type layer, and the like.

The photoelectric device 100 may further include an auxiliary layer between the first electrode 10 and the photoactive layer 30 and/or the second electrode 20 and the photoactive layer 30. The auxiliary layer may be a charge auxiliary layer or an optical auxiliary layer.

Figure 2:
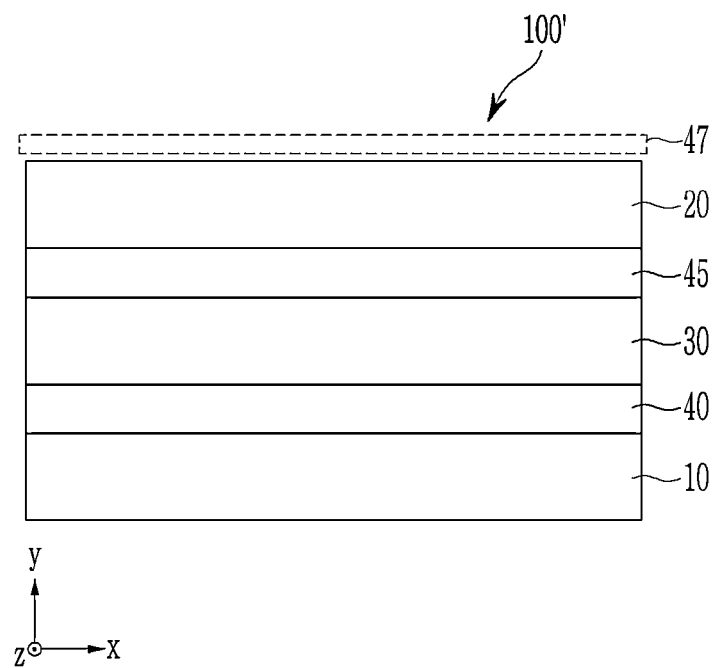
FIG. 2 is a cross-sectional view showing a photoelectric device according to some example embodiments.

This photoelectric device is shown in FIG. 2.

FIG. 2 is a cross-sectional view showing a photoelectric device according to some example embodiments.

Referring to FIG. 2, the photoelectric device 100' according to some example embodiments includes a first electrode 10 and a second electrode 20 facing each other, and a photoactive layer 30 between the first electrode 10 and the second electrode 20, like some example embodiments, including the example embodiments shown in FIG. 1.

In some example embodiments, including the example embodiments shown in FIG. 2, and unlike some example embodiments, including the example embodiments shown in FIG. 1, the photoelectric device 100' further includes charge auxiliary layers 40 and 45 between the first electrode 10 and the photoactive layer 30, and between the second electrode 20 and the photoactive layer 30, respectively. The charge auxiliary layers 40 and 45 (also referred to herein as first and second charge auxiliary layers, respectively) facilitate the movement of holes and electrons separated from the photoactive layer 30 to increase efficiency of the photoelectric device 100'. In some example embodiments, only one of the first charge auxiliary layer 40 or the second charge auxiliary layer 45 is included in the photoelectric device 100'.

The charge auxiliary layers 40 and 45 may include at least one selected from a hole injection layer (HIL) for facilitating hole injection, a hole transport layer (HTL) for facilitating hole transport, an electron blocking layer (EBL) for preventing electron transport, an electron injection layer (EIL) for facilitating electron injection, an electron transport layer (ETL) for facilitating electron transport, and a hole blocking layer (HBL) for preventing hole transport.

The charge auxiliary layers 40 and/or 45 may include for example an organic material, an inorganic material, or an organic-inorganic material. The organic material may be an organic material having hole or electron characteristics and the inorganic material may be for example a metal oxide such as a molybdenum oxide, a tungsten oxide, or a nickel oxide.

The charge auxiliary layers 40 and 45 may include for example the aforementioned compound represented by Chemical Formula 1 and/or the aforementioned infrared absorber.

In some example embodiments, where the photoelectric device 100' includes at least one charge auxiliary layer (which may include one or both of the first charge auxiliary layer 40 or the second charge auxiliary layer 45), at least one of the first electrode 10, the second electrode 20, the photoactive layer 30, or the charge auxiliary layer may include the aforementioned compound represented by Chemical Formula 1.

In some example embodiments, the charge auxiliary layer (which may include one or both of the first charge auxiliary layer 40 or the second charge auxiliary layer 45) may include the compound and the photoactive layer 30, the first electrode 10, and the second electrode 20 may not include the aforementioned compound represented by Chemical Formula 1.

In some example embodiments, the photoactive layer 30 may include the compound and the charge auxiliary layer (which may include one or both of the first charge auxiliary layer 40 or the second charge auxiliary layer 45), the first electrode 10, and the second electrode 20 may not include the aforementioned compound represented by Chemical Formula 1.

In some example embodiments, the photoelectric device 100' may include both of the first and second charge auxiliary layers 40 and 45, and at least one of the first electrode 10, the second electrode 20, the photoactive layer 30, the first charge auxiliary layer 40, or the second charge auxiliary layer 45 may include the aforementioned compound represented by Chemical Formula 1.

The charge auxiliary layers 40 and/or 45, and thus the photoelectric device 100', may have improved infrared light absorption characteristics (e.g., may have improved sensitivity to light in an infrared wavelength region, improved absorbance of light in the infrared wavelength region, etc.) and thus improved photoelectric conversion performance and/or efficiency, based on at least one of the photoactive layer 30 or one or more of the charge auxiliary layers 40 and/or 45 including the aforementioned compound, composition, and/or infrared absorber.

The optical auxiliary layer may be disposed in the light incident direction of the photoelectric device. For example, when the second electrode 20 is a light receiving electrode (e.g., the electrode proximate to a surrounding environment from which light is received at the photoelectric device 100'), the optical auxiliary layer may be disposed on the photoactive layer 30. For example, the optical auxiliary layer may be disposed between the second electrode 20 and the photoactive layer 30.

The photoelectric devices 100 and 100' may further include an anti-reflection layer 47 on one surface of the first electrode 10 or the second electrode 20. The anti-reflection layer 47 is disposed at a light incidence side and lowers reflectance of light of incident light and thereby light absorbance is further improved. For example, when light enters from the first electrode 10, the anti-reflection layer 47 may be disposed on the first electrode 10 while when light enters from the second electrode 20, the anti-reflection layer 47 may be disposed under the second electrode 20.

The anti-reflection layer 47 may include, for example a material having a refractive index of about 1.6 to about 2.5 and may include for example at least one of a metal oxide, a semi-metal oxide, a metal sulfide, or an organic material having a refractive index within the ranges. The anti-reflection layer may include, for example a metal oxide, chalcogen oxide, or a semi-metal oxide such as an aluminum-containing oxide, a molybdenum-containing oxide, a tungsten-containing oxide, a vanadium-containing oxide, a rhenium-containing oxide, a niobium-containing oxide, a tantalum-containing oxide, a titanium-containing oxide, a nickel-containing oxide, a copper-containing oxide, a cobalt-containing oxide, a manganese-containing oxide, a chromium-containing oxide, a tellurium-containing oxide, or a combination thereof; a metal sulfide such as a zinc sulfide; or an organic material such as an amine derivative, but is not limited thereto.

In the photoelectric devices 100 and 100', when light enters said photoelectric device 100 and/or 100' and thus enters the photoactive layer 30 thereof from (e.g., via) the first electrode 10 or the second electrode 20 and the photoactive layer 30 thus absorbs the light in a particular (or, alternatively, predetermined) wavelength region, excitons may be generated thereinside. The excitons are separated into holes and electrons in the photoactive layer 30, and the separated holes are transported to an anode that is one of the first electrode 10 or the second electrode 20 and the separated electrons are transported to the cathode that is the other of the first electrode 10 and the second electrode 20 so as to flow (e.g., induce, generate, etc.) a current.

The photoelectric devices 100 and 100' may be applied to (e.g., included in) a sensor such as an image sensor (e.g., CMOS image sensor), a photodetector, an optical sensor (infrared light sensor), a solar cell, etc., but example embodiments are not limited thereto.

The photoelectric devices 100 and 100' may be applied to (e.g., included in) a sensor, which may be an organic sensor. The sensor, which may be an organic sensor, may be an organic CMOS sensor, for example, an organic CMOS infrared sensor or an organic CMOS image sensor.

In some example embodiments, the photoelectric device 100 may include the compound, composition, and/or infrared absorber in any of the elements thereof, including, in addition to or alternative to the photoactive layer 30, one or more of the first electrode 10 or the second electrode 20. In some example embodiments, the photoelectric device 100' may include the compound, composition, and/or infrared absorber in any of the elements thereof, including, in addition to or alternative to the photoactive layer 30 and/or one or more of the charge auxiliary layers 40/45, one or more of the first electrode 10 or the second electrode 20.

Hereinafter, an image sensor including the photoelectric device will be described with reference to the drawings.

Figure 3:
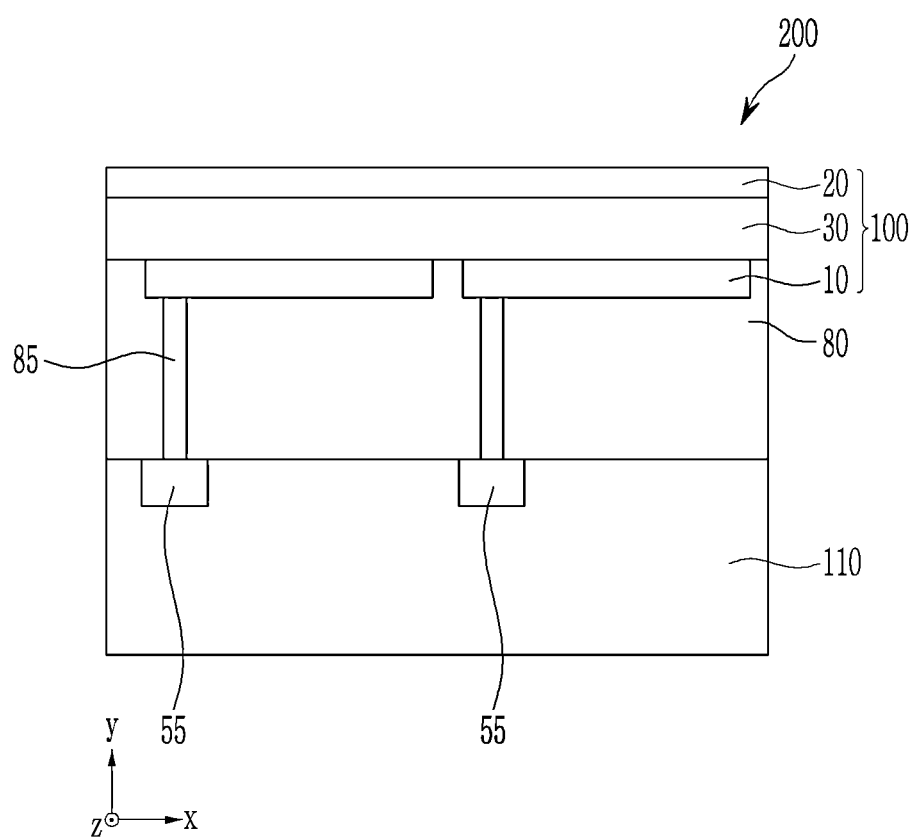
FIG. 3 is a cross-sectional view showing an image sensor according to some example embodiments.

FIG. 3 is a cross-sectional view showing an image sensor according to some example embodiments.

Referring to FIG. 3, the image sensor 200 according to some example embodiments includes a semiconductor substrate 110, an insulation layer 80, and a photoelectric device 100. FIG. 3 illustrates an image sensor 200 including the photoelectric device 100 of FIG. 1, but the image sensor 200 may also include the photoelectric device 100' of FIG. 2.

The semiconductor substrate 110 may be a silicon substrate and is integrated with a transmission transistor (not shown) and a charge storage 55. The charge storage 55 may be integrated in each pixel. The charge storage 55 is electrically connected to the photoelectric device 100 and information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the semiconductor substrate 110.

The insulation layer 80 is formed on the metal wire and pad. The insulation layer 80 may be made of an inorganic insulating material such as a silicon oxide and/or a silicon nitride, or a low dielectric constant (low K) material such as SiC, SiCOH, SiCO, and/or SiOF. The insulation layer 80 has a trench 85 exposing the charge storage 55. The trench 85 may be filled with fillers.

The aforementioned photoelectric device 100 is formed on the insulation layer 80. As described above, the photoelectric device 100 includes a first electrode 10, a photoactive layer 30, and a second electrode 20. Even though a structure in which the first electrode 10, the photoactive layer 30, and the second electrode 20 are sequentially stacked is shown as an example in the drawing, the present disclosure is not limited to this structure, and the second electrode 20, the photoactive layer 30, and the first electrode 10 may be arranged in this order.

The first electrode 10 and the second electrode 20 may both be transparent electrodes, and the photoactive layer 30 may be the same as described above with reference to FIGS. 1 and 2. The photoactive layer 30 may selectively absorb light in an infrared wavelength region. Incident light from the side of the second electrode 20 may be photoelectrically converted by mainly absorbing light in an infrared wavelength region in the photoactive layer 30. As noted above with reference to FIG. 1, the photoactive layer 30 may include the aforementioned compound, composition, and/or infrared absorber and thus may have improved sensitivity to infrared light, such that the operational performance and/or efficiency of the image sensor 200 in absorbing and/or converting incident infrared light into electrical signals (e.g., photoelectric conversion performance and/or efficiency) may be improved.

Focusing lens (not shown) may be further formed on the photoelectric device 100. The focusing lens may control a direction of incident light and gather the light in one region. The focusing lens may have a shape of, for example, a cylinder or a hemisphere, but is not limited thereto.

Figure 4:
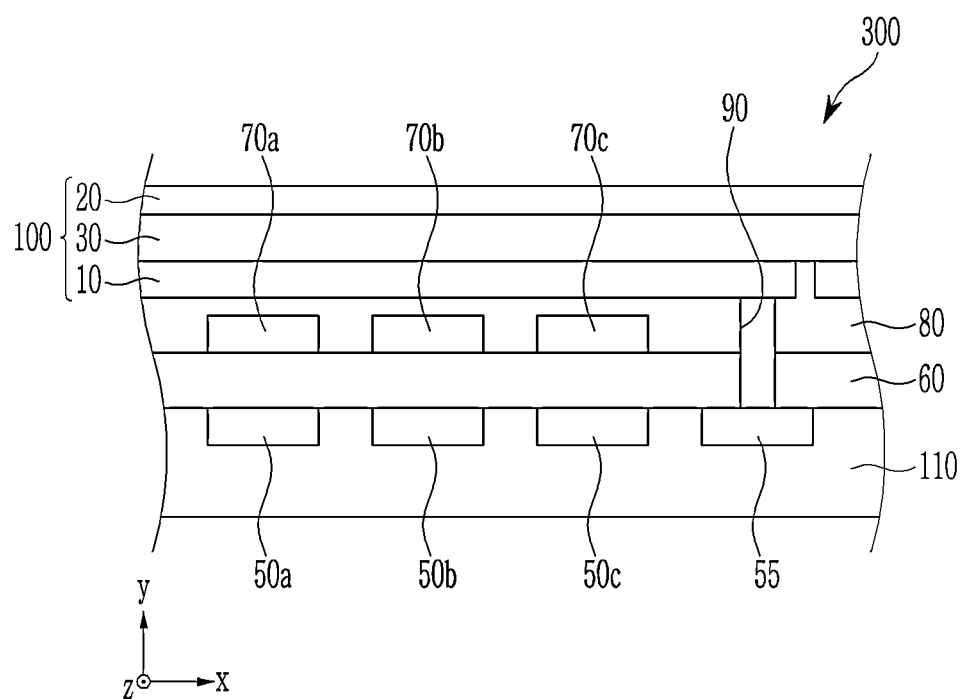
FIG. 4 is a cross-sectional view showing an image sensor according to some example embodiments.

FIG. 4 is a cross-sectional view showing an image sensor according to some example embodiments.

Referring to FIG. 4, an image sensor 300 according to some example embodiments includes a semiconductor substrate 110 integrated with photo-sensing devices (e.g., photodiodes, including silicon-based photodiodes) 50a, 50b, and 50c, a transmission transistor (not shown), and a charge storage 55, a lower insulation layer 60, color filters 70a, 70b, and 70c, an upper insulation layer 80, and a photoelectric device 100.

The semiconductor substrate 110 may be integrated with photo-sensing devices 50a, 50b, and 50c, a transmission transistor (not shown), and a charge storage 55. The photo-sensing devices 50a, 50b, and 50c may be photodiodes.

The photo-sensing devices 50a, 50b, and 50c, the transmission transistor, and/or the charge storage 55 may be integrated in each pixel. For example, the photo-sensing device 50a may be included in a red pixel, the photo-sensing device 50b may be included in a green pixel, and the photo-sensing device 50c may be included in a blue pixel.

The photo-sensing devices 50a, 50b, and 50c may sense (e.g., selectively absorb and/or convert (into electrical signals, e.g., photoelectrically convert)) incident light, the information sensed by the photo-sensing devices may be transferred by the transmission transistor, the charge storage 55 is electrically connected to the photoelectric device 100, and the information of the charge storage 55 may be transferred by the transmission transistor.

A metal wire (not shown) and a pad (not shown) are formed on the semiconductor substrate 110. In order to decrease signal delay, the metal wire and pad may be made of a metal having low resistivity, for example, aluminum (Al), copper (Cu), silver (Ag), and alloys thereof, but are not limited thereto. Further, it is not limited to the structure, and the metal wire and pad may be disposed under the photo-sensing devices 50a and 50b.

The lower insulation layer 60 is formed on the metal wire and the pad. The lower insulation layer 60 may include a same or different material composition as the insulation layer 80.

Color filters 70a, 70b, and 70c are formed on the lower insulation layer 60. The color filters 70a, 70b, and 70c includes a red filter 70a formed in a red pixel, a green filter 70b formed in a green pixel, and a blue filter 70c formed in a blue pixel.

The upper insulation layer 80 is formed on the color filters 70a, 70b, and 70c. The upper insulation layer 80 eliminates steps caused by the color filters 70a, 70b, and 70c and planarizes the surface.

The aforementioned photoelectric device 100 is formed on the upper insulation layer 80. As described above, the photoelectric device 100 includes a first electrode 10, a photoactive layer 30, and a second electrode 20. Even though a structure in which the first electrode 10, the photoactive layer 30, and the second electrode 20 are sequentially stacked is shown as an example in the drawing, the present disclosure is not limited to this structure, and the second electrode 20, the photoactive layer 30, and the first electrode 10 may be arranged in this order.

The first electrode 10 and the second electrode 20 may both be transparent electrodes, and the photoactive layer 30 is the same as described above. The photoactive layer 30 may selectively absorb light in a near-infrared/infrared wavelength region. As noted above with regard to photoelectric devices 100 and 100', any portion of the photoelectric device 100 (e.g., first electrode 10, second electrode 20, and/or photoactive layer 30) may include the aforementioned compound, composition, and/or infrared absorber.

Incident light from the side of the second electrode 20 may be photoelectrically converted by mainly absorbing light in a near-infrared wavelength region in the photoactive layer 30. Light in the remaining wavelength region may pass through the first electrode 10 and the color filters 70a, 70b, and 70c, the light in a red wavelength region passing through the color filter 70a may be sensed by the photo-sensing device 50a, the light in a green wavelength region passing through the color filter 70b may be sensed by the photo-sensing device 50b, and the light in a blue wavelength region passing through the color filter 70c may be sensed by the photo-sensing device 50c.

As noted above with reference to FIG. 1, the photoactive layer 30 may include the aforementioned compound, composition, and/or infrared absorber and thus may have improved sensitivity to near-infrared light, such that the operational performance and/or efficiency of the image sensor 300 in absorbing and/or converting incident infrared light into electrical signals (e.g., photoelectric conversion performance and/or efficiency) may be improved.

Accordingly, where an image sensor 300 includes a photoelectric device 100 that includes the compound, composition, and/or infrared absorber and is configured to selectively absorb and/or convert (into electrical signals, e.g., photoelectrically convert) light in a first infrared wavelength region, the image sensor may include an additional sensor that includes a plurality of photodiodes (e.g., photo-sensing devices 50a, 50b, 50c) at least partially embedded within the semiconductor substrate and configured to selectively absorb and/or convert (into electrical signals, e.g., photoelectrically convert) light in separate visible wavelength regions (e.g., red, green, and/or blue light).

Figure 5:
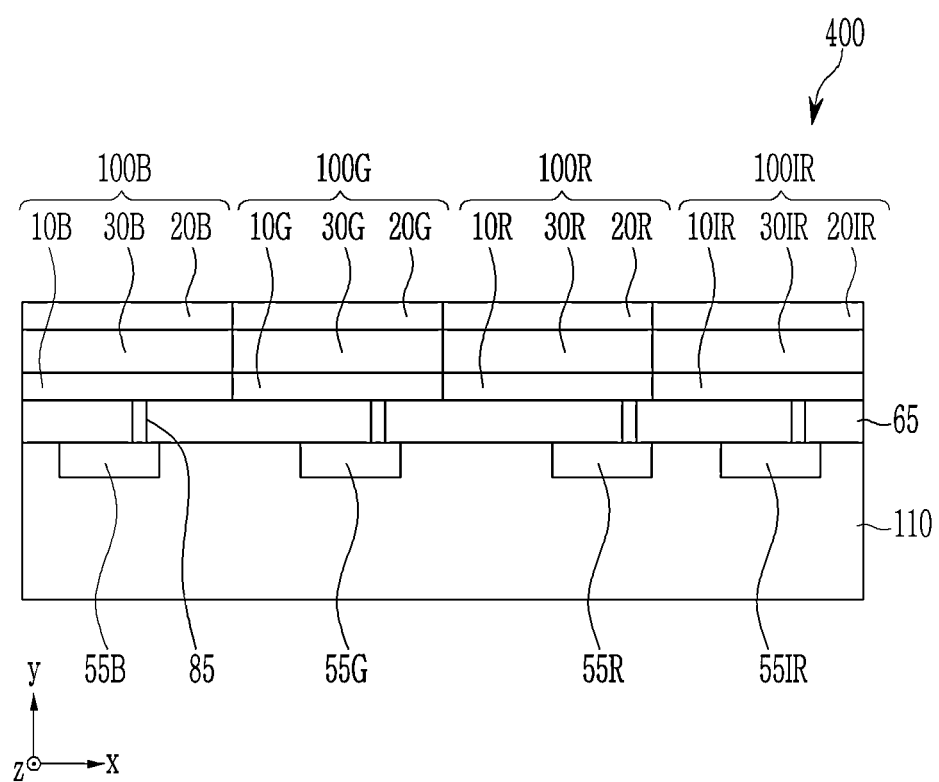
FIG. 5 is a cross-sectional view showing an image sensor according to some example embodiments.

FIG. 5 is a cross-sectional view showing an image sensor according to some example embodiments.

Referring to FIG. 5, an image sensor 400 according to some example embodiments includes a semiconductor substrate 110 integrated with an infrared light charge storage 55IR, a blue light charge storage 55B, a green light charge storage 55G, a red light charge storage 55R, and a transmission transistor (not shown), a lower insulation layer 65, a blue photo-sensing device 100B, a green photo-sensing device 100G, a red photo-sensing device 100R, and an infrared photo-sensing device 100IR.

The semiconductor substrate 110 may be a silicon substrate, and the infrared light charge storage 55IR, blue light charge storage 55B, the green light charge storage 55G, the red light charge storage 55R, and the transfer transistor (not shown) are integrated therein. The blue light charge storage 55B, the green light charge storage 55G, and the red light charge storage 55R may be integrated for each blue pixel, green pixel, and red pixel.

Charges generated in the infrared photo-sensing device 100IR, the blue photo-sensing device 100B, the green photo-sensing device 100G, and the red photo-sensing device 100R are collected in the infrared light charge storage 55IR, the blue light charge storage 55B, the green light charge storage 55G, and the red light charge storage 55R, which are electrically connected to each of the infrared photo-sensing device 100IR, the blue photo-sensing device 100B, the green photo-sensing device 100G, and the red photo-sensing device 100R.

A metal wire (not shown) and a pad (not shown) are formed on the semiconductor substrate 110. In order to decrease signal delay, the metal wires and pads may be made of a metal having low resistivity, for example, aluminum (Al), copper (Cu), silver (Ag), and alloys thereof, but are not limited thereto.

The lower insulation layer 65 may be formed on the metal wires and pads. The lower insulation layer 65 may be made of an inorganic insulation material such as a silicon oxide and/or a silicon nitride, or a low dielectric constant (low K) material such as SiC, SiCOH, SiCO, and SiOF.

The blue photo-sensing device 100B, the green photo-sensing device 100G, the red photo-sensing device 100R, and the infrared photo-sensing device 100IR are formed on the lower insulation layer 65. The blue photo-sensing device 100B may include a first electrode 10B, a second electrode 20B, and a photoactive layer 30B configured to selectively absorb light in a blue wavelength region, the green photo-sensing device 100G may include a first electrode 10G, a second electrode 20G, and a photoactive layer 30G configured to selectively absorb light in a green wavelength region, the red photo-sensing device 100R may include a first electrode 10R, a second electrode 20R, and a photoactive layer 30R configured to selectively absorb light in a red wavelength region, and the infrared photo-sensing device 100IR may include a first electrode 10IR, a second electrode 20IR, and a photoactive layer 30IR configured to selectively absorb light in an infrared light wavelength region.

The first electrodes 10B, 10G, 10R, and 10IR and the second electrodes 20B, 20G, 20R, and 20IR may be light-transmitting electrodes and may be made of, for example, a transparent conductor such as indium tin oxide (ITO), indium zinc oxide (IZO), zinc oxide (ZnO), tin oxide ($SnO_2$), aluminum tin oxide (AlTO), and fluorine-doped tin oxide (FTO), or may be a metal thin film having a thin thickness of several nanometers to several tens of nanometers or a metal thin film having a thin thickness of several nanometers to several tens of nanometers doped with a metal oxide.

The photoactive layers 30B, 30G, 30R, and 30IR may include a p-type semiconductor material and an n-type semiconductor material. The photoactive layer 30B of the blue photo-sensing device 100B may include a p-type semiconductor material configured to selectively absorb light in a blue wavelength region and an n-type semiconductor material configured to selectively absorb light in a blue wavelength region, the photoactive layer 30G of the green photo-sensing device 100G may include a p-type semiconductor material configured to selectively absorb light in a green wavelength region and an n-type semiconductor material configured to selectively absorb light in a green wavelength region, the photoactive layer 30R of the red photo-sensing device 100R may include a p-type semiconductor material configured to selectively absorb light in a red wavelength region and an n-type semiconductor material configured to selectively absorb light in a red wavelength region, and the photoactive layer 30IR of the infrared photo-sensing device 100IR may include a p-type semiconductor material (e.g., the aforementioned compound, composition, and/or infrared absorber) configured to selectively absorb light in an infrared region and an n-type semiconductor material configured to selectively absorb light in an infrared region. The infrared photo-sensing device 100IR may selectively absorb light in an infrared region of greater than or equal to about 750 nm and less than or equal to about 3000 nm without absorption of the visible light region.

Figure 6:
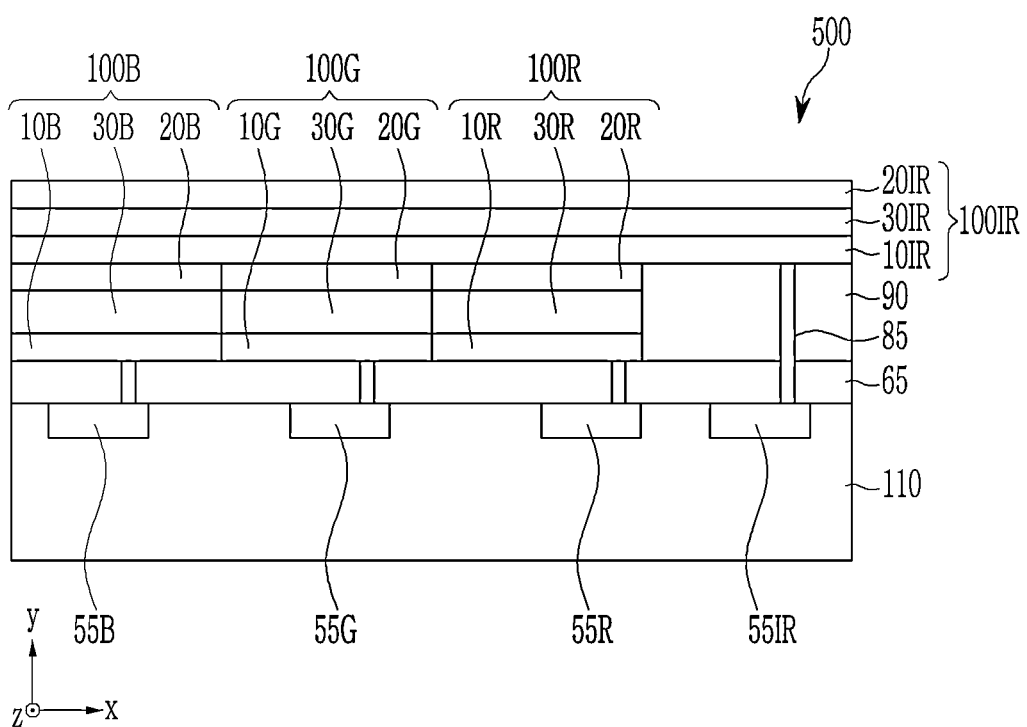
FIG. 6 is a cross-sectional view showing an image sensor according to some example embodiments.
Figure 7:
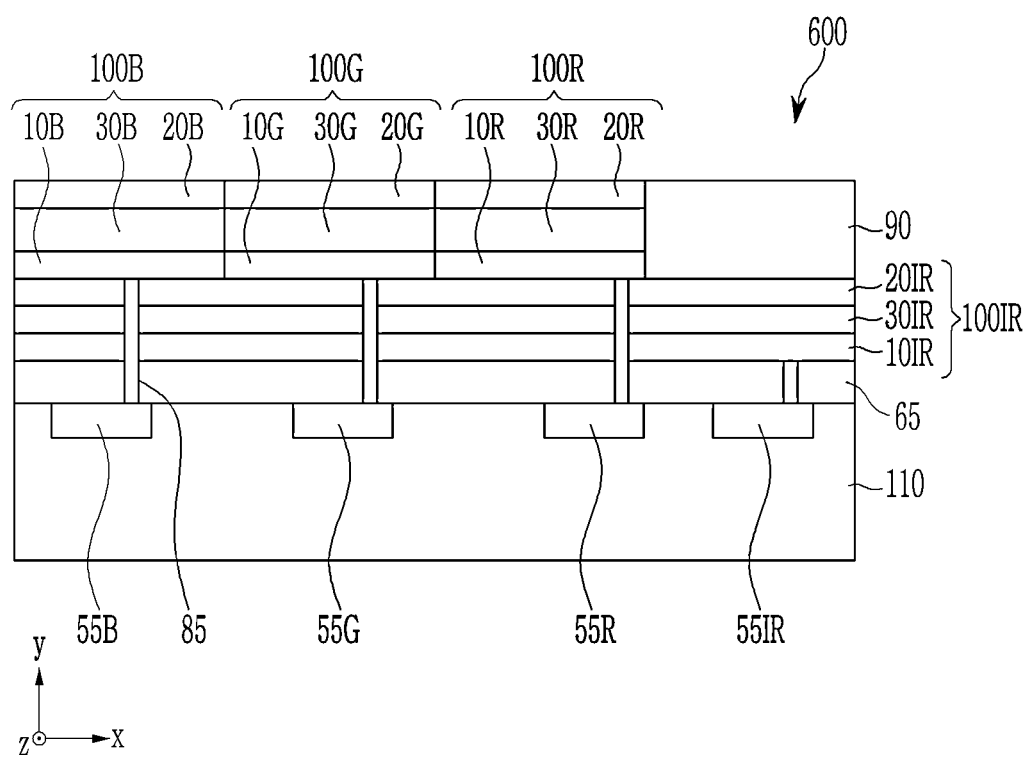
FIG. 7 is a cross-sectional view showing an image sensor according to some example embodiments.

FIG. 6 is a cross-sectional view showing an image sensor according to some example embodiments. FIG. 7 is a cross-sectional view showing an image sensor according to some example embodiments.

Referring to FIG. 6, an image sensor 500 may include an semiconductor substrate 110 integrated with an infrared light charge storage 55IR, a blue light charge storage 55B, a green light charge storage 55G, a red light charge storage 55R, and a transmission transistor (not shown), a lower insulation layer 65, an upper insulation layer 90, a blue photo-sensing device 100B, a green photo-sensing device 100G, a red photo-sensing device 100R, and an infrared photo-sensing device 100IR. The infrared photo-sensing device 100IR is formed on is formed on the whole front surface of the blue photo-sensing device 100B, the green photo-sensing device 100G, and the red photo-sensing device 100R. The rest of the configuration is the same as that of the image sensor shown in FIG. 5.

In the configuration of FIG. 6, the infrared photo-sensing device 100IR may be present on the lower insulation layer 65, the blue photo-sensing device 100B, the green photo-sensing device 100G, and the red photo-sensing device 100R may be disposed thereon. An image sensor 600 having such a configuration is shown in FIG. 7.

The infrared photo-sensing device 100IR may be configured to selectively absorb light in an infrared region of greater than or equal to about 750 nm and less than or equal to about 3000 nm, and have a large absorption area to improve efficiency.

The sensor according to some example embodiments may include a plurality of sensors having different functions. For example, at least one sensor of the plurality of sensors having different functions may be a biometric sensor, and the biometric sensor may be for example an iris sensor, a depth sensor, a fingerprint sensor, a blood vessel distribution sensor, and the like, but is not limited thereto.

For example, one sensor of the plurality of sensors having different functions may be an iris sensor and the other may be a depth sensor. The iris sensor identifies a person by using unique iris characteristics of every person and specifically, taking an image of an eye of a user within an appropriate distance, processing the image, and comparing it with his/her stored image. The depth sensor identifies a shape and a location of an object from its three-dimensional information by taking an image of the object within an appropriate distance with a user and processing the image. This depth sensor may be for example used as a face recognition sensor.

In some example embodiments, a plurality of sensors may include, for example a first infrared light sensor configured to sense light in an infrared region having a first wavelength ($\lambda_1$) in an infrared wavelength region and a second infrared light sensor configured to sense light in an infrared region having a second wavelength ($\lambda_2$) in an infrared wavelength region.

The first wavelength ($\lambda_1$) and the second wavelength ($\lambda_2$) may be for example different in a wavelength region of about 750 nm to about 3000 nm, and for example a difference between the first wavelength ($\lambda_1$) and the second wavelength ($\lambda_2$) may be greater than or equal to about 30 nm, greater than or equal to about 50 nm, greater than or equal to about 70 nm, greater than or equal to about 80 nm, or greater than or equal to about 90 nm.

For example, one of the first wavelength ($\lambda_1$) or the second wavelength ($\lambda_2$) may belong to a wavelength region of about 780 nm to about 900 nm and the other of the first wavelength ($\lambda_1$) and the second wavelength ($\lambda_2$) may belong to a wavelength region of greater than about 900 nm and less than or equal to about 1000 nm.

For example, one of the first wavelength ($\lambda_1$) or the second wavelength ($\lambda_2$) may belong to a wavelength region of about 780 nm to about 840 nm and the other of the first wavelength ($\lambda_1$) and the second wavelength ($\lambda_2$) may belong to a wavelength region of about 910 nm to about 970 nm.

For example, one of the first wavelength ($\lambda_1$) or the second wavelength ($\lambda_2$) may belong to a wavelength region of about 800 nm to about 830 nm and the other of the first wavelength ($\lambda_1$) and the second wavelength ($\lambda_2$) may belong to a wavelength region of about 930 nm to about 950 nm.

For example, one of the first wavelength ($\lambda_1$) or the second wavelength ($\lambda_2$) may belong to a wavelength region of about 805 nm to about 815 nm and the other of the first wavelength ($\lambda_1$) and the second wavelength ($\lambda_2$) may belong to a wavelength region of about 935 nm to about 945 nm.

For example, one of the first wavelength ($\lambda_1$) or the second wavelength ($\lambda_2$) may about 810 nm and the other of the first wavelength ($\lambda_1$) and the second wavelength ($\lambda_2$) may be about 940 nm.

Figure 8:
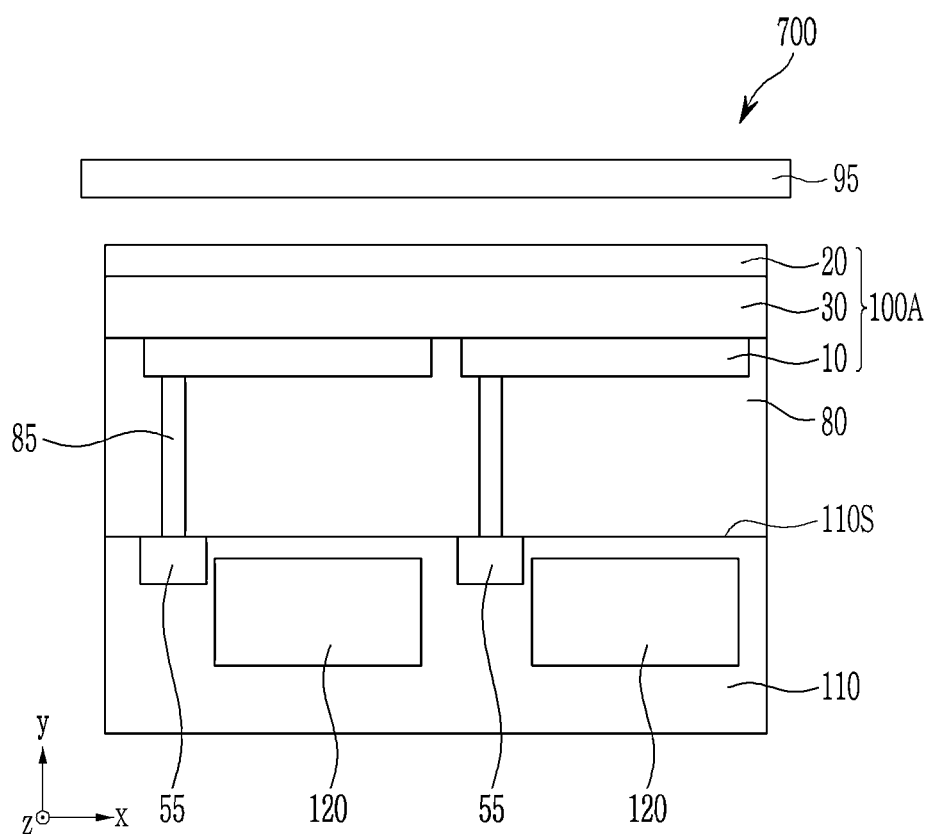
FIG. 8 is a cross-sectional view showing an image sensor according to some example embodiments.

FIG. 8 is a cross-sectional view illustrating an image sensor including a plurality of sensors according to some example embodiments.

The image sensor 700 according to some example embodiments includes a dual bandpass filter 95, a first infrared light sensor 100A, an insulation layer 80 (also referred to herein as an upper insulation layer), and a semiconductor substrate 110 integrated with a second infrared light sensor 120, such that the second infrared light sensor 120 is at least partially embedded within the semiconductor substrate 110.

The first infrared light sensor 100A and the second infrared light sensor 120 are stacked, e.g., may overlap in a vertical direction that is perpendicular to the upper surface 110S of the semiconductor substrate 110.

The dual bandpass filter 95 may be disposed on a front side of the first infrared light sensor 100A and may selectively transmit infrared light including the first wavelength ($\lambda_1$) and infrared light including the second wavelength ($\lambda_2$) and may block and/or absorb other light. Herein, other light may include light in an ultraviolet (UV) and visible region.

The first infrared light sensor 100A includes a first electrode 10, a photoactive layer 30, and a second electrode 20. The first infrared light sensor 100A may be the same as the photoelectric device 100 according to some example embodiments, including the example embodiments described with reference to FIG. 1, but it will be understood that, in some example embodiments, the first infrared light sensor 100A may be the same as the photoelectric device 100' according to some example embodiments, including the example embodiments described with reference to FIG. 2.

The second infrared light sensor 120 may be integrated in the semiconductor substrate 110 (e.g., encompassed within a volume space defined by outer surfaces of the semiconductor substrate 110) and may be a photo-sensing device. The semiconductor substrate 110 may be for example a silicon substrate and may be integrated with the second infrared light sensor 120, the charge storage 55, and a transmission transistor (not shown).

The second infrared light sensor 120 may be a photodiode and may sense entered light, and sensed information is transferred by the transmission transistor. Herein, the light entered into the second infrared light sensor 120 is light that passes the dual bandpass filter 95 and the first infrared light sensor 100A and may be infrared light in a particular (or, alternatively, predetermined) region including the second wavelength ($\lambda_2$). All infrared light in a particular (or, alternatively, predetermined) region including the first wavelength ($\lambda_1$) may be absorbed by the photoactive layer 30 and may not reach the second infrared light sensor 120. In this case, a separate filter for wavelength selectivity with respect to the light entered into the second infrared light sensor 120 is not separately needed. However, for the time when all infrared light in a particular (or, alternatively, predetermined) region including the first wavelength ($\lambda_1$) is not absorbed by the photoactive layer 30, a filter between the first infrared light sensor 100A and the second infrared light sensor 120 may be further disposed.

Accordingly, in the image sensor 700, the first infrared light sensor 100A may be understood to include a photoelectric device (e.g., photoelectric device 100 and/or 100') configured to sense (e.g., selectively absorb and/or convert (into electrical signals, e.g., photoelectrically convert)) light in a first infrared wavelength region of incident light (e.g., a first infrared wavelength region including the first wavelength ($\lambda_1$)), and the second infrared light sensor 120 may be understood to be an additional sensor configured to selectively absorb and/or convert (into electrical signals, e.g., photoelectrically convert) light in a separate wavelength region of incident light (e.g., a second infrared wavelength region that is different from the first near-infrared wavelength region and includes the second wavelength ($\lambda_2$) and excludes the first wavelength ($\lambda_1$)).

As noted above with reference to FIG. 1, the photoactive layer 30, or any portion of the photoelectric device 100 and/or 100', may include the aforementioned compound, composition, and/or infrared absorber and thus may have improved sensitivity to and/or absorbance of infrared light, such that the operational performance and/or efficiency of the image sensor 700 in absorbing and/or photoelectrically converting incident infrared light into electrical signals (e.g., photoelectric conversion performance and/or efficiency) may be improved. In some example embodiments, the second infrared light sensor 120 may include the aforementioned compound, composition, and/or infrared absorber and thus may have improved sensitivity to and/or absorbance of infrared light, such that the operational performance and/or efficiency of the image sensor 700 in absorbing and/or converting incident infrared light into electrical signals (e.g., photoelectric conversion performance and/or efficiency) may be improved.

The sensor according to some example embodiments may include two infrared light sensors respectively performing separately functions and thus may work as a combination sensor. In some example embodiments, two sensors performing separately functions are stacked in each pixel, and thus the number of pixel performing functioning of each sensor is twice increased while maintaining a size and resultantly, sensitivity may be much improved.

The aforementioned sensor may be applied to various electronic devices, for example and the electronic devices may include for example a camera, a camcorder, a mobile phone internally having them, a display device, a security device, or a medical device, but are not limited thereto.

Figure 9:
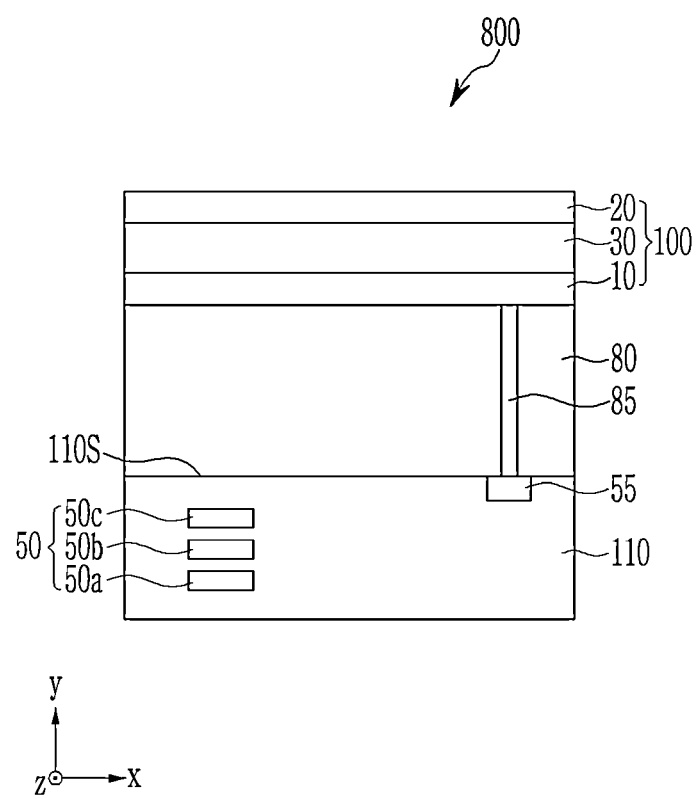
FIG. 9 is a cross-sectional view showing an image sensor according to some example embodiments.

FIG. 9 is a cross-sectional view showing an image sensor according to some example embodiments.

Referring to FIG. 9, the image sensor 800 according to some example embodiments includes the visible light sensor 50, and the photoelectric device 100 like that of some example embodiments. As shown in FIG. 9, the visible light sensor 50 includes a red photo-sensing device 50a, a green photo-sensing device 50b, and a blue photo-sensing device 50c integrated in (e.g., at least partially embedded within) the semiconductor substrate 110, wherein the red photo-sensing device 50a, the green photo-sensing device 50b, and the blue photo-sensing device 50c may be photodiodes and may be configured to selectively absorb light in separate visible wavelength regions.

In the image sensor 800 according to some example embodiments, the red photo-sensing device 50a, the green photo-sensing device 50b, and the blue photo-sensing device 50c integrated in the semiconductor substrate 110 are stacked (e.g., overlap with each other) in a vertical direction (e.g., the y direction, extending perpendicular to the upper surface 110S of the semiconductor substrate 110) and overlap with the photoelectric device 100 in the vertical direction. The red photo-sensing device 50a, the green photo-sensing device 50b, and the blue photo-sensing device 50c may be configured to selectively absorb and/or convert (into electrical signals, e.g., photoelectrically convert) light in each wavelength region depending on a stacking depth from the upper surface 110S and thus sense it. In other words, the red photo-sensing device 50a configured to selectively absorb and/or convert (into electrical signals, e.g., photoelectrically convert) red light in a long wavelength region is disposed deeper from the upper surface 110S of the semiconductor substrate 110 than the blue photo-sensing device 50c configured to selectively absorb and/or convert (into electrical signals, e.g., photoelectrically convert) blue light in a short wavelength region, and the green photo-sensing device 50b configured to selectively absorb and/or convert (into electrical signals, e.g., photoelectrically convert) green light in a medium wavelength region is disposed deeper from the upper surface 110S of the semiconductor substrate 110 than the blue photo-sensing device 50c and closer to the upper surface 110S of the semiconductor substrate 110 than the red photo-sensing device 50a. In this way, the color filters 70a, 70b, and 70c may be omitted by separating absorption wavelengths depending on the stacking depth.

Figure 10:
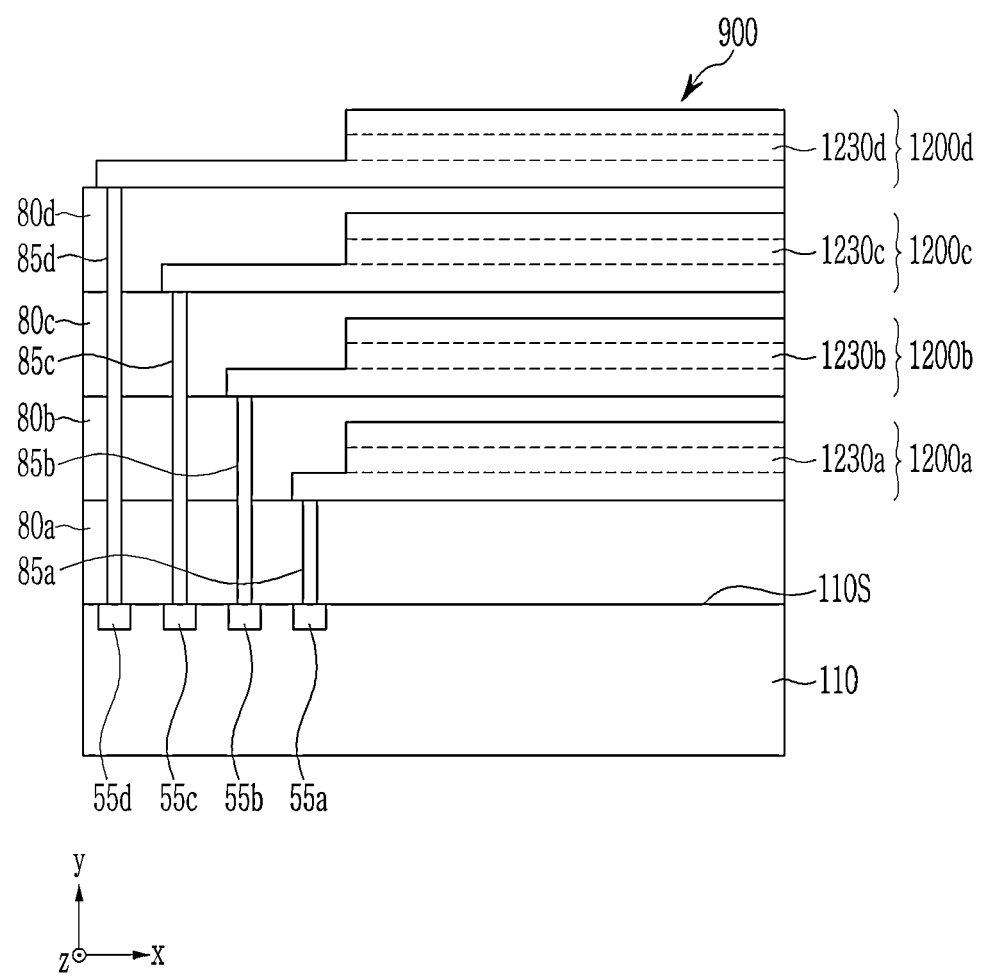
FIG. 10 is a cross-sectional view showing an image sensor according to some example embodiments.

FIG. 10 is a cross-sectional view showing an image sensor according to some example embodiments.

Referring to FIG. 10, the image sensor 900 according to some example embodiments includes a first photoelectric device (e.g., infrared/near infrared photoelectric device 1200d) configured to selectively absorb and/or convert (into electrical signals, e.g., photoelectrically convert) light in an infrared/near infrared wavelength spectrum of incident light (e.g., a first infrared wavelength region), and at least one additional photoelectric device (e.g., 1200a to 1200c) vertically stacked (e.g., in the vertical direction extending perpendicular to the upper surface 110S of the semiconductor substrate 110) between the first photoelectric device and a semiconductor substrate (e.g., 110), each separate photoelectric device of the at least one additional photoelectric device (e.g., 1200a to 1200c) including a separate photoelectric conversion layer and configured to selectively absorb and/or convert (into electrical signals, e.g., photoelectrically convert) a separate (e.g., respective) wavelength region of incident light that is different from the first infrared wavelength region and which may be a separate visible and/or non-visible wavelength region. For example, as shown in FIG. 10, the image sensor 900 may include additional photoelectric devices 1200a to 1200c that include a red photoelectric device 1200a configured to selectively absorb and/or convert (into electrical signals, e.g., photoelectrically convert) light in a red wavelength spectrum of incident light, a green photoelectric device 1200b configured to selectively absorb and/or convert (into electrical signals) light in a green wavelength spectrum of incident light, and a blue photoelectric device 1200c configured to selectively absorb and/or convert (into electrical signals) light in a blue wavelength spectrum of incident light, and they are stacked in the vertical direction that extends perpendicular to the upper surface 110S of the semiconductor substrate 110 (e.g., y direction).

Accordingly, it will be understood that, as shown in FIG. 10, the image sensor 900 may include a plurality of photoelectric devices 1200a-1200d that are stacked vertically on the semiconductor substrate 110, such that the plurality of photoelectric devices 1200a-1200d overlap each other in a direction extending perpendicular to an upper surface 110S of the semiconductor substrate 110. While the image sensor 900 includes multiple additional photoelectric devices 1200a to 1200c in addition to the first photoelectric device (e.g., fourth photoelectric device 1200d) configured to selectively absorb and/or convert light in the first near-infrared wavelength region, it will be understood that in some example embodiments the image sensor 900 may be limited to a single additional photoelectric device (e.g., any of 1200a to 1200c) between the photoelectric device 1200d and the semiconductor substrate 110.

The image sensor 900 according to some example embodiments includes a semiconductor substrate 110, a lower insulation layer 80a, an intermediate insulation layer 80*b*, another intermediate insulation layer 80*c*, an upper insulation layer 80*d*, a first photoelectric device 1200*a*, a second photoelectric device 1200*b*, a third photoelectric device 1200*c*, and a fourth photoelectric device 1200*d*. Each given photoelectric device of the first to fourth photoelectric devices 1200*a* to 1200*d* may include first and second electrodes and a photoactive layer (e.g., 1230*a* to 1230*d*, respectively) between the respective first and second electrodes of the given photoelectric device. Each given photoelectric device of the first to fourth photoelectric devices 1200*a* to 1200*d* may have a same structure and/or material composition as any of the photoelectric devices of FIGS. 1-9 according to any of the example embodiments.

In some example embodiments, the fourth photoelectric device 1200*d* may be referred to as a first photoelectric device configured to selectively absorb and/or convert (into electrical signals, e.g., photoelectrically convert) light in a first near-infrared wavelength region, and the first to third photoelectric devices 1200*a* to 1200*c* may be collectively referred to as at least one additional photoelectric device configured to selectively absorb and/or convert (into electrical signals, e.g., photoelectrically convert) light in one or more separate wavelength regions different from the first near-infrared wavelength region. As shown, the first to fourth photoelectric devices 1200*a* to 1200*d* are stacked vertically on the semiconductor substrate 110, such that the first to fourth photoelectric devices 1200*a* to 1200*d* overlap each other in a direction extending perpendicular to an upper surface 110S of the semiconductor substrate 110.

The semiconductor substrate 110 may be a silicon substrate, and is integrated with the transmission transistor (not shown) and charge storages.

The first through third photoelectric devices 1200*a* to 1200*c* may have a same structure as any of the photoelectric devices according to any of the example embodiments herein, including without limitation the photo-sensing devices 100B, 100G, and 100R shown in any of FIGS. 5-7, except each separate photoelectric device 1200*a* to 1200*c* may be configured to photoelectrically convert a separate wavelength region of visible and/or non-visible (e.g., near-infrared) light, and the respective photoelectric conversion layers 1230*a* to 1230*c* of the first to third photoelectric devices 1200*a* to 1200*c* may have a same structure as any of the photoelectric devices according to any of the example embodiments herein, including without limitation the photoelectric device 100 of FIGS. 1 and 3-4, the photoelectric device 100' of FIG. 2, the photo-sensing devices 100B, 100G, 100R, and/or 100IR shown in any of FIGS. 5-7 and/or the first infrared light sensor 100A shown in FIG. 8. The photoelectric conversion layer 1230*d* may have a same structure and/or composition as the photoactive layer according to any of the example embodiments as described herein, including the photoactive layer 30, 30B, 30G, 30R, and/or 30IR as described herein so as to be configured to selectively absorb and/or convert (into electrical signals, e.g., photoelectrically convert) different visible and/or non-visible wavelength regions of light, and may include the compound, composition, and/or infrared absorber.

The fourth photoelectric device 1200*d* may have a same structure as any of the photoelectric devices according to any of the example embodiments herein, including without limitation the photoelectric device 100 of FIGS. 1 and 3-4, the photoelectric device 100' of FIG. 2, the additional photoelectric devices 100B, 100G, 100R, and/or 100IR shown in any of FIGS. 5-7 and/or the first infrared light sensor 100A shown in FIG. 8. The photoelectric conversion layer 1230*d* may have a same structure and/or composition as the photoactive layer according to any of the example embodiments as described herein, including the photoactive layer 30, 30B, 30G, 30R, and/or 30IR as described herein so as to be configured to selectively absorb and/or convert (into electrical signals, e.g., photoelectrically convert) different visible and/or non-visible wavelength regions of light, and may include the compound, composition, and/or infrared absorber.

The first photoelectric device 1200*a* is formed on the lower insulation layer 80*a*. The first photoelectric device 1200*a* includes a photoelectric conversion layer 1230*a*. The first photoelectric device 1200*a* may be any one of the photoelectric devices described herein according to any of the example embodiments. The photoelectric conversion layer 1230*a* may selectively absorb and/or convert (into electrical signals, e.g., photoelectrically convert) light in one of infrared, red, blue, and green wavelength spectra of incident light. For example, the first photoelectric device 1200*a* may be a blue photoelectric device.

An intermediate insulation layer 80*b* is formed on the first photoelectric device 1200*a*.

The second photoelectric device 1200*b* is formed on the intermediate insulation layer 80*b*. The second photoelectric device 1200*b* includes a photoelectric conversion layer 1230*b*. The second photoelectric device 1200*b* may be any one of the photoelectric devices described herein according to any of the example embodiments. The photoelectric conversion layer 1230*b* may selectively absorb and/or convert (into electrical signals, e.g., photoelectrically convert) light in one of infrared, red, blue, or green wavelength spectra of incident light. For example, the second photoelectric device 1200*b* may be a green photoelectric device.

Another intermediate insulation layer 80*c* is formed on the second photoelectric device 1200*b*.

The third photoelectric device 1200*c* is formed on the intermediate insulation layer 80*c*. The third photoelectric device 1200*c* includes a photoelectric conversion layer 1230*c*. The third photoelectric device 1200*c* may be any one of the photoelectric devices described herein according to any of the example embodiments. The photoelectric conversion layer 1230*c* may selectively absorb and/or convert (into electrical signals, e.g., photoelectrically convert) light in one of infrared, red, blue, or green wavelength spectra of incident light. For example, the third photoelectric device 1200*c* may be a red photoelectric device.

The upper insulation layer 80*d* is formed on the third photoelectric device 1200*c*.

The lower insulation layer 80*a*, the intermediate insulation layers 80*b* and 80*c*, and the upper insulation layer 80*d* have a plurality of through holes, or trenches 85*a*, 85*b*, 85*c*, and 85*d* exposing the charge storages 55*a*, 55*b*, 55*c*, and 55*d*, respectively, and said trenches may be partly or completely filled with a filler material (e.g., fillers).

The fourth photoelectric device 1200*d* is formed on the upper insulation layer 80*d*. The fourth photoelectric device 1200*d* includes a photoelectric conversion layer 1230*d*. The fourth photoelectric device 1200*d* may be any one of the photoelectric devices described herein according to any of the example embodiments. The photoelectric conversion layer 1230*d* may selectively absorb and/or convert (into electrical signals, e.g., photoelectrically convert) light in one of infrared, red, blue, or green wavelength spectra of light. For example, the fourth photoelectric device 1200*d* may be an infrared/near infrared photoelectric device that may include the infrared absorber.

In FIG. 10, the first photoelectric device 1200*a*, the second photoelectric device 1200*b*, the third photoelectric device 1200*c*, and the fourth photoelectric device 1200*d* are sequentially stacked, but the present disclosure is not limited thereto, and they may be stacked in various orders.

As described above, the first photoelectric device 1200*a*, the second photoelectric device 1200*b*, the third photoelectric device 1200*c*, and the fourth photoelectric device 1200*d* have a stack structure, and thus the size of an image sensor may be reduced to realize a down-sized image sensor.

Figure 11:
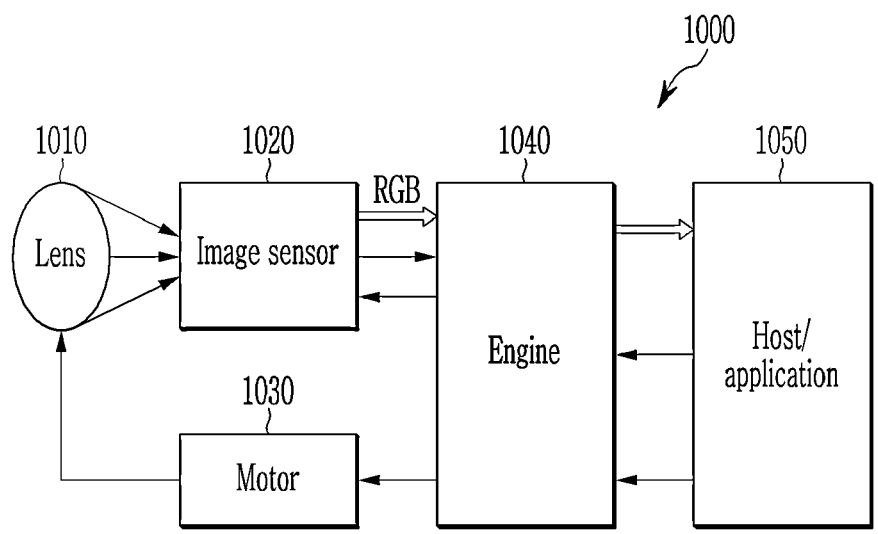
FIG. 11 is a block diagram of a digital camera including an image sensor according to some example embodiments.

FIG. 11 is a block diagram of a digital camera including an image sensor according to some example embodiments.

Referring to FIG. 11, a digital camera 1000 includes a lens 1010, an image sensor 1020, a motor 1030, and an engine 1040. The image sensor 1020 may be one of image sensors according to any of the example embodiments, including the example embodiments shown in FIGS. 3 to 10.

The lens 1010 concentrates incident light on the image sensor 1020. The image sensor 1020 generates RGB data for received light through the lens 1010.

In some example embodiments, the image sensor 1020 may interface with the engine 1040.

The motor 1030 may adjust the focus of the lens 1010 or perform shuttering in response to a control signal received from the engine 1040. The engine 1040 may control the image sensor 1020 and the motor 1030.

The engine 1040 may be connected to a host/application 1050.

Figure 12:
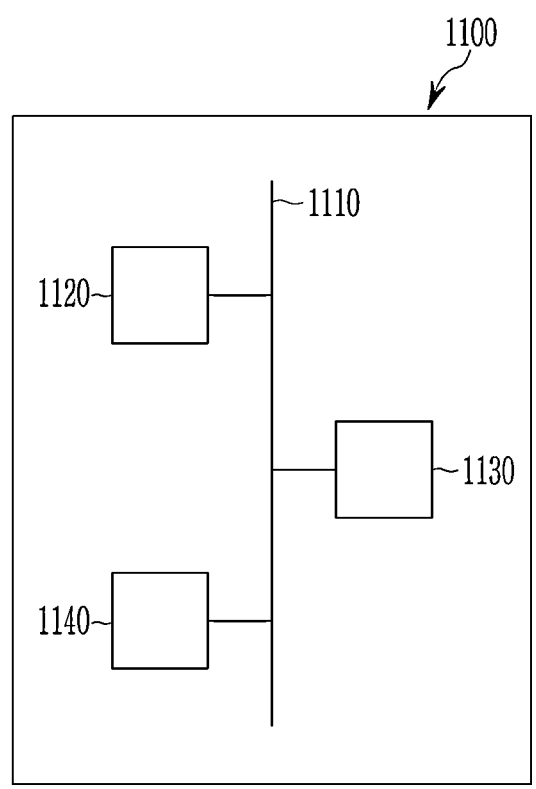
FIG. 12 is a block diagram of an electronic device according to some example embodiments.

FIG. 12 is a block diagram of an electronic device according to some example embodiments. Referring to FIG. 12, an electronic device 1100 may include a processor 1120, a memory 1130, and an image sensor 1140 that are electrically coupled together via a bus 1110. The image sensor 1140 may be an image sensor according to any of the example embodiments, including the example embodiments shown in FIGS. 3 to 11. The memory 1130, which may be a non-transitory computer readable medium, may store a program of instructions and/or other information. The memory 1130 may be a nonvolatile memory, such as a flash memory, a phase-change random access memory (PRAM), a magneto-resistive RAM (MRAM), a resistive RAM (ReRAM), or a ferro-electric RAM (FRAM), or a volatile memory, such as a static RAM (SRAM), a dynamic RAM (DRAM), or a synchronous DRAM (SDRAM). The processor 1120 may execute the stored program of instructions to perform one or more functions. For example, the processor 1120 may be configured to process electrical signals generated by the image sensor 1140. The processor 1120 may be configured to generate an output (e.g., an image to be displayed on a display interface) based on such processing.

The processor 1120 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc. The processor 1120 may be configured to generate an output (e.g., an image to be displayed on a display interface) based on such processing.

One or more of the processor 1120, memory 1130, motor 1030, engine 1040, or host/application 1050 may be included in, include, and/or implement one or more instances of processing circuitry such as hardware including logic circuits, a hardware/software combination such as a processor executing software; or a combination thereof. In some example embodiments, said one or more instances of processing circuitry may include, but are not limited to, a central processing unit (CPU), an application processor (AP), an arithmetic logic unit (ALU), a graphic processing unit (GPU), a digital signal processor, a microcomputer, a field programmable gate array (FPGA), a System-on-Chip (SoC) a programmable logic unit, a microprocessor, or an application-specific integrated circuit (ASIC), etc. In some example embodiments, any of the memories, memory units, or the like as described herein may include a non-transitory computer readable storage device, for example a solid state drive (SSD), storing a program of instructions, and the one or more instances of processing circuitry may be configured to execute the program of instructions to implement the functionality of some or all of any of the processor 1120, memory 1130, motor 1030, engine 1040, or host/application 1050, or the like according to any of the example embodiments as described herein.

Hereinafter, some example embodiments are illustrated in more detail with reference to examples. However, the present scope of the inventive concepts is not limited to these examples.

Synthesis Examples

Synthesis Example 1: Synthesis of Compound Represented by Chemical Formula 1-1 (Compound (6))

[Chemical Formula 1-1]

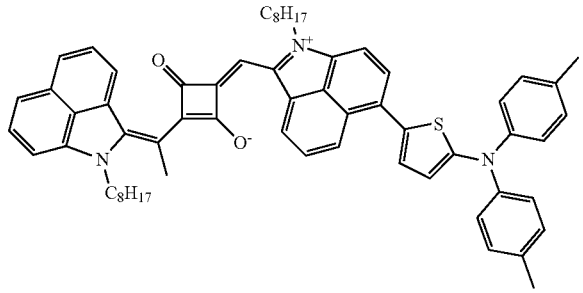

[Reaction Scheme 1-1a]

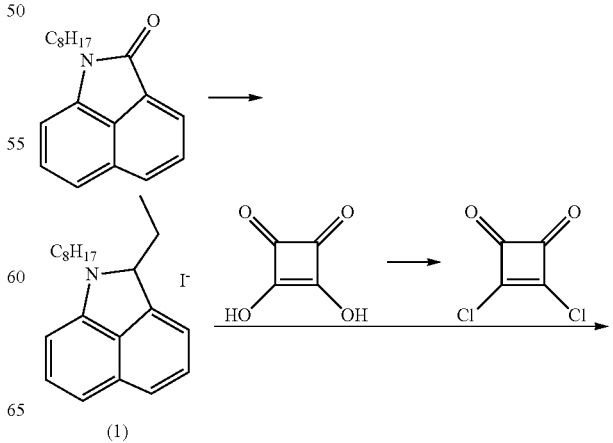

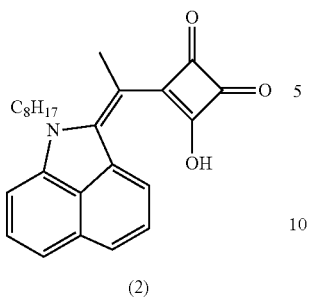

(2)

[Reaction Scheme 1-1b]

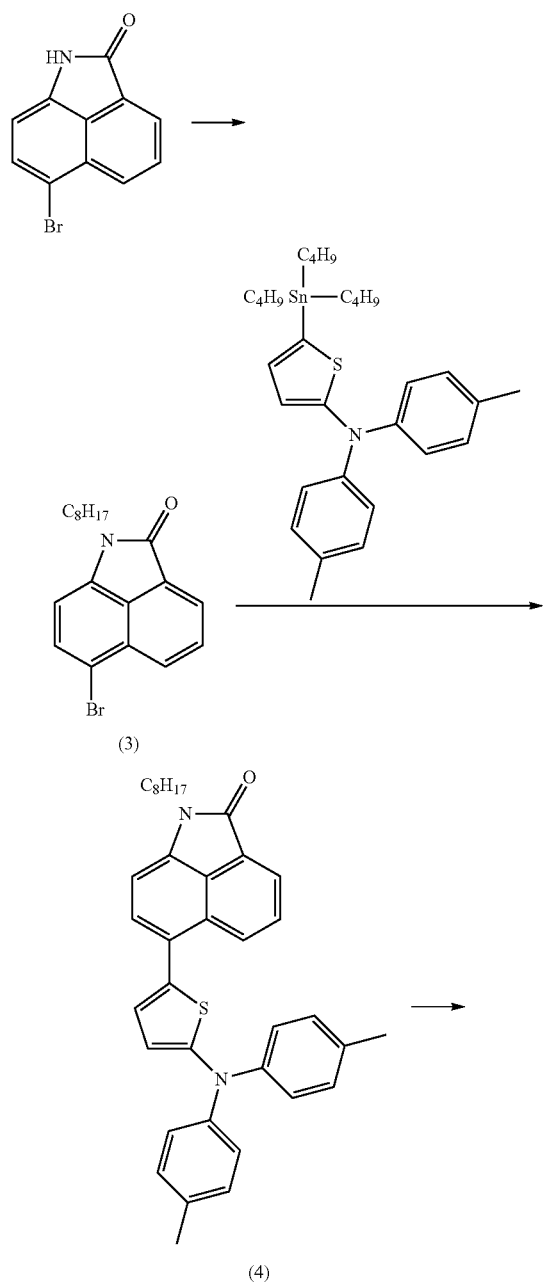

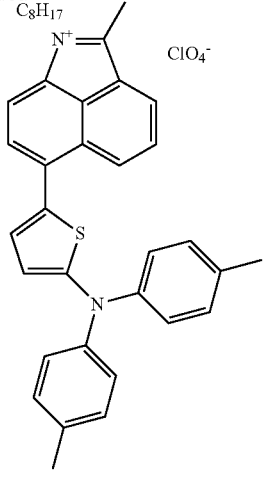

(5)

[Reaction Scheme 1-1c]

(2) + (5) ⟶

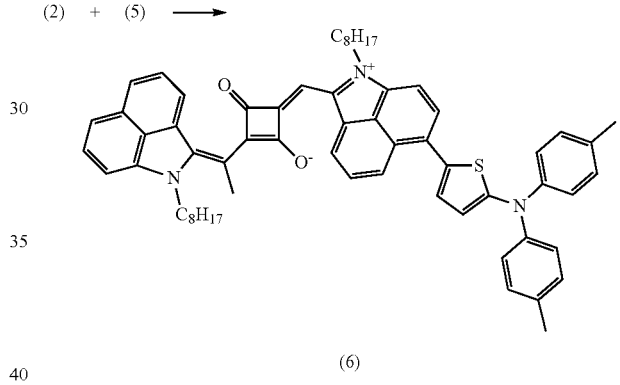

(6)

i) First Step: Synthesis of Compound (1)

An ethylmagnesium bromide solution (3 M in diethyl ether) (7.1 mL, 21.3 mmol) is slowly added to a solution in which 1-octylbenzo[cd]indol-2(1H)-one (2.0 g, 7.1 mmol) is dissolved in 10 mL of dry tetrahydrofuran (dry THF) and then, stirred at 60° C. for 6 hours. Subsequently, 20 mL of 1N HCl is slowly added thereto at 0° C., and after evaporating THF, the remaining solution is poured into a KI (2.36 g, 14.2 mmol, in 20 mL of $H_2O$) solution. Then, precipitates obtained therefrom are filtered to obtain Compound (1) (1.8 g, Yield: about 60%).

LC-MS: 294.21 m/z confirmation of molecular weight.

ii) Second Step: Synthesis of Compound (2)

Squaric acid (0.26 g, 2.3 mmol), thionyl chloride (1 M in MC, 4.5 mL, 4.5 mmol), and dimethyl formamide (DMF, 0.04 g, 0.6 mmol) are added to toluene (8 mL) and then, stirred at 95° C. for 3 hours. Subsequently, after evaporating the thionyl chloride, Compound (1) (0.32 g, 0.8 mmol) is added thereto at room temperature and then, stirred for 1 hour. Then, triethylamine (0.76 g, 7.5 mmol), $H_2O$ (0.55 g, 7.5 mmol), and acetone (6 mL) are added thereto and then, continuously stirred at room temperature. After 12 hours, 30 mL of $H_2O$ is added thereto to dissolve the materials, and an undissolved portion thereof is removed with a filter. Finally, 10 mL of 2N HCl is used to make pH thereof into 2, and methylene chloride (MC) is used for an extraction. A product therefrom is separated and purified through silica gel column chromatography (ethylacetate (EA): n-hexane (n-Hex)=1:1 v/v) to obtain Compound (2) (0.2 g, Yield: about 68%).

LC-MS: 390.28 m/z confirmation of molecular weight.

iii) Third Step: Synthesis of Compound (3)

6-bromobenzo[cd]indol-2(1H)-one (3 g, 12.1 mmol) is dissolved in 60 mL of DMF, and NaH (60% in mineral oil, 0.73 g, 18.0 mmol) is slowly added thereto and then, stirred at 0° C. After 1 hour, 1-bromooctane (4.7 g, 24.2 mmol) is added thereto and then, stirred at room temperature for 12 hours. When a reaction is completed, the resultant is extracted with EA and then, separated and purified through silica gel column chromatography (EA: n-Hex=1:10 v/v) to obtain Compound (3) (3.8 g, Yield: about 88%).

LC-MS: 360.10 m/z confirmation of molecular weight.

iv) Fourth Step: Synthesis of Compound (4)

N,N-di-p-tolyl-5-(tributylstannyl)thiophen-2-amine (3.0 g, 5.3 mmol), Compound (3) (1.9 g, 5.3 mmol), and tetrakis(triphenylphosphine)palladium (0) (5 mol %) are dissolved in 125 mL of toluene and then, stirred at 110° C. for 18 hours. When a reaction is completed, after concentrating the toluene, the resultant is separated and purified through silica gel column chromatography (EA: n-Hex=1:10 v/v) to obtain Compound (4) (2.5 g, Yield: about 85%).

LC-MS: 559.24 m/z confirmation of molecular weight.

v) Fifth Step: Synthesis of Compound (5)

A methyl magnesium chloride solution (3 M in THF, 0.78 mL, 2.3 mmol) is slowly added to a solution in which Compound (4) (1.0 g, 1.8 mmol) is dissolved in dry tetrahydrofuran (dry THF, 6 mL) and then, stirred at 60° C. for 6 hours. Subsequently, the resultant is extracted with EA at 0° C., and 5 mL of H$_2$O and 1.5 mL of perchloric acid are sequentially slowly added thereto. Finally, a product therefrom is extracted with EA and then, precipitated in hexane and filtered to obtain Compound (5) (0.9 g, Yield: about 76%).

LC-MS: 557.25 m/z confirmation of molecular weight.

vi) Sixth Step: Synthesis of Compound Represented by Chemical Formula 1-1 (Compound (6))

Compound (2) (0.040 g, 0.1 mmol) and Compound (5) (0.067 g, 0.1 mmol) are dissolved in a mixed solvent of 1-butanol (3 mL) and toluene (3 mL) and then, stirred at 80° C. for 1 hour. When a reaction is completed, after removing the solvent, the resultant is separated and purified through silica gel column chromatography (EA: n-Hex=1:2 v/v) to obtain Compound (6) (0.03 g, Yield: about 31%).

LC-MS: 928.54 m/z confirmation of molecular weight.

Synthesis Example 2: Synthesis of Compound Represented by Chemical Formula 1-2 (Compound (10))

[Chemical Formula 1-2]

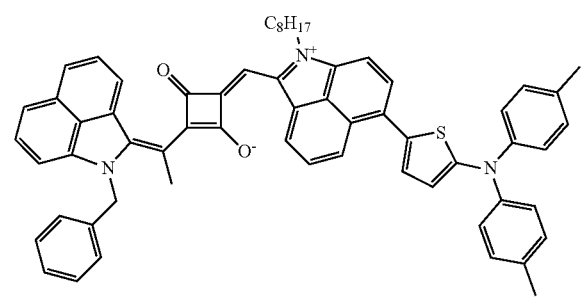

[Reaction Scheme 1-2]

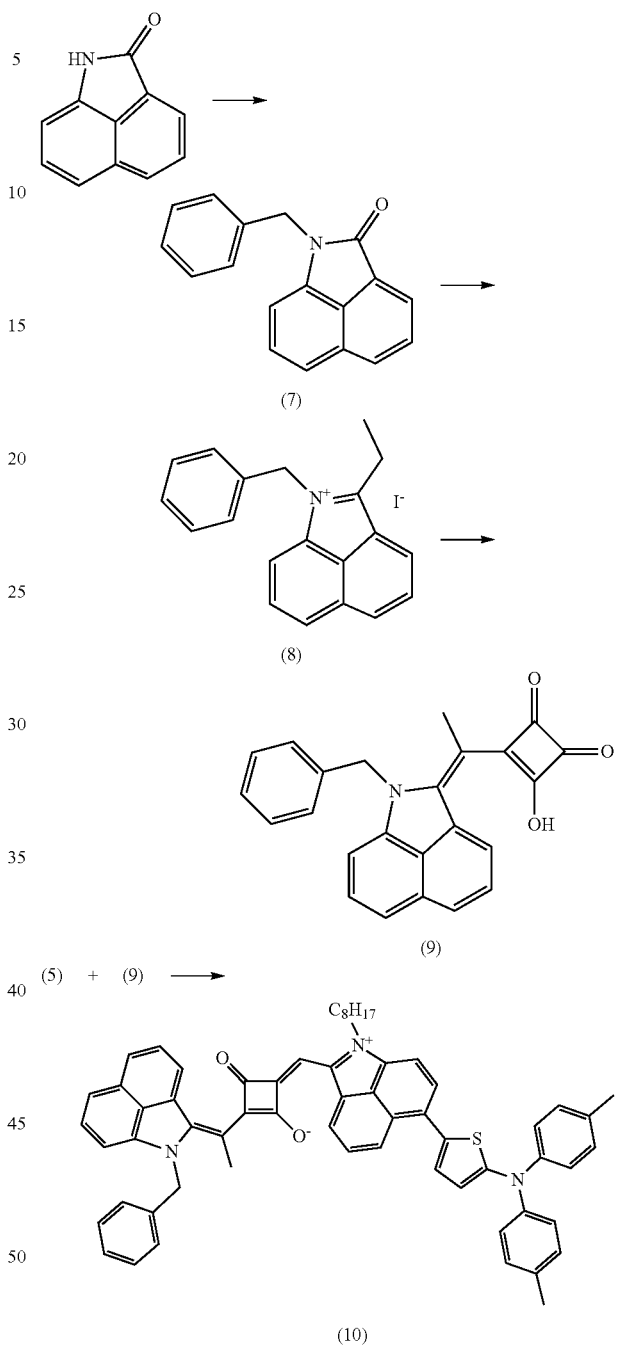

i) First Step: Synthesis of Compound (7)

Benzo[cd]indol-2(1H)-one (1 g, 5.9 mmol) is dissolved in 24 mL of DMF, and NaH (60% in mineral oil, 0.36 g, 8.9 mmol) is slowly added thereto at 0° C. and then, stirred. After 1 hour, benzyl bromide (2.0 g, 11.8 mmol) is added thereto at room temperature and then, stirred for 12 hours. When a reaction is completed, the resultant is extracted with EA and then, separated and purified through silica gel column chromatography (EA: n-Hex=1:10 v/v) to obtain Compound (7) (1.5 g, Yield: about 98%).

LC-MS: 260.13 m/z confirmation of molecular weight.

ii) Second Step: Synthesis of Compound (8)

An ethylmagnesium bromide solution (3 M in diethyl ether, 5.8 mL, 17.4 mmol) is slowly added to a solution in which Compound (7) (1.5 g, 5.8 mmol) is dissolved in 10 mL of dry THF and then, stirred at 60° C. for 6 hours. Subsequently, 20 mL of 1N HCl is slowly added thereto at 0° C., and after evaporating THF, the remaining solution is poured into a KI (1.92 g, 11.6 mmol, in 20 mL of $H_2O$) solution. Then, precipitates therefrom are filtered to obtain Compound (8) (0.9 g, Yield: about 40%).

LC-MS: 272.11 m/z confirmation of molecular weight.

iii) Third Step: Synthesis of Compound (9)

Squaric acid (0.26 g, 2.3 mmol), thionyl chloride (1 M in MC, 4.5 mL, 4.5 mmol), and DMF (0.04 g, 0.6 mmol) are added to 8 mL of toluene and then, stirred at 95° C. for 3 hours. Subsequently, after evaporating the thionyl chloride, Compound (8) (0.3 g, 0.8 mmol) is added thereto at room temperature and then, stirred for 1 hour. Then, triethylamine (0.76 g, 7.5 mmol), $H_2O$ (0.55 g, 7.5 mmol), and 6 mL of acetone are added thereto and then, continuously stirred at room temperature. After 12 hours, 30 mL of $H_2O$ is added thereto to dissolve the materials, and an undissolved portion thereof is removed with a filter. Finally, 10 mL of 2N HCl is used to make pH thereof into 2, and MC is used for an extraction. A product therefrom is separated and purified through silica gel column chromatography (EA n-Hex=1:1 v/v) to obtain Compound (9) (0.2 g, Yield: about 72%).

LC-MS: 368.15 m/z confirmation of molecular weight.

iv) Fourth Step: Synthesis of Compound Represented by Chemical Formula 1-2 (Compound (10))

Compound (5) (0.067 g, 0.1 mmol) and Compound (9) (0.038 g, 0.1 mmol) are dissolved in a mixed solvent of 1-butanol (3 mL) and toluene (3 mL) and then, stirred at 80° C. for 1 hour. When a reaction is completed, after removing the solvent, the resultant is separated and purified through silica gel column chromatography (EA: n-Hex=1:2 v/v) to obtain Compound (10) (0.02 g, Yield: about 21%).

LC-MS: 906.58 m/z confirmation of molecular weight.

Synthesis Example 3: Synthesis of Compound Represented by Chemical Formula 1-3 (Compound (19))

[Reaction Scheme 1-3a]

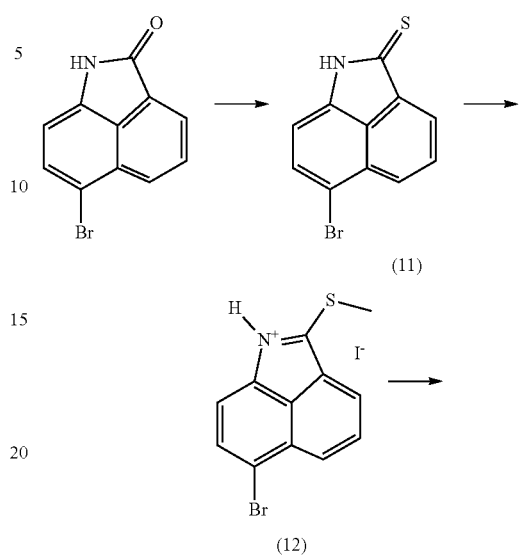

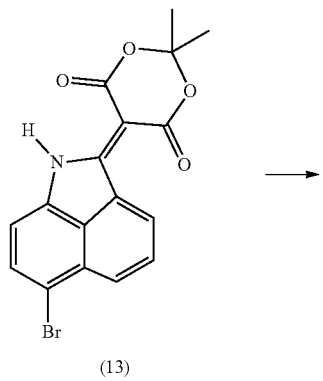

[Chemical Formula 1-3]

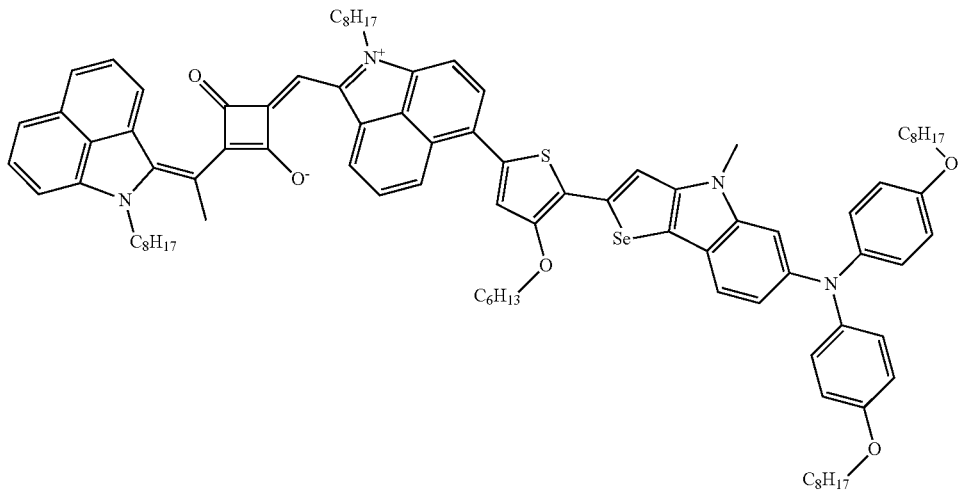

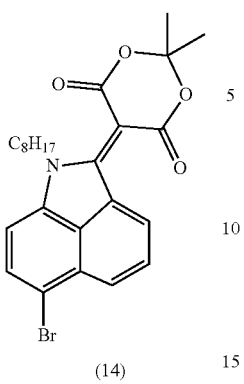
(14)
[Reaction Scheme 1-3b]
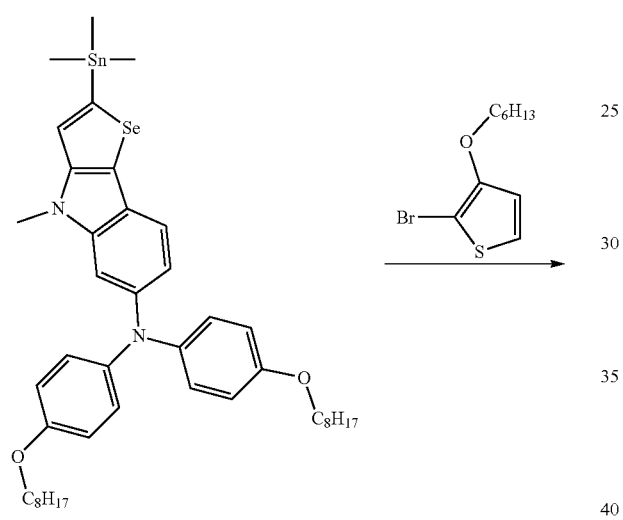
(15)
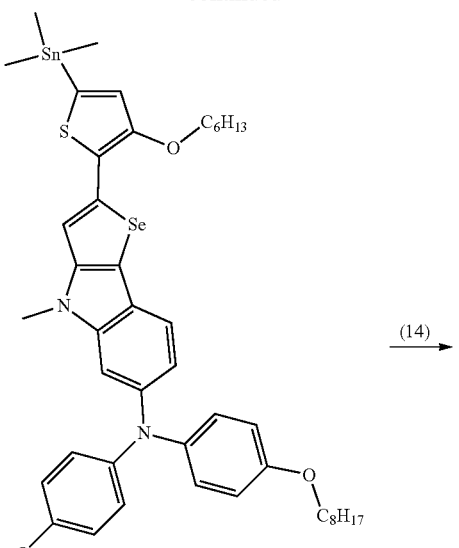
(16)
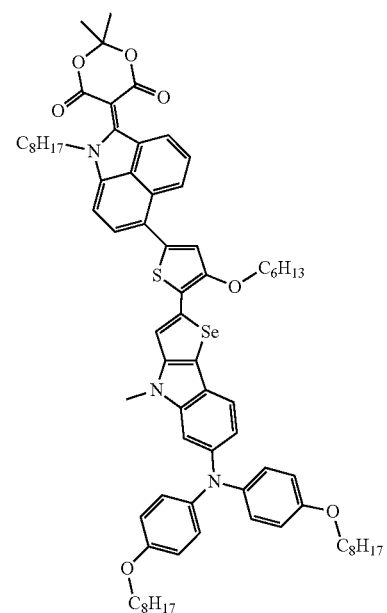
(17)

[Reaction Scheme 1-3c]

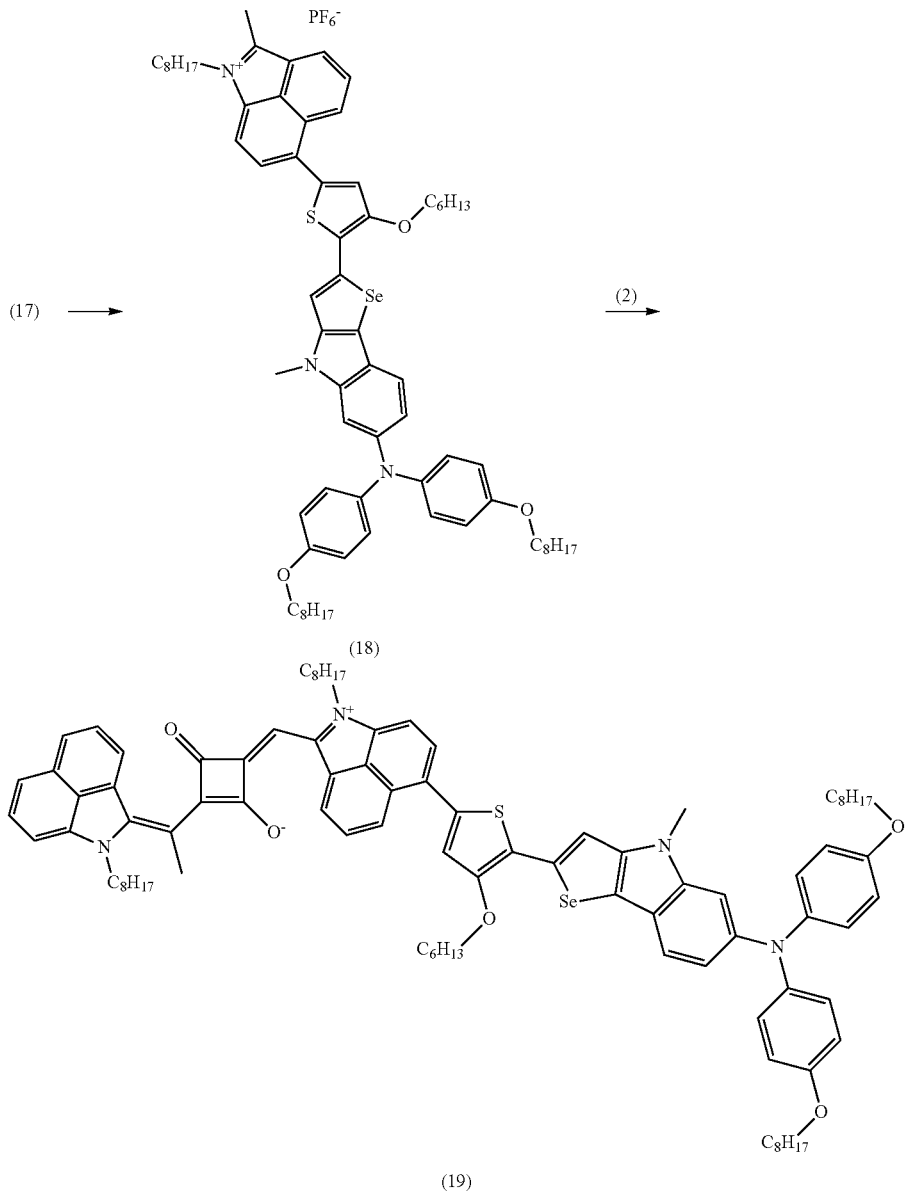

First Step: Synthesis of Compound (11)

6-bromobenzo[cd]indol-2(1H)-one (6.1 g, 24.7 mmol) and a Lawesson reagent (5.0 g, 12.4 mmol) are dissolved in 250 mL of toluene and then, stirred at 110° C. for 12 hours. Subsequently, the temperature is decreased down to room temperature, and after evaporating the toluene, a product therefrom is precipitated in H₂O to obtain Compound (11) (5.3 g, Yield: about 82%).

LC-MS: 263.85 m/z confirmation of molecular weight.

ii) Second Step: Synthesis of Compound (12)

Compound (11) (2 g, 7.6 mmol) and iodomethane (1.3 g, 9.1 mmol) are dissolved in 10 mL of 1N NaOH and 50 mL of THF and then, stirred at room temperature. After 1 hour, EA is used for an extraction and evaporated to obtain Compound (12) (3 g, Yield: about 98%).

iii) Third Step: Synthesis of Compound (13)

Compound (12) (3 g, 7.4 mmol), Meldrum's acid (2 g, 13.9 mmol), and sodium acetate (1.14 g, 13.9 mmol) are dissolved in 60 mL of ethanol and then, stirred at 80° C. for 2 hours. A product therefrom is cooled down to room temperature and filtered to immediately obtain Compound (13) (2.1 g, Yield: about 75%).

iv) Fourth Step: Synthesis of Compound (14)

Compound (13) (1.0 g, 2.7 mmol), 1-bromooctane (1.0 g, 5.3 mmol), and potassium carbonate (0.74 g, 5.3 mmol) are dissolved in 20 mL of DMF and then, stirred at 120° C. for 8 hours. A product therefrom is extracted with EA and then, separated and purified through silica gel column chromatography (EA: chloroform=1:40 v/v) to obtain Compound (14) (0.53 g, Yield: about 41%).

LC-MS: 488.19 m/z confirmation of molecular weight.

v) Fifth Step: Synthesis of Compound (15)

4-methyl-N,N-bis(4-(octyloxy)phenyl)-2-(trimethylstannyl)-4H-selenopheno[3,2-b]indol-6-amine (3 g, 3.7 mmol), 2-bromo-3-(hexyloxy)thiophene (1.0 g, 3.7 mmol), and tetrakis(triphenylphosphine)palladium (0) (5 mol %) are dissolved in 100 mL of toluene and then, stirred at 110° C. for 18 hours. When a reaction is completed, after evaporating the toluene, the resultant is separated and purified through silica gel column chromatography (EA: n-Hex=1:20 v/v) to obtain Compound (15) (0.9 g, Yield: about 29%).

LC-MS: 841.41 m/z confirmation of molecular weight.

vi) Sixth Step: Synthesis of Compound (16)

Compound (15) (0.9 g, 1.1 mmol) is dissolved in anhydrous THF and then, stirred at −78° C. After slowly adding 2.5 M n-BuLi (in n-Hex, 0.5 mL, 1.3 mmol) thereto and then, stirring the mixture for 3 hours, 1 M trimethyltin chloride (in THF, 1.3 mL, 1.3 mmol) is added thereto and then, heated up to room temperature. The obtained compound (Compound (16), 1.0 g, Yield: about 93%) is extracted with chloroform and then, used for the following reaction without additional purification.

LC-MS: 1005.31 m/z confirmation of molecular weight.

vii) Seventh Step: Synthesis of Compound (17)

Compound (14) (0.26 g, 0.54 mmol), Compound (16) (0.54 g, 0.54 mmol), and tetrakis(triphenylphosphine)palladium (0) (5 mol %) are dissolved in 20 mL of toluene and then, stirred at 110° C. for 18 hours. When a reaction is completed, after evaporating the toluene, the resultant is separated and purified through silica gel column chromatography (EA: chloroform=1:40 v/v) to obtain Compound (17) (0.28 g, Yield: about 42%).

LC-MS: 1248.58 m/z confirmation of molecular weight.

viii) Eighth Step: Synthesis of Compound (18)

Compound (17) (0.1 g, 0.08 mmol) is dissolved in acetic acid (5 mL), and HCl (0.2 mL) is slowly added thereto. After stirring the mixture at 70° C. for 1 hour, NaPF$_6$ (0.13 g, 0.8 mmol) in 1 mL of H$_2$O is added thereto, and precipitates obtained therefrom are filtered to obtain Compound (18) (0.09 g, Yield: about 89%).

LC-MS: 1118.54 m/z confirmation of molecular weight.

ix) Ninth Step: Synthesis of Compound Represented by Chemical Formula 1-3 (Compound (19))

Compound (2) (0.020 g, 0.05 mmol) and Compound (18) (0.065 g, 0.05 mmol) are dissolved in a mixed solvent of 1-butanol (3 mL) and toluene (3 mL) and then, stirred at 80° C. for 1 hour. When a reaction is completed, after removing the solvent, the resultant is separated and purified through silica gel column chromatography (EA: n-Hex=1:2 v/v) to obtain Compound (19) (0.015 g, Yield: about 20%).

LC-MS: 1490.97 m/z confirmation of molecular weight.

Synthesis Example 4: Synthesis of Compound Represented by Chemical Formula 1-4 (Compound (22))

[Chemical Formula 1-4]

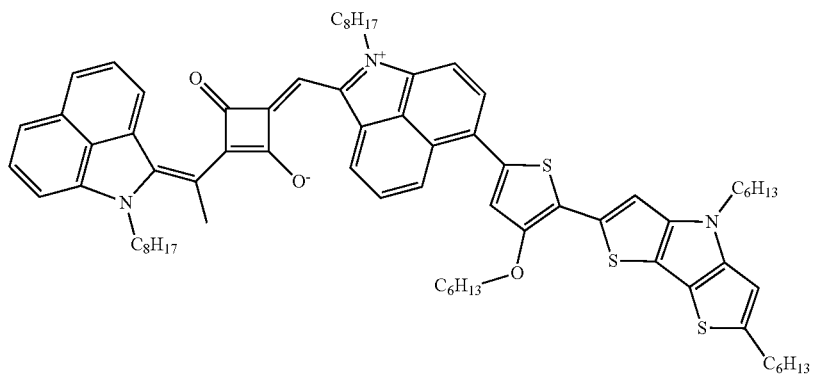

[Reaction Scheme 1-4a]

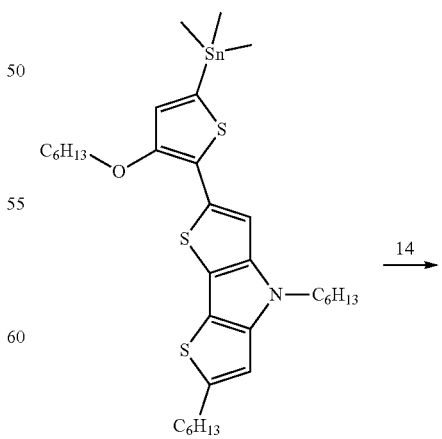

65

-continued

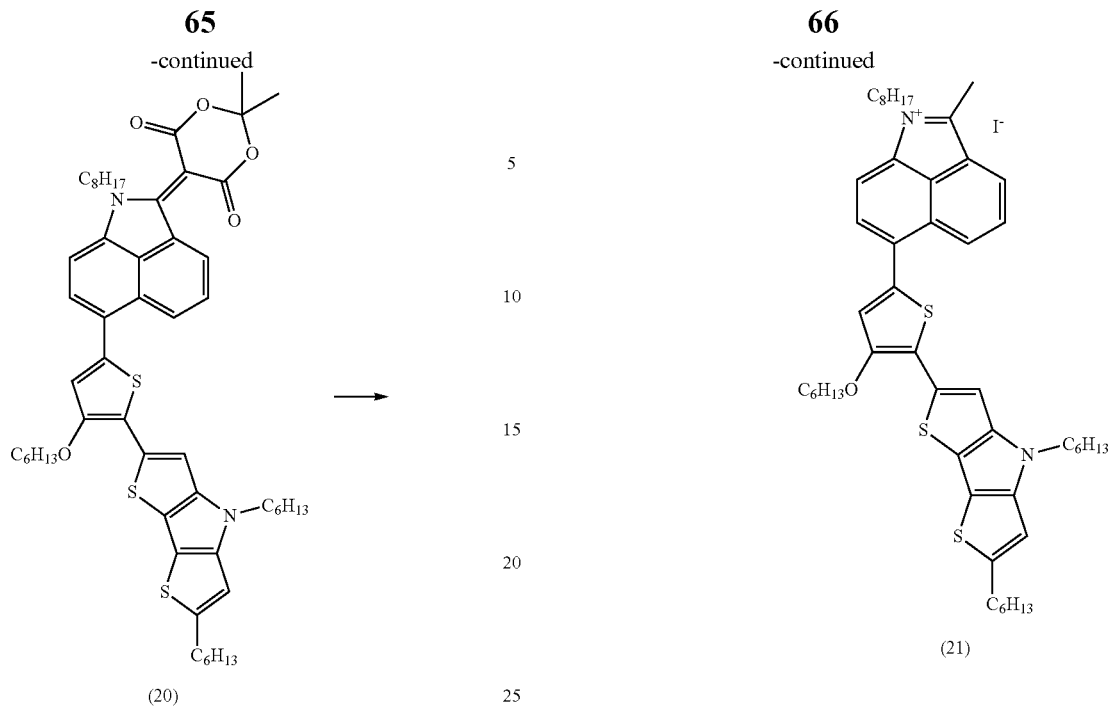

(20)

66

-continued (21)

[Reaction Scheme 1-4b]

(2) + (21) ⟶

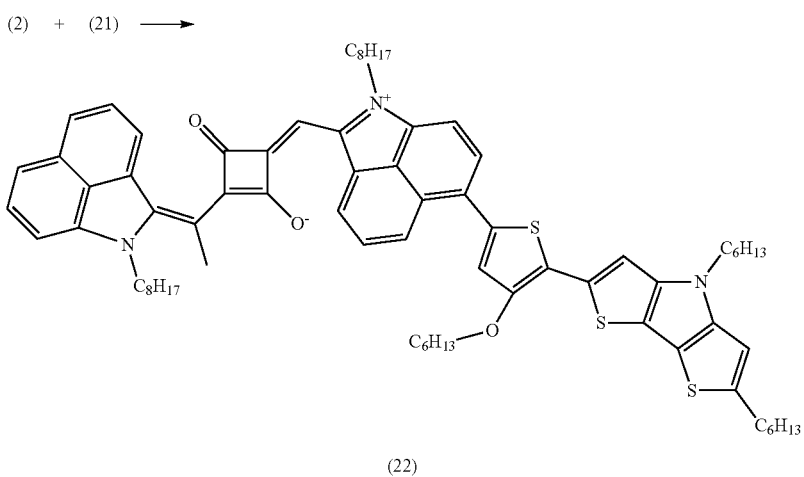

(22)

i) First Step: Synthesis of Compound (20)

2,4-dihexyl-6-(3-(hexyloxy)-5-(trimethylstannyl)thiophen-2-yl)-4H-dithieno[3,2-b:2',3'-d]pyrrole (0.37 g, 0.54 mmol), Compound (14) (0.26 g, 0.54 mmol), and tetrakis (triphenylphosphine)palladium (0) (5 mol %) are dissolved in 20 mL of toluene and then, stirred at 110° C. for 18 hours. When a reaction is completed, after evaporating the toluene, the resultant is separated and purified through silica gel column chromatography (EA: chloroform=1:40 v/v) to obtain Compound (20) (0.35 g, Yield: about 70%).

LC-MS: 937.61 m/z confirmation of molecular weight.

ii) Second Step: Synthesis of Compound (21)

Compound (20) (0.35 g, 0.37 mmol) is dissolved in 20 mL of acetic acid, and 1 mL of HCl (35%) is slowly added thereto. After stirring the obtained mixture at 70° C. for 1 hour, when KI (0.13 g, 0.8 mmol, in 10 mL of $H_2O$) is added thereto, precipitates therefrom are filtered to obtain Compound (21) (0.30 g, Yield: about 86%).

LC-MS: 807.50 m/z confirmation of molecular weight.

iii) Third Step: Synthesis of Compound Represented by Chemical Formula 1-4 (Compound (22))

Compound (2) (0.030 g, 0.08 mmol) and Compound (21) (0.072 g, 0.08 mmol) are dissolved in a mixed solvent of 1-butanol (3 mL) and toluene (3 mL) and then, stirred at 80° C. for 1 hour. When a reaction is completed, after removing the solvent, the resultant is separated and purified through silica gel column chromatography (EA: n-Hex=1:2 v/v) to obtain Compound (22) (0.03 g, Yield: about 33%).

LC-MS: 1178.48 m/z confirmation of molecular weight.

Synthesis Example 5: Synthesis of Compound Represented by Chemical Formula 1-5 (Compound (23))

[Chemical Formula 1-5]

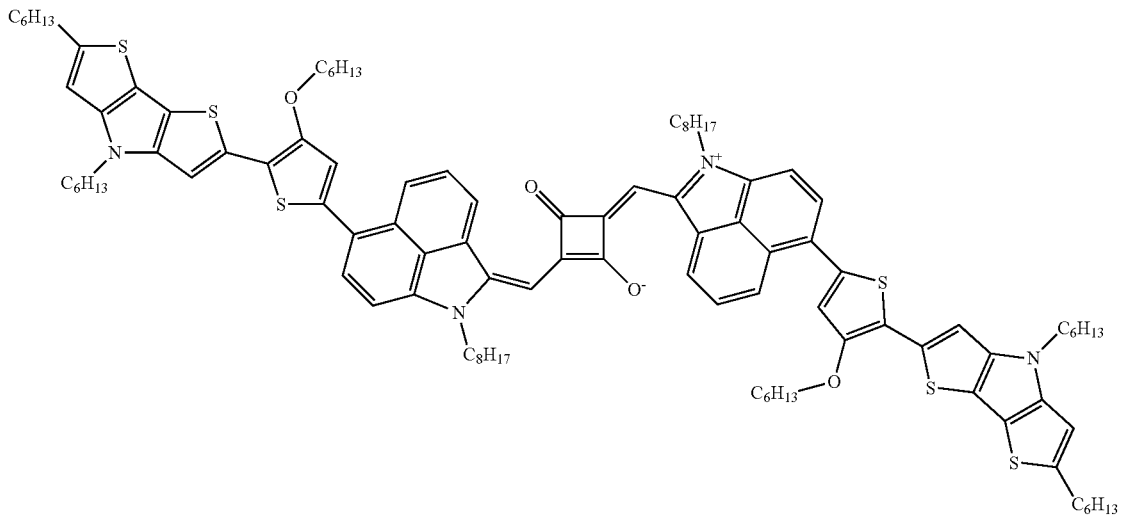

[Reaction Scheme 1-5]

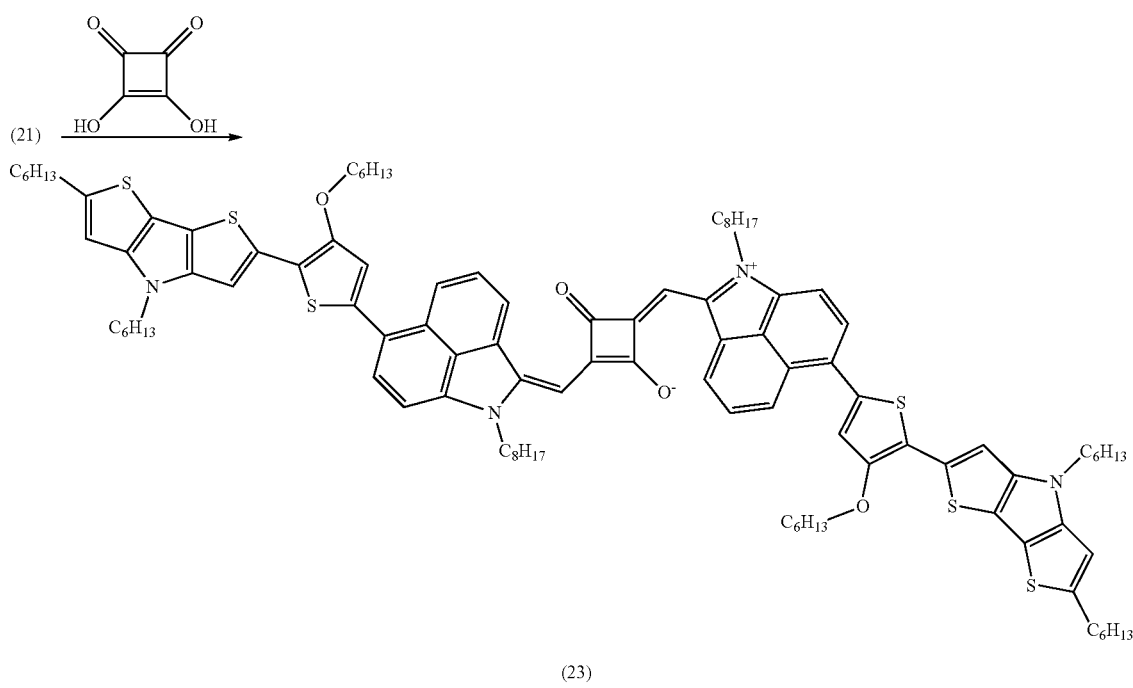

First Step: Synthesis of Compound represented by Chemical Formula 1-5 (Compound (23))

Compound (21) (0.080 g, 0.09 mmol) and squaric acid (0.005 g, 0.04 mmol) are dissolved in a mixed solvent of 1-butanol (3 mL) and toluene (3 mL) and then, stirred at 110° C. for 1 hour. When a reaction is completed, after evaporating the solvent, the resultant is separated and purified through silica gel column chromatography (EA: n-Hex=1:2 v/v) to obtain Compound (23) (0.02 g, Yield: about 28%).

LC-MS: 1692.90 m/z confirmation of molecular weight.

Synthesis Example 6: Synthesis of Compound Represented by Chemical Formula 1-6 (Compound (25))

[Chemical Formula 1-6]

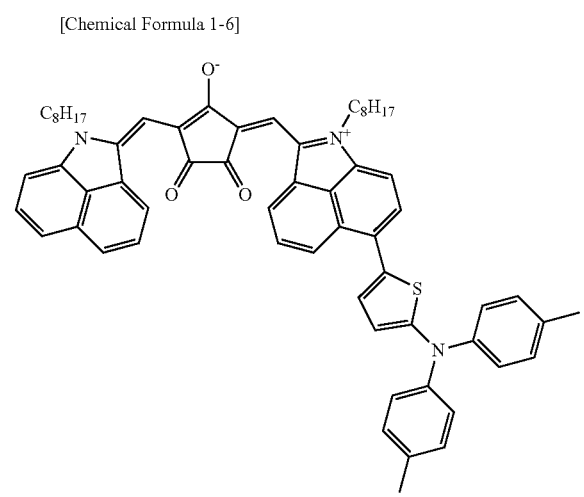

[Reaction Scheme 1-6]

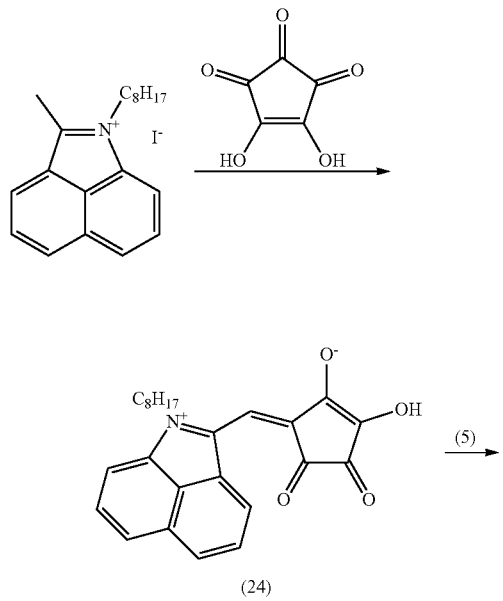

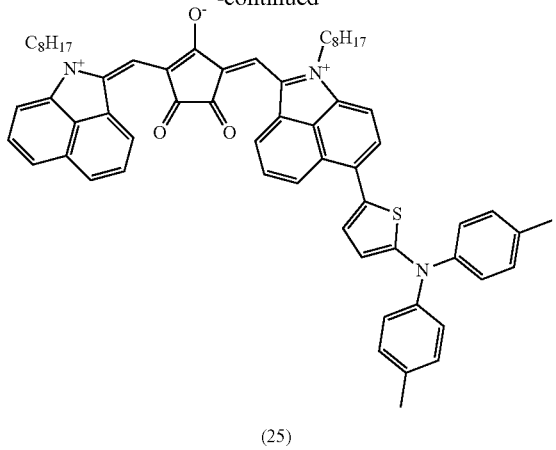

(25)

i) First Step: Synthesis of Compound (24)

2-methyl-1-octylbenzo[cd]indol-1-ium iodide (0.4 g, 1.0 mmol) and croconic acid (0.2 g, 1.4 mmol) are dissolved in a mixed solvent of acetone (6 mL) and $H_2O$ (6 mL) and then, stirred at room temperature for 72 hours. Subsequently, 40 mL of $H_2O$ is added thereto, and impurities dissolved therein are all filtered and removed. Precipitates remaining there are separated and purified through silica gel column chromatography (acetone: chloroform=1:1 v/v) to obtain Compound (24) (0.2 g, Yield: about 50%).

LC-MS: 404.20 m/z confirmation of molecular weight.

ii) Second Step: Synthesis of Compound represented by Chemical Formula 1-6 (Compound (25))

Compound (5) (0.067 g, 0.1 mmol) and Compound (24) (0.041 g, 0.1 mmol) are dissolved in a mixed solvent of 1-butanol (3 mL) and toluene (3 mL) and then, stirred at 110° C. for 1 hour. When a reaction is completed, after removing the solvent, the resultant is separated and purified through silica gel column chromatography (EA: n-Hex=1:2 v/v) to obtain Compound (25) (0.02 g, Yield: about 21%).

LC-MS: 942.68 m/z confirmation of molecular weight.

Synthesis Example 7: Synthesis of Compound Represented by Chemical Formula 1-7 (Compound (26))

[Chemical Formula 1-7]

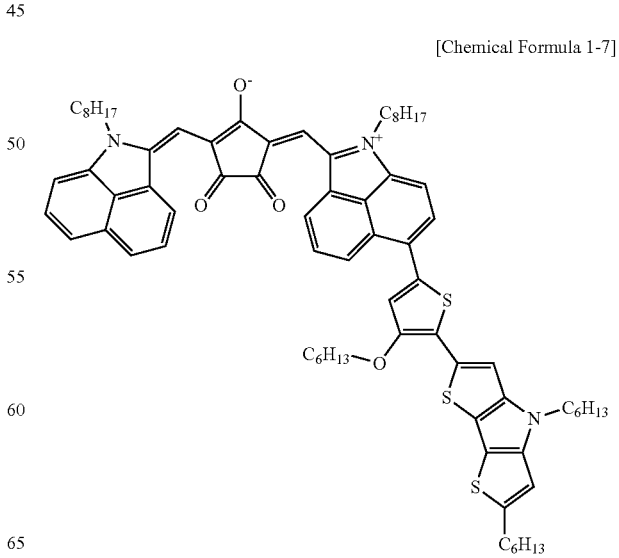

[Reaction Scheme 1-7]

(21) + (24) ⟶

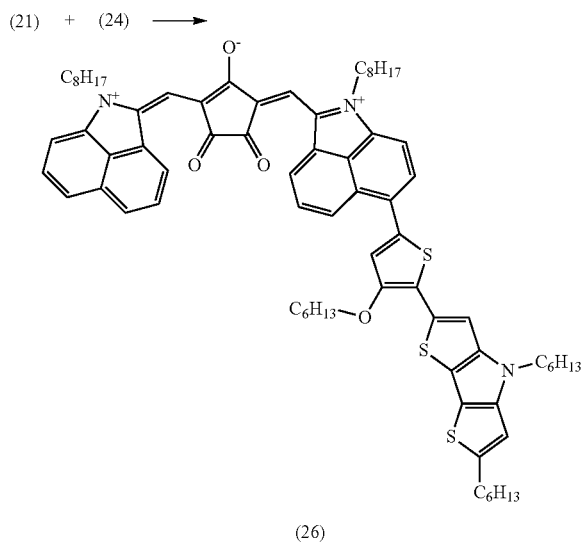

(26)

i) First Step: Synthesis of Compound represented by Chemical Formula 1-7 (Compound (26))

Compound (21) (0.070 g, 0.07 mmol) and Compound (24) (0.030 g, 0.07 mmol) are dissolved in a mixed solvent of 1-butanol (3 mL) and toluene (3 mL) and then, stirred at 110° C. for 1 hour. When a reaction is completed, after removing the solvent, the resultant is separated and purified through silica gel column chromatography (EA: n-Hex=1:2 v/v) to obtain Compound (26) (0.015 g, Yield: about 17%).

LC-MS: 1192.44 m/z confirmation of molecular weight.

Synthesis Example 8: Synthesis of Compound Represented by Chemical Formula 1-8 (Compound (27))

[Chemical Formula 1-8]

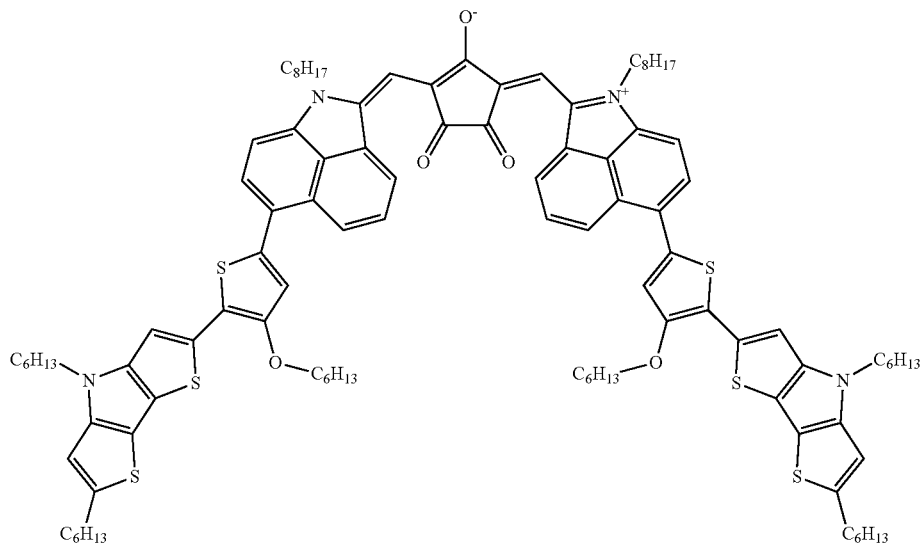

[Reaction Scheme 1-8]

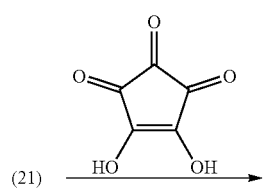

(21) ⟶

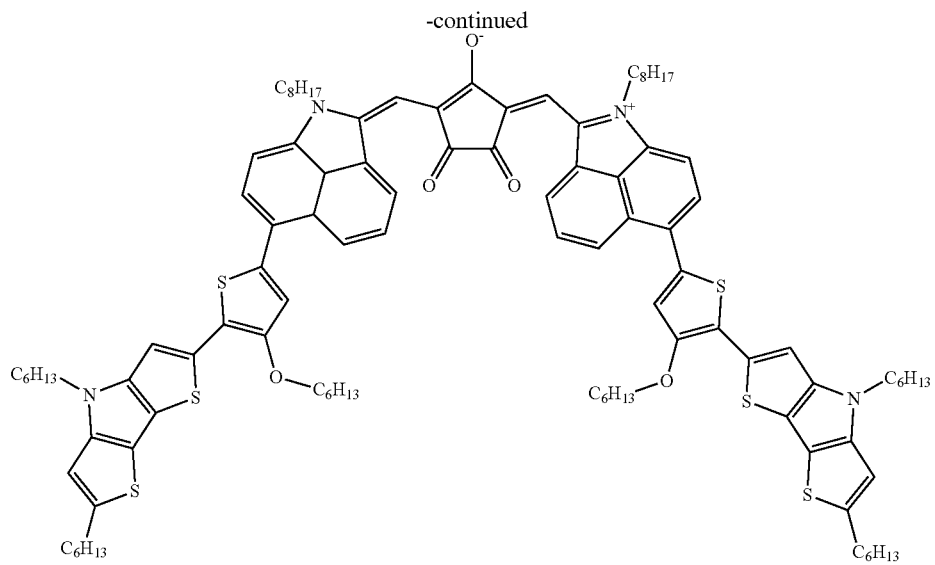

(27)

i) First Step: Synthesis of Compound represented by Chemical Formula 1-8 (Compound (27))

Compound (21) (0.080 g, 0.09 mmol) and croconic acid (0.006 g, 0.04 mmol) are dissolved in a mixed solvent of 1-butanol (3 mL) and toluene (3 mL) and then, stirred at 110° C. for 1 hour. When a reaction is completed, after removing the solvent, the resultant is separated and purified through silica gel column chromatography (EA: n-Hex=1:2 v/v) to obtain Compound (27) (0.02 g, Yield: about 27%).

LC-MS: 1721.76 m/z confirmation of molecular weight.

Comparative Synthesis Example 1: Synthesis of Compound Represented by Chemical Formula 2-1

A method of Reference ACS Appl. Mater. Interfaces 10, 11063 (2018) is used for the synthesis.

[Chemical Formula 2-1]

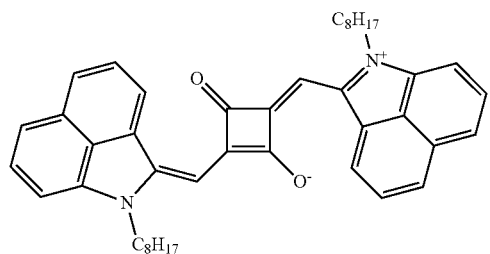

[Reaction Scheme 2-1]

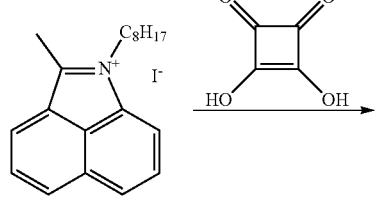

-continued

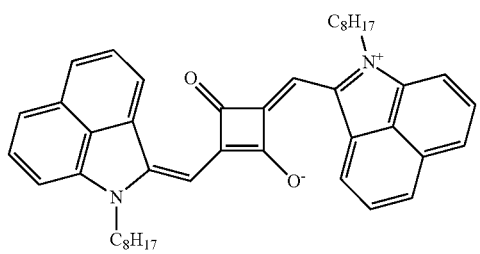

Comparative Synthesis Example 2: Synthesis of Compound Represented by Chemical Formula 2-2

[Chemical Formula 2-2]

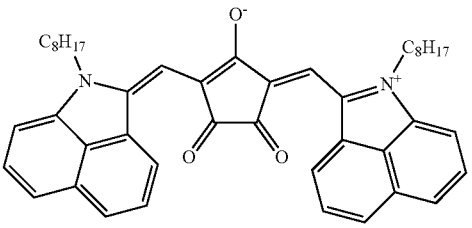

[Reaction Scheme 2-2]

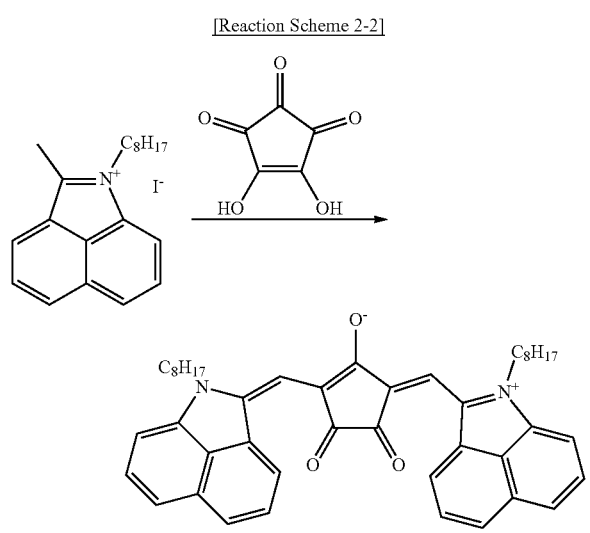

2-methyl-1-octylbenzo[cd]indole-1-ium iodide (0.4 g, 1.0 mmol) and croconic acid (0.056 g, 0.4 mmol) are dissolved in acetone (6 mL) and H$_2$O (6 mL) and then, stirred at room temperature for 72 hours. Subsequently, H$_2$O (40 mL) is added thereto, and impurities dissolved therein are all removed with a filter. Precipitates remaining there are separated and purified through silica gel column chromatography (acetone: chloroform=1:4 v/v) to obtain a compound represented by Chemical Formula 2-2 (0.13 g, Yield: about 50%).

LC-MS: 665.26 m/z confirmation of molecular weight.

Evaluation I: Light Absorption Characteristics

The compounds according to Synthesis Examples 1 to 8 and Comparative Synthesis Example 1 in dichloromethane are respectively dissolved at a concentration of 1×10$^{-5}$ M to prepare solutions, and light absorption characteristics of the compounds in a solution state are evaluated. The results are shown in Table 1.

The light absorption characteristics are evaluated by using an UV-Vis-NIR spectrometer (UV-3600 Plus, Shimadzu Corp.) to measure a maximum absorption wavelength ($\lambda_{max}$).

In some example embodiments, the compounds obtained in Synthesis Examples 1 to 8 and Comparative Synthesis Example 1 are coated on a glass substrate by spin coating, respectively, to evaluate light absorption characteristics in a thin film state. The light absorption characteristics are evaluated by measuring a maximum absorption wavelength ($\lambda_{max}$) by using a UV-Vis-NIR spectrometer (UV-3600 Plus, Shimadzu Corp.). The results are shown in Table 1.

TABLE 1

|  | $\lambda_{max}$ (nm) (solution) | $\lambda_{max}$ (nm) (thin film) |
|---|---|---|
| Synthesis Example 1 | 972 | 1060 |
| Synthesis Example 2 | 972 | 1060 |
| Synthesis Example 3 | 974 | 1060 |
| Synthesis Example 4 | 986 | 1065 |
| Synthesis Example 5 | 1013 | 1100 |
| Synthesis Example 6 | 1081 | 1200 |
| Synthesis Example 7 | 1112 | 1210 |
| Synthesis Example 8 | 1182 | 1350 |
| Comparative Synthesis Example 1 | 884 | 960 |

Referring to Table 1, the compounds according to Synthesis Example 1 to 8 exhibit superior wavelength absorption characteristics in an infrared wavelength region, than the compound according to Comparative Synthesis Example 1.

Evaluation II: Energy Level and Bandgap

HOMO energy levels, LUMO energy levels, and bandgap energies (e.g., HOMO-LUMO bandgap energies) of each thin film are evaluated in a method of Gaussian 09 program] according to a B3LYP/6-31 G(d) level theory described in [M. J. Frisch, et al., Gaussian 09, Revision D.01; Gaussian, Inc.: Wallingford, CT 2009]. The results are shown in Table 2.

TABLE 2

|  | HOMO (eV) | LUMO (eV) | Bandgap energy (eV) |
|---|---|---|---|
| Synthesis Example 1 | −4.60 | −3.20 | 1.40 |
| Synthesis Example 2 | −4.60 | −3.20 | 1.40 |
| Synthesis Example 3 | −4.41 | −3.26 | 1.15 |
| Synthesis Example 4 | −4.52 | −3.24 | 1.28 |
| Synthesis Example 5 | −4.52 | −3.29 | 1.23 |
| Synthesis Example 6 | −4.66 | −3.48 | 1.18 |
| Synthesis Example 7 | −4.61 | −3.54 | 1.07 |
| Synthesis Example 8 | −4.52 | −3.53 | 0.99 |
| Comparative Synthesis Example 1 | −4.80 | −3.26 | 1.54 |

Referring to Table 2, the compounds of Synthesis Examples 1 to 8 have smaller bandgap energies than the compound of Comparative Synthesis Example 1 and thus may more effectively absorb light in the infrared wavelength region.

Examples and Comparative Examples: Production of Photoelectric Device

ITO is stacked on a glass substrate by sputtering to form an anode. Subsequently, PEDOT (poly(3,4-ethylenedioxythiophene)) is coated on the anode by spin coating to form a 45 nm-thick hole transport layer. A 150 nm-thick photoactive layer (photoelectric conversion layer) is formed by spin coating a solution obtained by dissolving each of the compounds according to Synthesis Examples 1 to 8 and Comparative Synthesis Examples 1 and 2 in PC70BM and chloroform in a mass ratio of 2.5:7.5 on the hole transport layer. Then, C60 is deposited on the photoactive layer to form a 30 nm-thick auxiliary layer. Then, ITO is sputtered on the auxiliary layer to form a cathode. Subsequently, products obtained therefrom are sealed with a glass plate and annealed sequentially at 120° C. and 140° C. for 30 minutes to produce photoelectric devices according to Example 1 to 8 and Comparative Examples 1 and 2.

Evaluation III: Photoelectric Conversion Efficiency

Photoelectric conversion efficiency (EQE) of the photoelectric devices according to Examples 1 to 8 and Comparative Examples 1 and 2 is evaluated. The photoelectric conversion efficiency is measured by using an IPCE measurement system (TNE Technology Co., Ltd., Korea). First, the system is calibrated by using a Si photodiode (Hamamatsu Photonics K.K., Japan) and then, mounted on a photoelectric device to measure the photoelectric conversion efficiency in a wavelength range of about 400 nm to about 1600 nm. Herein, photoelectric conversion efficiency of the photoelectric devices according to Example 1, Example 6 and Comparative Example 1 is measured, and the results are shown in FIG. 13.

Figure 13:
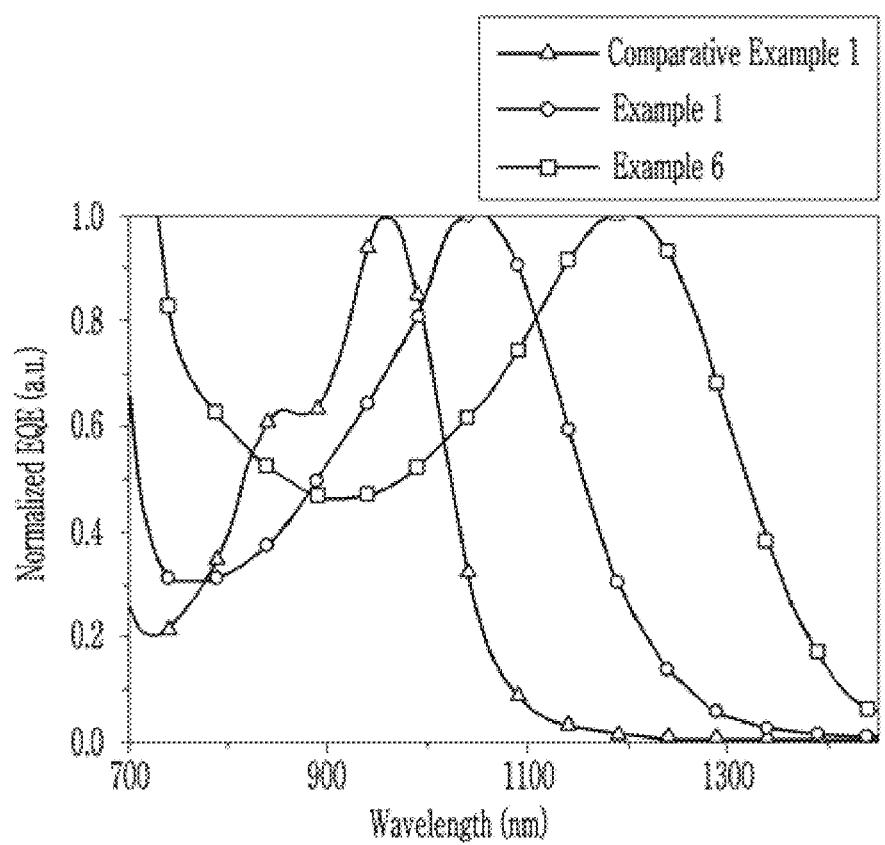
FIG. 13 is a graph showing the results of measuring the photoelectric conversion efficiency of the photoelectric devices according to Example 1, Example 6, and Comparative Example 1.

FIG. 13 is a graph showing the results of measuring the photoelectric conversion efficiency of the photoelectric devices according to Example 1, Example 6, and Comparative Example 1.

Referring to FIG. 13, the photoelectric devices according to Examples 1 and 6 exhibit superior photoelectric conversion efficiency in a long wavelength region of greater than about 1000 nm compared with the photoelectric device according to Comparative Example 1. For example, as shown in FIG. 13, the photoelectric devices according to Examples 1 and 6 may exhibit a peak EQE (e.g., EQE of about 1.0) in a longer wavelength region between about 1050 nm and about 1250 nm while the photoelectric device according to Comparative Example 1 may exhibit a peak EQE (e.g., EQE of about 1.0) in a shorter wavelength region of about 950 nm.

While this disclosure has been described in connection with what is presently considered to be practical example embodiments, it is to be understood that the inventive concepts are not limited to these example embodiments. On the contrary, it is intended to cover various modifications and equivalent arrangements included within the spirit and scope of the appended claims.

<Description of Symbols>

| | |
|---|---|
| 10: first electrode | 20: second electrode |
| 30: photoactive layer | 50a, 50b, 50c: photo-sensing device |
| 55: charge storage | 70a, 70b, 70c: color filter |
| 80: insulation layer | 100, 100': photoelectric device |
| 10B, 10G, 10R, 10IR: first electrode | |
| 20B, 20G, 20R, 20IR: second electrode | |
| 30B, 30G, 30R, 30IR: photoactive layer | |
| 50B: blue light charge storage | 50G: green light charge storage |
| 50R: red light charge storage | 50IR: infrared light charge storage |
| 110: semiconductor substrate | 65: lower insulation layer |
| 70a, 70b, 70c: color filters | 80: upper insulation layer |
| 100B: blue photo-sensing device | 100G: green photo-sensing device |
| 100R: red photo-sensing device | |
| 100IR: infrared photo-sensing device | |
| 300, 400, 500, 600, 700: image sensor | |

What is claimed is:

1. A compound represented by Chemical Formula 1:

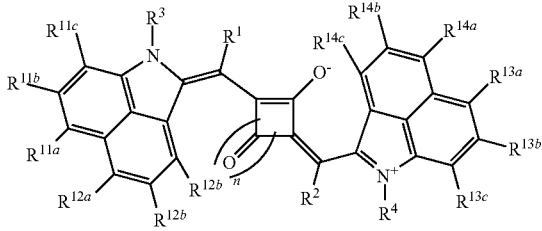

[Chemical Formula 1]

wherein, in Chemical Formula 1,

R$^1$ to R$^4$ are each independently hydrogen, deuterium, a C1 to C10 alkyl group, a C1 to C10 alkoxy group, a C1 to C10 haloalkyl group, a C6 to C14 aryl group, or a C3 to C12 heteroaryl group, R$^{11a}$ to R$^{14c}$ are each independently hydrogen, deuterium, a halogen, a cyano group, a C1 to C10 alkyl group, a C1 to C10 alkoxy group, a C1 to C10 haloalkyl group, a C6 to C14 aryl group, a C6 to C14 aryloxy group, a C3 to C12 heteroaryl group, or a functional group represented by Chemical Formula 1A, wherein at least one of R$^{11a}$ to R$^{14c}$ is a functional group represented by Chemical Formula 1A, wherein R$^{11a}$ to R$^{14c}$ are present independently of each other or an adjacent two of R$^{11a}$ to R$^{14c}$ are linked to each other to form a fused ring with benzoindole, and n is an integer of 1 or 2,

*-L$_1$-(L$_2$)$_m$-Ar  [Chemical Formula 1A]

wherein, in Chemical Formula 1A,

L$_1$ is a substituted or unsubstituted C2 to C15 heteroaromatic ring group,

L$_2$ is a substituted or unsubstituted C2 to C15 heteroaromatic ring group, a substituted or unsubstituted C6 to C30 aromatic ring group, a substituted or unsubstituted C1 to C10 alkylene group, or a substituted or unsubstituted C3 to C20 cycloalkylene group, Ar is a substituted or unsubstituted C6 to C30 aromatic ring group, a substituted or unsubstituted C2 to C30 heteroaromatic ring group, a fused ring thereof, a substituted or unsubstituted C6 to C30 arylamine group, or a substituted or unsubstituted C2 to C30 heteroarylamine group, and m is 0, 1, or 2.

2. The compound of claim 1, wherein in Chemical Formula 1A, L$_1$ and L$_2$ are each independently a heteroaromatic ring group represented by one of Chemical Formulas 1A-11 to 1A-15, or a combination thereof:

[Chemical Formulas 1A-11 to 1A-15]

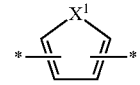 (1A-11)

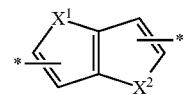 (1A-12)

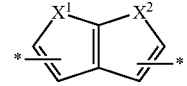 (1A-13)

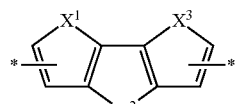 (1A-14)

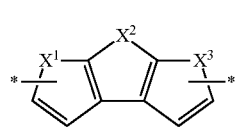 (1A-15)

wherein, in Chemical Formulas 1A-11 to 1A-15,

X$^1$, X$^2$, and X$^3$ are each independently O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ are each independently hydrogen, deuterium, a C1 to C10 alkyl group, a C1 to C10 haloalkyl group, a C6 to C14 aryl group, a C3 to C12 heteroaryl group, a halogen, a cyano group, or a combination thereof, and hydrogen of each heteroaromatic ring is optionally replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group.

3. The compound of claim 1, wherein, in Chemical Formula 1A, L$_1$ and L$_2$ are each independently a heteroaromatic ring group represented by one of Chemical Formulas 1A-16 to 1A-20, or a combination thereof:

[Chemical Formulas 1A-16 to 1A-20]

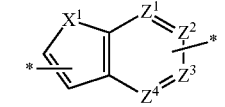 (1A-16)

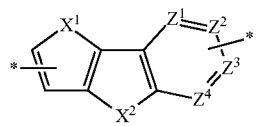 (1A-17)

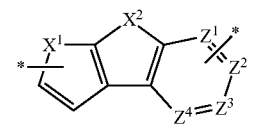 (1A-18)

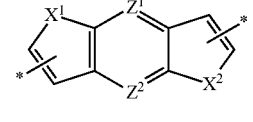 (1A-19)

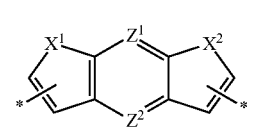 (1A-20)

wherein, in Chemical Formulas 1A-16 to 1A-20,

X$^1$ and X$^2$ are each independently O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ are each independently hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, Z$^1$ to Z$^4$ are each independently CR$^x$ or N, wherein R$^x$ is hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, or a single bond, wherein in Chemical Formulas 1A-16 to 1A-18, one of Z$^1$ to Z$^4$ is CR$^x$ wherein R$^x$ is a single bond, and hydrogen of each aromatic ring and heteroaromatic ring is optionally replaced by deuterium, a halogen, a cyano group, a C1 to C10 alkyl group, a C1 to C10 alkoxy group, a C1 to C10 haloalkyl group, a —SiH$_3$ group, or a C1 to C10 alkylsilyl group.

4. The compound of claim 1, wherein L$_1$ and L$_2$ are each independently a combination of a heteroaromatic ring group represented by one of Chemical Formulas 1A-11 to 1A-15 and a heteroaromatic ring group represented by one of Chemical Formulas 1A-16 to 1A-20:

[Chemical Formulas 1A-11 to 1A-15]

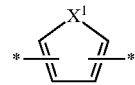 (1A-11)

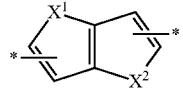 (1A-12)

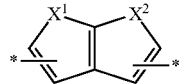 (1A-13)

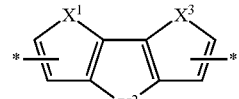 (1A-14)

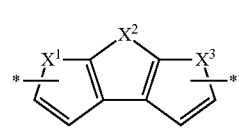 (1A-15)

wherein, in Chemical Formulas 1A-11 to 1A-15,

X$^1$, X$^2$, and X$^3$ are each independently O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ are each independently hydrogen, deuterium, a C1 to C10 alkyl group, a C1 to C10 haloalkyl group, a C6 to C14 aryl group, a C3 to C12 heteroaryl group, a halogen, a cyano group, or a combination thereof, and hydrogen of each heteroaromatic ring is optionally replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group,

[Chemical Formulas 1A-16 to 1A-20]

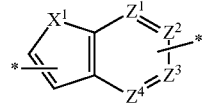 (1A-16)

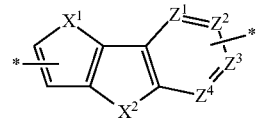 (1A-17)

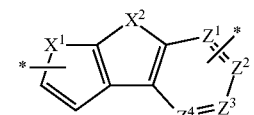 (1A-18)

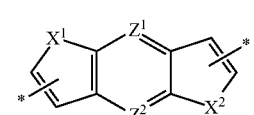 (1A-19)

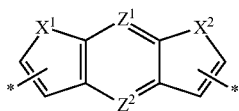

(1A-20)

wherein, in Chemical Formulas 1A-16 to 1A-20,
$X^1$ and $X^2$ are each independently O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ are each independently hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, $Z^1$ to $Z^4$ are each independently CR$^x$ or N, wherein R$^x$ is hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, or a single bond, wherein in Chemical Formulas 1A-16 to 1A-18, one of $Z^1$ to $Z^4$ is CR$^x$ wherein R$^x$ is a single bond, and hydrogen of each aromatic ring and heteroaromatic ring is optionally replaced by deuterium, a halogen, a cyano group, a C1 to C10 alkyl group, a C1 to C10 alkoxy group, a C1 to C10 haloalkyl group, a —SiH$_3$ group, or a C1 to C10 alkylsilyl group.

5. The compound of claim 1, wherein, in Chemical Formula 1A, Ar is an aromatic ring group represented by one of Chemical Formulas 1B-11 to 1B-15:

[Chemical Formulas 1B-11 to 1B-15]

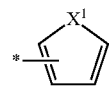

(1B-11)

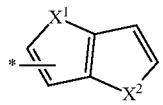

(1B-12)

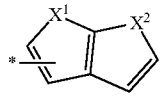

(1B-13)

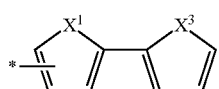

(1B-14)

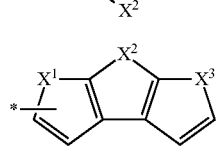

(1B-15)

wherein, in Chemical Formulas 1B-11 to 1B-15,
$X^1$, $X^2$, and $X^3$ are each independently O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ are each independently hydrogen, deuterium, a C1 to C10 alkyl group, a C1 to C10 haloalkyl group, a C6 to C14 aryl group, a C3 to C12 heteroaryl group, a halogen, a cyano group, or a combination thereof, and hydrogen of each heteroaromatic ring is optionally replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group.

6. The compound of claim 1, wherein, in Chemical Formula 1A, Ar is a substituted or unsubstituted C6 to C30 aryl group, a substituted or unsubstituted C2 to C15 heteroaryl group, or a fused ring thereof.

7. The compound of claim 1, wherein, in Chemical Formula 1A, Ar is a substituted or unsubstituted phenyl group, a substituted or unsubstituted naphthyl group, a substituted or unsubstituted acenaphthenyl group, a substituted or unsubstituted anthracenyl group, a substituted or unsubstituted phenanthrenyl group, a substituted or unsubstituted tetracenyl group, a substituted or unsubstituted pyrenyl group, a substituted or unsubstituted quinolyl group, a substituted or unsubstituted isoquinolyl group, a substituted or unsubstituted quinoxalyl group, a substituted or unsubstituted quinazolyl group, or a substituted or unsubstituted phenanthrolyl group.

8. The compound of claim 1, wherein, in Chemical Formula 1A, Ar is a C6 to C30 aryl group substituted with an arylamine group, a C2 to C15 heteroaryl group substituted with an arylamine group, or a fused ring thereof, and the arylamine group is represented by Chemical Formula 1C-1:

[Chemical Formula 1C-1]

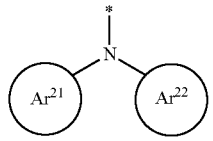

wherein, in Chemical Formula 1C-1,
Ar$^{21}$ and Ar$^{22}$ are each independently a substituted or unsubstituted C6 to C30 aryl group or a substituted or unsubstituted C3 to C30 heteroaryl group.

9. The compound of claim 8, wherein Chemical Formula 1C-1 is represented by Chemical Formula 1C-1a or Chemical Formula 1C-1 b:

[Chemical Formula 1C-1a]

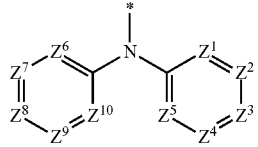

wherein, in Chemical Formula 1C-1a,
$Z^1$ to $Z^{10}$ are each independently N or CR$^x$, wherein R$^x$ is hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when $Z^1$ to $Z^{10}$ are $CR^x$, $R^x$ of each of $Z^1$ to $Z^{10}$ is independently present or at least an adjacent two of $Z^1$ to $Z^{10}$ are linked to each other to form a 5-membered aromatic ring or a 6-membered aromatic ring,

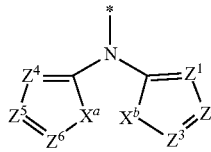

[Chemical Formula 1C-1b]

wherein, in Chemical Formula 1C-1b,
$X^a$ and $X^b$ are each independently —O—, —S—, —Se—, —Te—, —$NR^a$—, —$SiR^bR^c$—, or —$GeR^dR^e$—, wherein $R^a$, $R^b$, $R^c$, $R^d$, and $R^e$ are each independently hydrogen, a halogen, a substituted or unsubstituted C1 to C10 alkyl group, or a substituted or unsubstituted C6 to C10 aryl group,
$Z^1$ to $Z^6$ are each independently N or $CR^x$, wherein $R^x$ is hydrogen, deuterium, a C1 to C10 alkyl group, a C1 to C10 haloalkyl group, a C1 to C10 alkoxy group, a —$SiH_3$ group, a C1 to C10 alkylsilyl group, a —$NH_2$ group, a C1 to C10 alkylamine group, a C6 to C12 aryl group, a C3 to C12 heteroaryl group, a halogen, a cyano group, or a combination thereof, and
when $Z^1$ to $Z^6$ are $CR^x$, $R^x$ is independently present in each of $Z^1$ to $Z^6$ or at least an adjacent two of $Z^1$ to $Z^6$ are linked to each other to form a 5-membered aromatic ring or a 6-membered aromatic ring.

10. The compound of claim 1, wherein, in Chemical Formula 1A, Ar is a C6 to C30 aryl group substituted with an N-containing heterocyclic group, a C2 to C15 heteroaryl group substituted with an N-containing heterocyclic group, or a fused ring thereof, and the N-containing heterocyclic group is represented by Chemical Formula 1C-2:

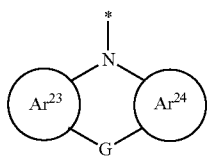

[Chemical Formula 1C-2]

wherein, in Chemical Formula 1C-2,
$Ar^{23}$ and $Ar^{24}$ are each independently a substituted or unsubstituted C6 to C30 aryene group or a substituted or unsubstituted C3 to C15 heteroarene group, and
G is a single bond, —O—, —S—, —Se—, —Te—, —N—, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ are each independently hydrogen, a halogen, a substituted or unsubstituted C1 to C10 alkyl group, or a substituted or unsubstituted C6 to C10 aryl group, wherein $R^b$, $R^c$, $R^d$, $R^e$, $R^f$, $R^g$, $R^h$, and $R^i$ are each independently present or $R^b$ and $R^c$, $R^d$ and $R^e$, $R^f$ and $R^g$, or $R^h$ and $R^i$ are linked to each other to provide a ring, and n of —$(CR^fR^g)_n$— is 1 or 2.

11. The compound of claim 10, wherein Chemical Formula 1C-2 is represented by Chemical Formula 1C-2a, 1C-2b, or 1C-2c:

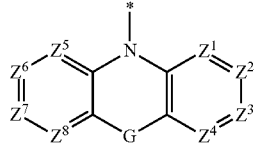

[Chemical Formula 1C-2a]

wherein, in Chemical Formula 1C-2a,
G is a single bond, —O—, —S—, —Se—, —Te—, —N—, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ are each independently hydrogen, a halogen, a substituted or unsubstituted C1 to C10 alkyl group, or a substituted or unsubstituted C6 to C10 aryl group, wherein $R^b$, $R^c$, $R^d$, $R^e$, $R^f$, $R^g$, $R^h$, or $R^i$ are each independently present or $R^b$ and $R^c$, $R^d$ and $R^e$, $R^f$ and $R^g$, or $R^h$ and $R^i$ are linked to each other to provide a ring, and n of —$(CR^fR^g)_n$— is 1 or 2,
$Z^1$ to $Z^8$ are each independently N or $CR^x$, wherein $R^x$ is hydrogen, deuterium, a C1 to C10 alkyl group, a C1 to C10 haloalkyl group, a C1 to C10 alkoxy group, a —$SiH_3$ group, a C1 to C10 alkylsilyl group, a —$NH_2$ group, a C1 to C10 alkylamine group, a C6 to C12 aryl group, a C3 to C12 heteroaryl group, a halogen, a cyano group, or a combination thereof, and
when $Z^1$ to $Z^8$ are $CR^x$, $R^x$ of each of $Z^1$ to $Z^8$ is independently present or at least adjacent two of $Z^1$ to $Z^8$ are linked to each other to form a 5-membered aromatic ring or a 6-membered aromatic ring,

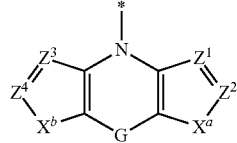

[Chemical Formula 1C-2b]

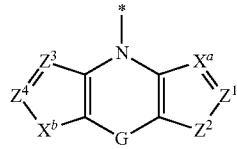

[Chemical Formula 1C-2c]

wherein, in Chemical Formulas 1C-2b and 1C-2c, G is a single bond, —O—, —S—, —Se—, —Te—, —N—, —$NR^a$—, —$SiR^bR^c$—, —$GeR^dR^e$—, —$(CR^fR^g)_n$—, or —$(C(R^h)=C(R^i))$—, wherein $R^a$, $R^b$, $R^c$, $R^d$, $R^e$, $R^f$, $R^g$, $R^h$, and $R^i$ are each independently hydrogen, a halogen, a substituted or unsubstituted C1 to C10 alkyl group, or a substituted or unsubstituted C6 to C10 aryl group, wherein $R^b$, $R^c$, $R^d$, $R^e$, $R^f$, $R^g$, $R^h$, or $R^i$ are each independently present or $R^b$ and $R^c$, $R^d$ and $R^e$, $R^f$ and $R^g$, or $R^h$ and $R^i$ are linked to each other to provide a ring, and n of —$(CR^fR^g)_n$— is 1 or 2, $X^a$ and $X^b$ are each independently —O—, —S—, —Se—, —Te—, —NR$^p$—, —SiR$^p$R$^r$—, or —GeR$^s$R$^t$—, wherein R$^p$, R$^q$, R$^r$, R$^s$, and R$^t$ are each independently hydrogen, a halogen, a substituted or unsubstituted C1 to C10 alkyl group, or a substituted or unsubstituted C6 to C10 aryl group, $Z^1$ to $Z^4$ are each independently N or CR$^x$, wherein R$^x$ is hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when $Z^1$ to $Z^4$ are CR$^x$, R$^x$ of each of $Z^1$ to $Z^4$ is independently present or at least an adjacent two of $Z^1$ to $Z^4$ are linked to each other to form a 5-membered aromatic ring or a 6-membered aromatic ring.

12. The compound of claim 1, wherein, in Chemical Formula 1A, Ar is an aromatic ring or heteroaromatic ring group represented by one of Chemical Formulas 1B-16 to 1B-25:

[Chemical Formulas 1B-16 to 1B-25]

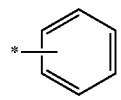
(1B-16)

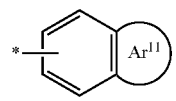
(1B-17)

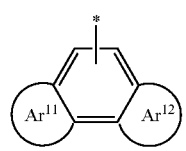
(1B-18)

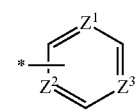
(1B-19)

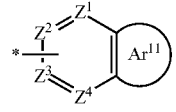
(1B-20)

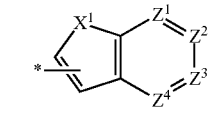
(1B-21)

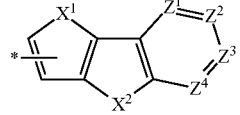
(1B-22)

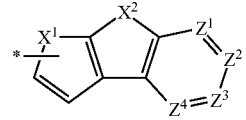
(1B-23)

-continued

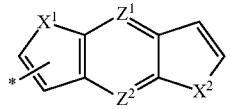
(1B-24)

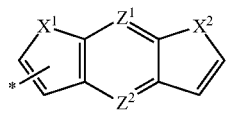
(1B-25)

wherein, in Chemical Formulas 1B-16 to 1B-25, $X^1$ and $X^2$ are each independently O, S, Se, Te, S(=O), S(=O)$_2$, NR$^a$, SiR$^b$R$^c$, or GeR$^d$R$^e$, wherein R$^a$, R$^b$, R$^c$, R$^d$, and R$^e$ are each independently hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, $Z^1$ to $Z^4$ are each independently CR$^x$ or N, wherein R$^x$ is hydrogen, deuterium, a C1 to C10 alkyl group, a C1 to C10 haloalkyl group, a —SiH$_3$ group, a C1 to C10 alkylsilyl group, a —NH$_2$ group, a C1 to C10 alkylamine group, a C6 to C10 arylamine group, a C6 to C14 aryl group, a C3 to C12 heteroaryl group, a halogen, a cyano group, or a combination thereof, or a single bond, wherein in Chemical Formula 1B-20, one of $Z^1$ to $Z^4$ is CR$^x$ wherein R$^x$ is a single bond, Ar$^{11}$ and Ar$^{12}$ are each independently a substituted or unsubstituted C6 to C30 arene group or a substituted or unsubstituted C3 to C30 heteroarene group, and hydrogen of each aromatic ring and heteroaromatic ring is optionally replaced by deuterium, a halogen, a cyano group, a C1 to C10 alkyl group, a C1 to C10 alkoxy group, a C1 to C10 haloalkyl group, a C6 to C10 aryl group, a C6 to C10 aryloxy group, a —SiH$_3$ group, or a C1 to C10 alkylsilyl group.

13. The compound of claim 12, wherein the aromatic ring or heteroaromatic ring group represented by one of Chemical Formulas 1B-16 to 1B-25 is substituted with an arylamine group, and the arylamine group is represented by Chemical Formula 1C-1:

[Chemical Formula 1C-1]

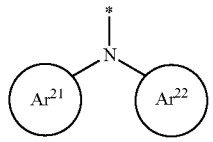

wherein, in Chemical Formula 1C-1,

Ar$^{21}$ and Ar$^{22}$ are each independently a substituted or unsubstituted C6 to C30 aryl group or a substituted or unsubstituted C3 to C30 heteroaryl group.

14. The compound of claim 13, wherein Chemical Formula 1C-1 is represented by Chemical Formula 1C-1a or 1C-1 b:

[Chemical Formula 1C-1a]

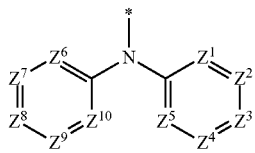

wherein, in Chemical Formula 1C-1a,
$Z^1$ to $Z^{10}$ are each independently N or $CR^x$, wherein $R^x$ is hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and
when $Z^1$ to $Z^{10}$ are $CR^x$, $R^x$ of each of $Z^1$ to $Z^{10}$ is independently present or at least an adjacent two of $Z^1$ to $Z^{10}$ are linked to each other to form a 5-membered aromatic ring or a 6-membered aromatic ring,

[Chemical Formula 1C-1b]

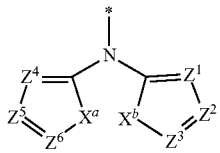

wherein, in Chemical Formula 1C-1b,
$X^a$ and $X^b$ are each independently —O—, —S—, —Se—, —Te—, —NR$^a$—, —SiR$^b$R$^c$—, or —GeR$^d$R$^e$—, wherein R$^a$, R$^b$, R$^c$, R$^d$, and R$^e$ are each independently hydrogen, a halogen, a substituted or unsubstituted C1 to C10 alkyl group, or a substituted or unsubstituted C6 to C10 aryl group,
$Z^1$ to $Z^6$ are each independently N or $CR^x$, wherein $R^x$ is hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and
when $Z^1$ to $Z^6$ are $CR^x$, $R^x$ is independently present in each of $Z^1$ to $Z^6$ or at least an adjacent two of $Z^1$ to $Z^6$ are linked to each other to form a 5-membered aromatic ring or a 6-membered aromatic ring.

15. The compound of claim 12, wherein
the aromatic ring or heteroaromatic ring group represented by one of Chemical Formulas 1B-16 to 1B-25 is substituted with an N-containing heterocyclic group, and
the N-containing heterocyclic group is represented by Chemical Formula 1C-2:

[Chemical Formula 1C-2]

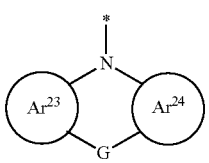

wherein, in Chemical Formula 1C-2,
Ar$^{23}$ and Ar$^{24}$ are each independently a substituted or unsubstituted C6 to C30 arene group or a substituted or unsubstituted C3 to C15 heteroarene group, and
G is a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are each independently hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ are each independently present or R$^b$ and R$^c$, R$^d$ and R$^e$, R$^f$ and R$^g$, or R$^h$ and R$^i$ are linked to each other to provide a ring, and n of —(CR$^f$R$^g$)$_n$— is 1 or 2.

16. The compound of claim 15, wherein Chemical Formula 1C-2 is represented by Chemical Formula 1C-2a, 1C-2b, or 1C-2c:

[Chemical Formula 1C-2a]

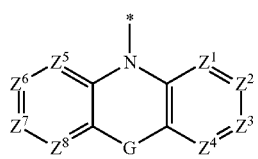

wherein, in Chemical Formula 1C-2a,
G is a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are each independently hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ are each independently present or R$^b$ and R$^c$, R$^d$ and R$^e$, R$^f$ and R$^g$, or R$^h$ and R$^i$ are linked to each other to provide a ring, and n of —(CR$^f$R$^g$)$_n$— is 1 or 2,
$Z^1$ to $Z^8$ are each independently N or $CR^x$, wherein $R^x$ is hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and
when $Z^1$ to $Z^8$ are $CR^x$, $R^x$ of each of $Z^1$ to $Z^8$ is independently present or at least adjacent two of $Z^1$ to $Z^8$ are linked to each other to form a 5-membered aromatic ring or a 6-membered aromatic ring,

[Chemical Formula 1C-2b]

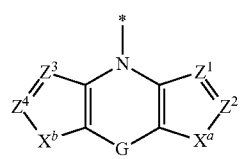

[Chemical Formula 1C-2c]

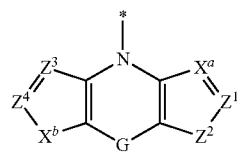

wherein, in Chemical Formulas 1C-2b and 1C-2c,
G is a single bond, —O—, —S—, —Se—, —Te—, —N—, —NR$^a$—, —SiR$^b$R$^c$—, —GeR$^d$R$^e$—, —(CR$^f$R$^g$)$_n$—, or —(C(R$^h$)=C(R$^i$))—, wherein R$^a$, R$^b$, R$^c$, R$^d$, R$^e$, R$^f$, R$^g$, R$^h$, and R$^i$ are each independently hydrogen, a halogen, a substituted or unsubstituted C1 to C10 alkyl group, or a substituted or unsubstituted C6 to C10 aryl group, wherein R$^b$, R$^c$, R$^d$, R$^e$, R$^f$, R$^g$, R$^h$, and R$^i$ are each independently present or R$^b$ and R$^c$, R$^d$ and R$^e$, R$^f$ and R$^g$, or R$^h$ and R$^i$ are linked to each other to provide a ring, and n of —(CR$^f$R$^g$)$_n$— is 1 or 2, X$^a$ and X$^b$ are each independently —O—, —S—, —Se—, —Te—, —NR$^p$—, —SiR$^p$R$^r$— or —GeR$^s$R$^t$—, wherein R$^p$, R$^q$, R$^r$, R$^s$, and R$^t$ are each independently hydrogen, a halogen, a substituted or unsubstituted C1 to C10 alkyl group, or a substituted or unsubstituted C6 to C10 aryl group, Z$^1$ to Z$^4$ are each independently N or CR$^x$, wherein R$^x$ is hydrogen, deuterium, a C1 to C10 alkyl group, a C1 to C10 haloalkyl group, a C1 to C10 alkoxy group, a —SiH$_3$ group, a C1 to C10 alkylsilyl group, a —NH$_2$ group, a C1 to C10 alkylamine group, a C6 to C12 aryl group, a C3 to C12 heteroaryl group, a halogen, a cyano group, or a combination thereof, and when Z$^1$ to Z$^4$ are CR$^x$, R$^x$ of each of Z$^1$ to Z$^4$ is independently present or at least an adjacent two of Z$^1$ to Z$^4$ are linked to each other to form a 5-membered aromatic ring or a 6-membered aromatic ring.

17. The compound of claim 1, wherein
in Chemical Formula 1,
at least one of R$^{11a}$, R$^{11b}$, R$^{11c}$, R$^{12a}$, R$^{12b}$, or R$^{12c}$ is the functional group represented by Chemical Formula 1A, and
at least one of R$^{13a}$, R$^{13b}$, R$^{13c}$, R$^{14a}$, R$^{14b}$, or R$^{14c}$ is the functional group represented by Chemical Formula 1A.

18. The compound of claim 1, wherein
in Chemical Formula 1,
at least one of R$^{11a}$, R$^{11b}$, or R$^{11c}$ is the functional group represented by Chemical Formula 1A, and
at least one of R$^{13a}$, R$^{13b}$, or R$^{13c}$ is the functional group represented by Chemical Formula 1A.

19. The compound of claim 1, wherein
in Chemical Formula 1,
at least one of R$^{12a}$, R$^{12b}$, or R$^{12c}$ is the functional group represented by Chemical Formula 1A, and
at least one of R$^{14a}$, R$^{14b}$, or R$^{14c}$ is the functional group represented by Chemical Formula 1A.

20. The compound of claim 1, wherein R$^{11a}$ and R$^{13a}$ are the functional group represented by Chemical Formula 1A.

21. The compound of claim 1, wherein R$^{12a}$ and R$^{14a}$ are the functional group represented by Chemical Formula 1A.

22. An infrared absorber comprising the compound of claim 1.

23. An infrared absorbing/blocking film comprising the compound of claim 1.

24. A photoelectric device, comprising:
a first electrode and a second electrode facing each other; and
a photoactive layer between the first electrode and the second electrode,
wherein the photoactive layer includes the compound of claim 1.

25. The photoelectric device of claim 24, wherein the photoactive layer further comprises fullerene or a fullerene derivative.

26. The photoelectric device of claim 24, wherein the photoactive layer has a peak absorption wavelength in a wavelength region of about 750 nm to about 3000 nm.

27. A sensor comprising the photoelectric device of claim 24.

28. An electronic device comprising the sensor of claim 27.

29. An electronic device comprising the photoelectric device of claim 24.

30. A photoelectric device, comprising:
a first electrode and a second electrode facing each other;
a photoactive layer between the first electrode and the second electrode; and
a charge auxiliary layer between
the photoactive layer and the first electrode, or
the photoactive layer and the second electrode,
wherein at least one of the first electrode, the second electrode, the photoactive layer, or the charge auxiliary layer includes a compound represented by Chemical Formula 1:

[Chemical Formula 1]

wherein, in Chemical Formula 1,
R$^1$ to R$^4$ are each independently hydrogen, deuterium, a C1 to C10 alkyl group, a C1 to C10 alkoxy group, a C1 to C10 haloalkyl group, a C6 to C14 aryl group, or a C3 to C12 heteroaryl group,
R$^{11a}$ to R$^{14c}$ are each independently hydrogen, deuterium, a halogen, a cyano group, a C1 to C10 alkyl group, a C1 to C10 alkoxy group, a C1 to C10 haloalkyl group, a C6 to C14 aryl group, a C6 to C14 aryloxy group, a C3 to C12 heteroaryl group, or a functional group represented by Chemical Formula 1A, wherein at least one of R$^{11a}$ to R$^{14c}$ is a functional group represented by Chemical Formula 1A, wherein R$^{11a}$ to R$^{14c}$ are present independently of each other or an adjacent two of R$^{11a}$ to R$^{14c}$ are linked to each other to form a fused ring with benzoindole, and
n is an integer of 1 or 2,

*-L$_1$-(L$_2$)$_m$-Ar  [Chemical Formula 1A]

wherein, in Chemical Formula 1A,
L$_1$ is a substituted or unsubstituted C2 to C15 heteroaromatic ring group,
L$_2$ is a substituted or unsubstituted C2 to C15 heteroaromatic ring group, a substituted or unsubstituted C6 to C30 aromatic ring group, a substituted or unsubstituted C1 to C10 alkylene group, or a substituted or unsubstituted C3 to C20 cycloalkylene group,
Ar is a substituted or unsubstituted C6 to C30 aromatic ring group, a substituted or unsubstituted C2 to C30 heteroaromatic ring group, a substituted or unsubstituted C6 to C30 arylamine group, or a substituted or unsubstituted C2 to C30 heteroarylamine group, and m is 0, 1, or 2.

31. The photoelectric device of claim 30, wherein the charge auxiliary layer includes the compound and the photoactive layer, the first electrode, and the second electrode do not include the compound.

32. The photoelectric device of claim 30, wherein the photoactive layer includes the compound and the charge auxiliary layer, the first electrode, and the second electrode do not include the compound.

33. The photoelectric device of claim 30, further comprising:
a plurality of charge auxiliary layers, the plurality of charge auxiliary layers including the charge auxiliary layer, the plurality of charge auxiliary layers including
a first charge auxiliary layer between the photoactive layer and the first electrode, and
a second charge auxiliary layer between the photoactive layer and the second electrode,
wherein at least one of the first electrode, the second electrode, the photoactive layer, the first charge auxiliary layer, or the second charge auxiliary layer includes the compound.

34. A sensor comprising the photoelectric device of claim 31.

35. An electronic device comprising the sensor of claim 32.

36. An image sensor, comprising:
a semiconductor substrate;
a first photoelectric device on the semiconductor substrate, the first photoelectric device configured to selectively absorb light in a first infrared wavelength region; and
an additional sensor configured to selectively absorb light in a separate wavelength region that is different from the first infrared wavelength region,
wherein the first photoelectric device includes a compound represented by Chemical Formula 1:

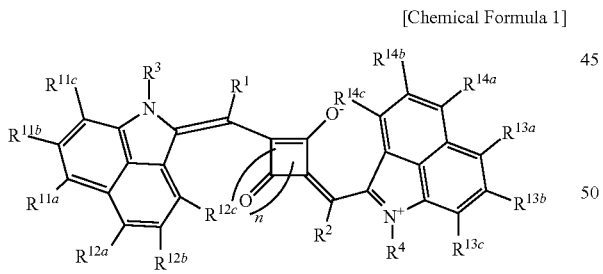

[Chemical Formula 1]

wherein, in Chemical Formula 1,
$R^1$ to $R^4$ are each independently hydrogen, deuterium, a C1 to C10 alkyl group, a C1 to C10 alkoxy group, a C1 to C10 haloalkyl group, a C6 to C14 aryl group, or a C3 to C12 heteroaryl group,
$R^{11a}$ to $R^{14c}$ are each independently hydrogen, deuterium, a halogen, a cyano group, a C1 to C10 alkyl group, a C1 to C10 alkoxy group, a C1 to C10 haloalkyl group, a C6 to C14 aryl group, a C6 to C14 aryloxy group, a C3 to C12 heteroaryl group, or a functional group represented by Chemical Formula 1A, wherein at least one of $R^{11a}$ to $R^{14c}$ is a functional group represented by Chemical Formula 1A, wherein $R^{11a}$ to $R^{14c}$ are present independently of each other or an adjacent two of $R^{11a}$ to $R^{14c}$ are linked to each other to form a fused ring with benzoindole, and
n is an integer of 1 or 2,

*-L$_1$-(L$_2$)$_m$-Ar  [Chemical Formula 1A]

wherein, in Chemical Formula 1A,
L$_1$ is a substituted or unsubstituted C2 to C15 heteroaromatic ring group,
L$_2$ is a substituted or unsubstituted C2 to C15 heteroaromatic ring group, a substituted or unsubstituted C6 to C30 aromatic ring group, a substituted or unsubstituted C1 to C10 alkylene group, or a substituted or unsubstituted C3 to C20 cycloalkylene group,
Ar is a substituted or unsubstituted C6 to C30 aromatic ring group, a substituted or unsubstituted C2 to C30 heteroaromatic ring group, a substituted or unsubstituted C6 to C30 arylamine group, or a substituted or unsubstituted C2 to C30 heteroarylamine group, and
m is 0, 1, or 2.

37. The image sensor of claim 36, wherein
the additional sensor is an infrared light sensor at least partially embedded within the semiconductor substrate, and the separate wavelength region is a separate infrared wavelength region that is different from the first infrared wavelength region, and
the first photoelectric device and the infrared light sensor overlap in a vertical direction that is perpendicular to an upper surface of the semiconductor substrate.

38. The image sensor of claim 37, wherein
the additional sensor includes a plurality of photodiodes at least partially embedded within the semiconductor substrate, the plurality of photodiodes configured to selectively absorb light in separate visible wavelength regions, and
the first photoelectric device and the plurality of photodiodes overlap in the vertical direction that is perpendicular to the upper surface of the semiconductor substrate.

39. The image sensor of claim 36, wherein
the additional sensor includes at least one additional photoelectric device vertically stacked between the first photoelectric device and the semiconductor substrate, each separate photoelectric device of the at least one additional photoelectric device including a separate photoelectric conversion layer and configured to selectively absorb light in a separate, respective wavelength region that is different from the first infrared wavelength region.

40. The image sensor of claim 36, wherein the first photoelectric device includes
a first electrode and a second electrode facing each other; and
a photoactive layer between the first electrode and the second electrode, wherein the photoactive layer includes the compound.

41. The image sensor of claim 36, wherein the first photoelectric device includes
a first electrode and a second electrode facing each other;
a photoactive layer between the first electrode and the second electrode; and
a charge auxiliary layer between
the photoactive layer and the first electrode, or
the photoactive layer and the second electrode, wherein at least one of the first electrode, the second electrode, the photoactive layer, or the charge auxiliary layer includes the compound.

42. An electronic device comprising the image sensor of claim 36.

* * * * *